(12) United States Patent
Bickel et al.

(10) Patent No.: US 8,916,348 B2
(45) Date of Patent: *Dec. 23, 2014

(54) METHOD AND DEVICE FOR THE DETECTION OF MOLECULAR INTERACTIONS

(75) Inventors: Ralf Bickel, Jena (DE); Alexandra Dworrak, Jena (DE); Thomas Ellinger, Jena (DE); Eugen Ermantraut, Jena (DE); Torsten Schulz, Jena (DE); Thomas Ullrich, Jena (DE)

(73) Assignee: Clondiag GmbH, Jena (DE)

( * ) Notice: Subject to any disclaimer, the term of this patent is extended or adjusted under 35 U.S.C. 154(b) by 1740 days.

This patent is subject to a terminal disclaimer.

(21) Appl. No.: 11/593,021

(22) Filed: Nov. 6, 2006

(65) Prior Publication Data

US 2007/0254372 A1    Nov. 1, 2007

Related U.S. Application Data

(63) Continuation-in-part of application No. PCT/EP2005/004923, filed on May 6, 2005.

(30) Foreign Application Priority Data

| May 6, 2004 | (DE) | 10 2004 022 263 |
| Nov. 4, 2005 | (DE) | 10 2005 052 713 |
| Nov. 4, 2005 | (DE) | 10 2005 052 752 |

(51) Int. Cl.
| C12Q 1/68 | (2006.01) |
| C12M 1/00 | (2006.01) |
| C12M 1/34 | (2006.01) |
| C12M 3/00 | (2006.01) |

(52) U.S. Cl.
USPC .......................................................... 435/6.11

(58) Field of Classification Search
CPC ................................................ B01L 2200/027
See application file for complete search history.

(56) References Cited

U.S. PATENT DOCUMENTS

| 6,400,487 B1 * | 6/2002 | Harris et al. ............... 359/210.1 |
| 6,576,478 B1 * | 6/2003 | Wagner et al. .................. 506/32 |
| 2003/0151735 A1 * | 8/2003 | Blumenfeld et al. ........... 356/73 |
| 2003/0180191 A1 * | 9/2003 | Suzuki et al. ................. 422/102 |
| 2004/0018523 A1 * | 1/2004 | Hawkins .......................... 435/6 |

* cited by examiner

*Primary Examiner* — Robert T. Crow
(74) *Attorney, Agent, or Firm* — Steptoe & Johnson LLP

(57) ABSTRACT

The invention relates to devices and methods for the detection of specific interactions between probe and target molecules. In particular, the invention relates to methods for the qualitative and/or quantitative detection of targets, including: introducing a sample containing targets into a reaction chamber formed between a first surface of the device and a second surface of a device, which is preferably located opposite to the first surface, wherein the distance between the first and the second surface is variable; and detecting the targets.

20 Claims, 35 Drawing Sheets

| | |
|---|---|
|  | 3.<br>Filling of the reaction space |
|  | 4.<br>Separation of the channels from the reaction space and performance of amplification reactions / hybridization, detection<br>If channels or external waste containers are to be contacted for further processing (detection), again in position shown in 3. |

METHOD AND DEVICE FOR THE DETECTION OF MOLECULAR INTERACTIONS

CLAIM OF PRIORITY

This application is a continuation-in-part of, and claims priority under 35 U.S.C. §120 to, International Patent Application PCT/EP2005/004923, filed on May 6, 2005, which designates the United States and claims priority to German Patent Application DE 10 2004 022 263, filed May 6, 2004, each of which is hereby incorporated by reference in its entirety. The present application also claims priority under 35 U.S.C. §119(a)-(d) to German Patent Application DE 10 2005 052 752, filed Nov. 4, 2005, and to German Patent Application DE 10 2005 052 713, filed Nov. 4, 2005, each of which is hereby incorporated by reference in its entirety.

This application also claims priority under 35 U.S.C. §120 to International Patent Application PCT/EP2006/068153, filed 6 Nov. 2006, entitled "Device and Method for the Detection of Particles" and which designates the United States and claims priority to German Patent Application DE 10 2005 052 752, filed Nov. 4, 2005, each of which is incorporated by reference in its entirety; and to International Patent Application PCT/EP2006/068155, filed 6 Nov. 2006, entitled "Methods and Device for the Detection of Molecular Interactions" and which designates the United States and claims priority to German Patent Application DE 10 2005 052 713, filed Nov. 4, 2005, each of which is incorporated by reference in its entirety.

TECHNICAL FIELD

The invention relates to devices and methods for the detection of specific interactions between target and probe molecules.

BACKGROUND

Biomedical tests are often based on the detection of an interaction between a molecule, which is present in known amount and position (the molecular probe), and an unknown molecule to be detected or unknown molecules to be detected (the molecular target molecules). Typically, probes are laid out in the form of a substance library on supports, the so-called microarrays or chips, so that a sample can be analyzed simultaneously at various probes in a parallel manner (see, for example, J. Lockhart, E. A. Winzeler, Genomics, gene expression and DNA arrays; Nature 2000, 405, 827-836). The probes are herein usually immobilized on a suitable matrix, as is for example described in WO 00/12575 (see, for example, U.S. Pat. No. 5,412,087, WO 98/36827), or synthetically produced (see, for example, U.S. Pat. No. 5,143,854) in a predetermined manner for the preparation of the microarrays.

In general, a target molecule labeled with a fluorescence group in the form of a DNA or RNA molecule to a nucleic acid probe of the microarray, that both target molecule and probe molecule are present in the form of a single-stranded nucleic acid. Efficient and specific hybridization can only occur between such molecules. Single-stranded nucleic acid target molecules and nucleic acid probe molecules can normally be obtained by means of heat denaturation and optimal selection of parameters like temperature, ionic strength, and concentration of helix-destabilizing molecules. Probes having virtually perfectly complementary, e.g. corresponding to each other, sequences remain paired with the target sequence (A. Leitch, T. Schwarzacher, D. Jackson, I. J. Leitch, 1994, In vitro Hybridisierung, Spektrum Akademischer Verlag, Heidelberg/Berlin/Oxford).

A typical example for the use of microarrays in biological test methods is the detection of microorganisms in samples in biomedical diagnostics. Herein, it is taken advantage of the fact that the genes for ribosomal RNA (rRNA) are dispersed ubiquitously and have sequence portions, which are characteristic for the respective species. These species-characteristic sequences are applied onto a microarray in the form of single-stranded DNA oligonucleotides. The target DNA molecules to be examined are first isolated from the sample to be examined and are equipped with markers, for example fluorescent markers. Subsequently, the labeled target DNA molecules are incubated in a solution with the probes fixed on the microarray; nonspecifically occurring interactions are removed by means of corresponding washing steps and specific interactions are detected by means of fluorescence-optical evaluation. In this manner, it is possible to detect, for example, several microorganisms simultaneously in one sample by means of one single test. In this test method, the number of detectable microorganisms theoretically only depends on the number of the specific probes, which have been applied onto the microarray.

The use of microarrays or probe arrays is not limited to the detection of target-probe interactions between nucleic acid molecules. Targets can, for example, also be proteins, which are detected by means of specific antibodies functioning as probes. In the same manner, interactions between a protein and low-molecular chemical compounds can be identified if the protein is immobilized on the array in form of a target and the chemical compounds, which can, for example, be a substance library, are immobilized on the array in the form of probes.

Targets can also be analyzed with the aid of conventional immunoassays (for example ELISAs). For instance, antibodies can be immobilized on the base of a well of a micro well plate. Subsequently, a blood sample to be analyzed is fed into said well. If the corresponding antigen is present in the blood sample, it will bind to the immobilized antibody and can then be detected, for example, via a second antibody bearing a fluorescence label.

In the case where cells are to be detected as targets or, for example, the presence of specific antigens on the surface of cells is to be analyzed, cytometric methods are often employed. Said methods are conventionally based on the fact that corresponding, for example fluorescence-labeled, antibodies are added to the sample to be analyzed. Said antibodies then bind to the surfaces of the cells or to the antigens presented there. The sample treated in this manner is subsequently guided through a corresponding capillary in a suitable device and in a suitable solution. Next to the capillary, a detector is arranged, which detects how often within a specific time interval a signal is triggered by a labeled cell flowing by. The number of cells wanted per volume unit can then, more or less exactly, be determined from the fluctuation rate and the signals counted.

SUMMARY

In one aspect, a method includes: forming a mixture between a first surface and a second surface, the mixture including (a) a liquid, (b) a first complex including a first analyte and a first portion of a first optical label, and (c) a second portion of the first optical label, the second portion being in an uncomplexed state with respect to the first analyte, wherein the second portion has a greater mobility than the first complex; reducing a distance between the first surface and the second surface and displacing at least a portion of the mixture from between the first surface and the second surface without introducing a liquid free of the first optical label between the first surface and the second surface; and detecting the first optical label remaining between the first surface and the second surface.

When the complex is immobilized (e.g., linked to a surface), the first portion of the optical label (i.e., that portion of the optical label which is bound to the analyte in a complex) is similarly immobilized. The second portion of the optical label (i.e., that portion which is not bound to an analyte in a complex) remains free in the liquid and able to move in or with the liquid. As such, the second portion of the optical label has a greater mobility than the first (immobilized) portion.

When the complex is not immobilized (e.g., when the complex includes a particle, such as a plastic particle or bead, or a cell), the greater mobility of the second portion of the optical label can arise from the difference in effective sizes of the first portion and second portion of the optical label. For example, optical label which is bound to a particle (i.e., the first portion) can have a greater mass and/or hydrodynamic radius than optical label which is unbound (i.e., the second portion). The smaller size of the unbound optical label can allow the unbound label to move more freely in the liquid, or in other words, to have greater mobility.

The complex can be immobilized with respect to the first surface or the second surface. The mixture can further includes (d) a second complex including a second analyte differing from the first analyte, and a first portion of a second optical label, (e) a second portion of the second optical label, the second portion being in an uncomplexed state with respect to the second analyte, wherein the second portion has a greater mobility than the second complex.

The method can further include detecting the second optical label remaining between the first surface and the second surface. The first optical label and the second optical label can be the same. The first complex can be immobilized with respect to the first surface or the second surface, and the second complex can be immobilized with respect to the first surface or the second surface, and the first complex is spaced apart from the second complex.

The first complex can include a nucleic acid and the second complex can include a nucleic acid. The first complex can be immobilized on the first surface. A microarray of nucleic acids can be immobilized on the first surface.

The second surface can include a displacement structure. The displacement structure can include an elastic material. The displacement structure can have a convex shape.

The first complex can include a nucleic acid, a peptide, a protein, an antigen, an antibody, a carbohydrate, a low molecular weight chemical compound, or a cell.

The distance between the first surface and the second surface can be reduced so that the mixture is substantially completely displaced from between the first surface and the second surface.

The optical label can be a fluorescent label. Detecting the fluorescent label can include detection by a fluorescence microscope without an autofocus. Detecting the fluorescent label can include detection by a fluorescence microscope including a fixed focus.

The first complex can include a nucleic acid. The method can include amplifying the nucleic acid between a first surface and a second surface in a cyclic amplification reaction. The method can include detecting the first complex after one or more cycles of the cyclic amplification reaction.

In another aspect, a device includes a detection zone defined at least in part between a first surface and a second surface, the detection zone being configured to accommodate a mixture including (a) a liquid, (b) a first complex including a first analyte and a first portion of a first optical label, and (c) a second portion of the first optical label, the second portion being in an uncomplexed state with respect to the first analyte, wherein the second portion has a greater mobility than the first complex; an actuator configured to vary a distance between the first surface and the second surface and thereby displace at least a portion of the mixture from between the first surface and the second surface without introducing a liquid free of the first optical label between the first surface and the second surface; and a detector configured to detect the optical label in the detection zone.

The first analyte can be immobilized on the first surface. The first analyte can include a nucleic acid, a peptide, a protein, an antigen, an antibody, a carbohydrate, a low molecular weight chemical compound, or a cell. The first analyte can include a nucleic acid.

The device can include a microarray immobilized on the first surface.

The second surface can include a displacement structure. The displacement structure can include an elastic material. The elastic material can be optically transparent and substantially not autofluorescent. The elastic material can be a two-component platinum-cross-linking silicone rubber. The elastic material can be silicone oil or a non-cross-linked silicone elastomer. The displacement structure can have a convex shape.

The actuator can be configured to vary the distance between the first surface and the second surface in a range from substantially 0 mm to 1 mm. The device can further include a temperature control unit configured to control the temperature in the detection zone. The temperature control unit can be integrated into the first surface. The temperature control unit can include one or more independently controllable temperature blocks. The temperature blocks can be arranged linearly or on a rotary disk.

The detector can include an optical system. The optical system can be a fluorescence-optical system. The fluorescence-optical system can be a fluorescence microscope without an autofocus. The optical system can be operably connected to a spacer which is configured to adjust a spacing between a component of the optical system and the second surface. The second surface can be made of a transparent material.

The detection zone can be further defined by compensation zones configured to maintain the volume of the detection zone at a substantially constant value when the distance between the first surface and the second surface is varied.

The first surface can be configured to move relative to the second surface. At least a portion of the first surface can be elastically deformable. The first surface can include a synthetic elastic material. The actuator can be configured to apply pressure or traction to the first surface to thereby vary the distance between the first surface and the second surface. The actuator can be configured to vibrate the first surface.

The second surface can be configured to move relative to the first surface. The actuator can be configured to apply pressure or traction to the second surface to thereby vary the distance between the first surface and the second surface.

The distance between the first surface and the second surface can be a capillary gap. The capillary gap can have a thickness in a range of about 0 µm to about 100 µm. The device can include a microarray immobilized on the first surface. The capillary gap can include at least two sub-chambers, the sub-chambers being in fluid connection with each other in a first, non-compressed state, and no fluid connection existing between the sub-chambers in a second, compressed state. Each sub-chamber can be assigned to a defined zone of said micro-array. At least one of the first surface and the second surface can be provided with cavities serving as walls between the sub-chambers. The walls between said sub-chambers can be formed by elastic seals.

The device can include a fluid handling unit configured to purify a probe solution, reconcentrate a probe solution, control the charging of the capillary gap with a fluid, or control the discharge of a fluid from the capillary gap. The fluid handling unit and the capillary gap can be connected to each other via two cannulas, said cannulas being arranged so that a first cannula ensures the feeding of fluids from the charging unit and/or reprocessing unit into the capillary gap, and a second cannula ensures the escape of air from the capillary gap expelled by the supplied fluids.

The device can include human or machine readable information associated with the device, the information describing a substance library, execution of an amplification reaction, or a detection reaction.

The device can include a chamber body made of a electrically conductive material. The electrically conductive material can be an electrically conductive plastic. The electrically conductive plastic can be selected from the group consisting of polyamide with 5-30% carbon fibres, polycarbonate with 5-30% carbon fibres, polyamide with 2-20% stainless steel fibres, and PPS with 5-40% carbon fibres.

According to the present invention, methods for the qualitative and/or quantitative detection of molecular interactions between probe and target molecules are provided, wherein the replacement and/or the removal of solutions, i.e. in particular washing or rinsing steps, can be omitted.

In particular, such methods according to the present invention comprise the following steps:
 a) introducing a sample containing target molecules into a reaction chamber having a microarray, said microarray comprising a substrate onto which probe molecules are immobilized on array elements; and
 b) detecting an interaction between the target molecules and the probe molecules immobilized on the substrate, wherein after introducing the sample containing target molecules and prior to and during the detection no replacement of solutions in the reaction chamber and/or removal of solutions from the reaction chamber takes place.

Such methods according to the present invention in particular comprise the following steps: a)
 feeding a sample containing targets into a reaction chamber formed between a first surface of the device and a second surface of the device, which is preferably located opposite said first surface, wherein the distance between the first and the second surface is variable; b)
 detecting the targets.

The method according to the present invention is based on the fact that solution components, which are responsible for unspecific background signals, are displaced from the reaction chamber by means of reducing the distance between the surfaces. In the case of immobilized probes bound to labeled targets, the number of labeled components of the analyte solution, which are not bound to probes, is thereby reduced. Herein, it is preferred that no replacement of solutions has to be performed beforehand.

In one embodiment of the invention, the targets can be detected directly without having to fall back upon probes for detection. In other detection methods according to the present invention, the targets can be detected by means of probes, which can, in turn, be immobilized on one of the surfaces, preferably on a substrate. A further embodiment provides that the probe molecules are not immobilized, but are present together with the targets in the reaction chamber in a dissolved state.

Furthermore, devices suitable for performing such methods are provided within the scope of the present invention.

In particular, within the scope of the present invention a device for the qualitative and/or quantitative detection of molecular interactions between probe and target molecules is provided, comprising:
 a) a microarray on a substrate, onto which probe molecules are immobilized on array elements, said microarray being disposed on a first surface of the device; and
 b) a reaction chamber formed between the first surface including the microarray disposed thereon and a second surface,
wherein the distance between the microarray and the second surface is variable, and wherein the second surface has a displacement structure.

The variability of the distance between the microarray and the second surface, which usually represents the detection surface of the inventive device, particularly allows for a significant reduction or the complete prevention of a signal background that is caused by labeled target molecules having no specific affinity for the probe molecules of the microarray and thus do not interact with them.

In particular, a device for qualitatively and/or quantitatively detecting molecular interactions between probe and target molecules is provided within the scope of the present invention, comprising: a reaction chamber formed between a first surface of the device and a second surface of the device, which is located opposite said first surface, wherein the distance between the first and the second surface is variable and probe molecules in the reaction chamber are immobilized on at least one of the two surfaces, preferably on the first surface.

A further device according to the present invention, which is suitable for performing the methods according to the present invention, comprises a reaction chamber formed between a first surface of the device and a second surface of the device, which is located opposite said first surface, wherein the distance between the first and the second surface is variable and at least one of the two surfaces has a displacement structure, which is positioned in that region of the surface where the detection of the targets is supposed to take place. When the two surfaces approach, the displacement structure leads to a substantially complete displacement of the analyte solution, which is responsible for the background signal noise, from the region where the detection of the targets is supposed to take place. Preferably, said displacement structure is located in the region of the second surface, which is located opposite that region of the first surface where probe molecules can be immobilized. Preferably, the displacement structure can be a bulge.

In the devices according to the present invention, the plane of the reaction chamber, whereto no probe molecules are immobilized, usually is the detection plane.

In particular, the variability of the distance between the surfaces of the reaction chamber allows the signal background, which is caused by labeled targets having no specific affinity to the probes employed and therefore not interacting with the latter, to be considerably reduced or entirely avoided.

In a particular preferred embodiment, the second surface has a displacement structure located on the surface that is facing the microarray. This displacement structure causes a substantially complete displacement of the solution from the reaction chamber if the first and the second surface approach each other.

According to the present invention, a method for the qualitative and/or quantitative detection of molecular interactions between probe and target molecules is also provided, which comprises the following steps:

a) introducing a sample comprising target molecules into a reaction chamber of an inventive device as described above;
b) detecting an interaction between the target molecules and the probe molecules immobilized on the substrate.

The methods and devices according to the present invention for the detection of target molecules are configured in such a way, that as few interventions of the practitioner in the reaction chamber as possible are required for performing the detection method and, optionally, an amplification of the target molecules. This has the essential advantage that contaminations are avoided. Furthermore, the reproducibility of the methods according to the present invention is considerably increased compared to conventional methods, as the inventive method is accessible to automation due to the minimization of external interventions. The above-mentioned advantages play an important role in terms of the approval of diagnostic methods.

The details of one or more embodiments are set forth in the accompanying drawings and the description below. Other features, objects, and advantages will be apparent from the description and drawings, and from the claims.

| | |
|---|---|
| 1 | Filling unit |
| 1.1 | Mechanical interface filling unit - cartridge |
| 2 | Cartridge |
| 2.1 | Mechanical interface cartridge - filling unit |
| 2.2 | Seal |
| 2.3 | Reaction chamber |
| 2.4 | Peferred opening for the cannulas in the cartridge |
| 3 | Filling channel |
| 3.1 | Fluidic and mechanical interface to sample-adding tools |
| 3.2 | Filling cannula |
| 4 | Waste channel with waste container |
| 4.1 | Ventilation hole |
| 4.2 | Waste cannula |

Figure 23A:
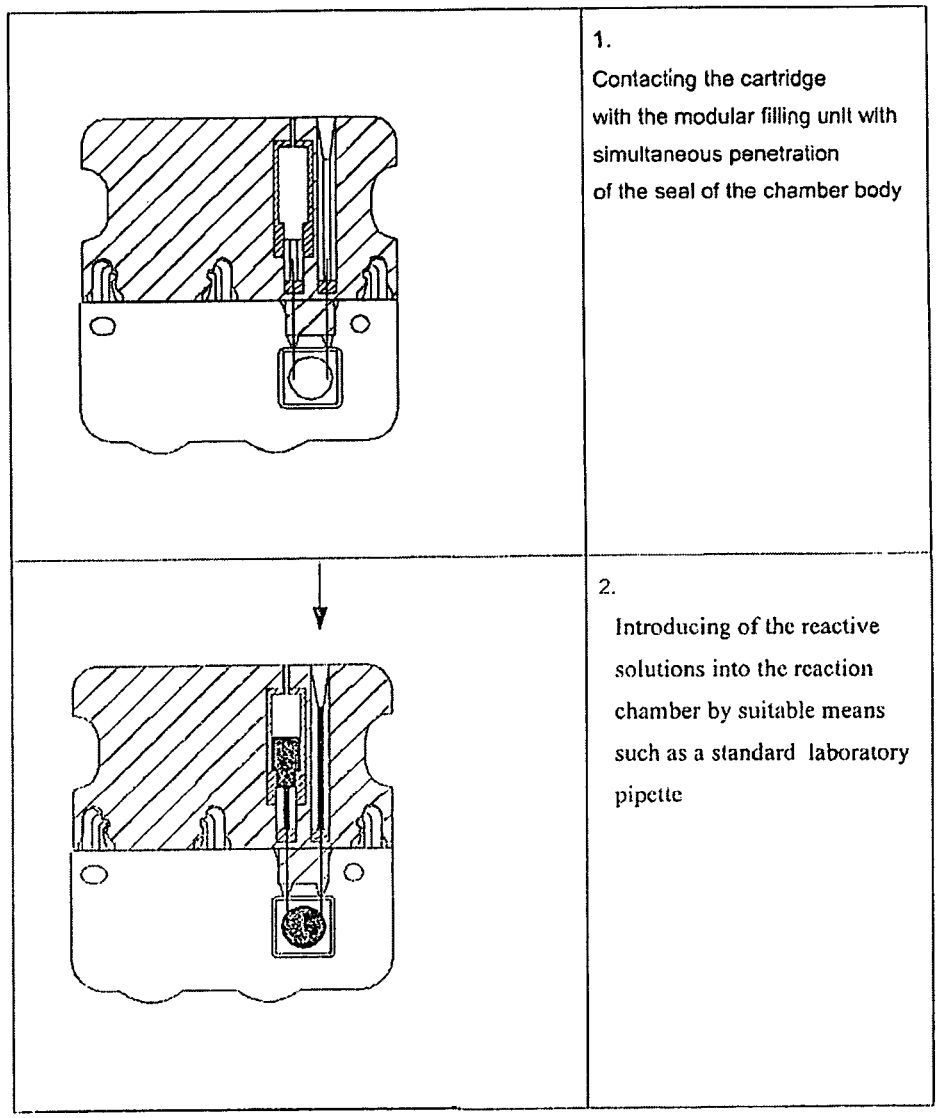
Figure 23B:
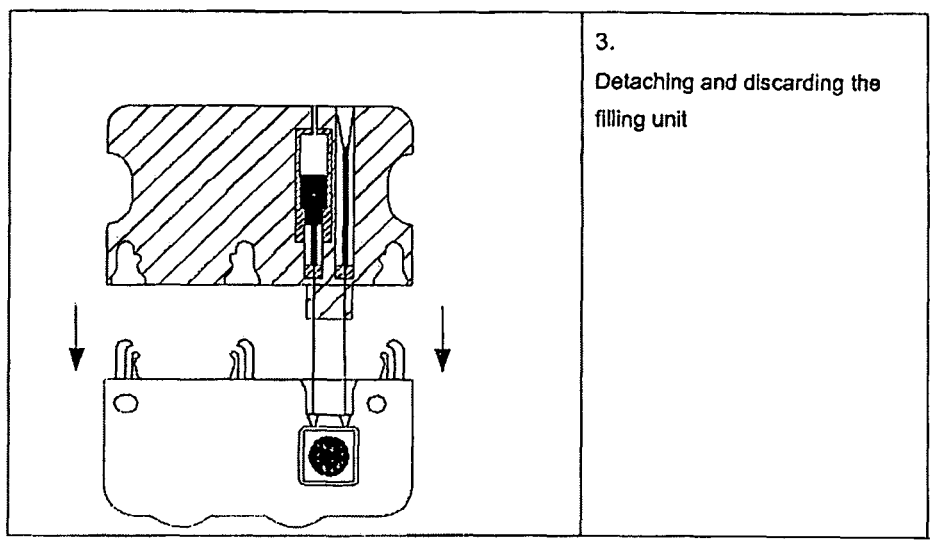

FIG. 23 is a diagram depicting a view of the procedure for filling a reaction cartridge by means of a modular filling unit.

Figure 24:
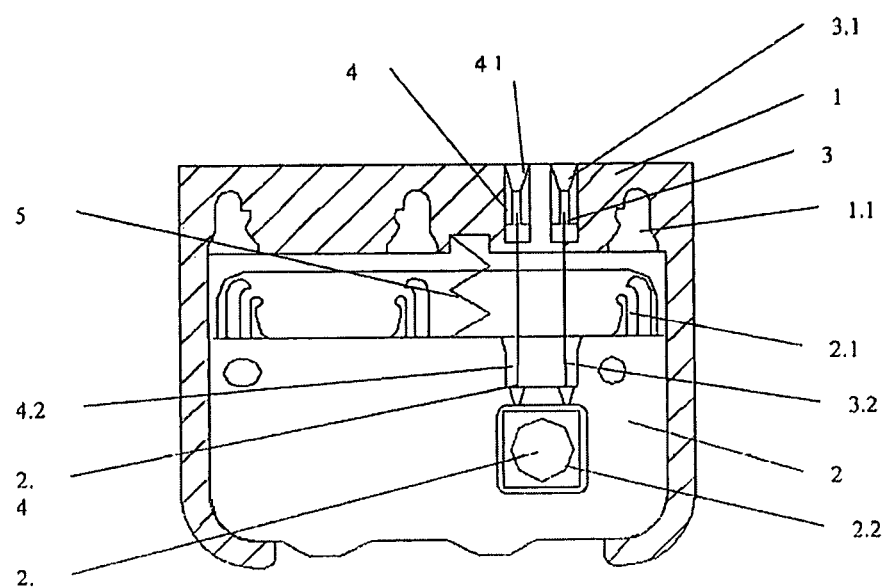

FIG. 24 is a diagram depicting a schematic view of an integrated filling unit for filling reaction cartridges with reactive substances or buffers in the preferred position without penetration of the seal of the chamber body. The following reference numbers are used:

| | |
|---|---|
| 1 | Filling unit - cartridge |
| 1.1 | Mechanical interface cartridge - filling unit |
| 2 | Reaction cartridge |
| 2.1 | Mechanical interface cartridge - filling unit |
| 2.2 | Seal |
| 2.3 | Reaction space |
| 2.4 | Preferred opening for the cannulas in the cartridge casing |
| 3 | Filling channel |
| 3.1 | Fluidic and mechanical interface to sample-introducing tools |
| 3.2 | Filling cannula |
| 4 | Waste channel with waste container |
| 4.1 | Fluidic and mechanical interface to sample-removing units |
| 4.2 | Waste cannula |
| 5 | Equipment for preferred position, here: spring |

Figure 25A:
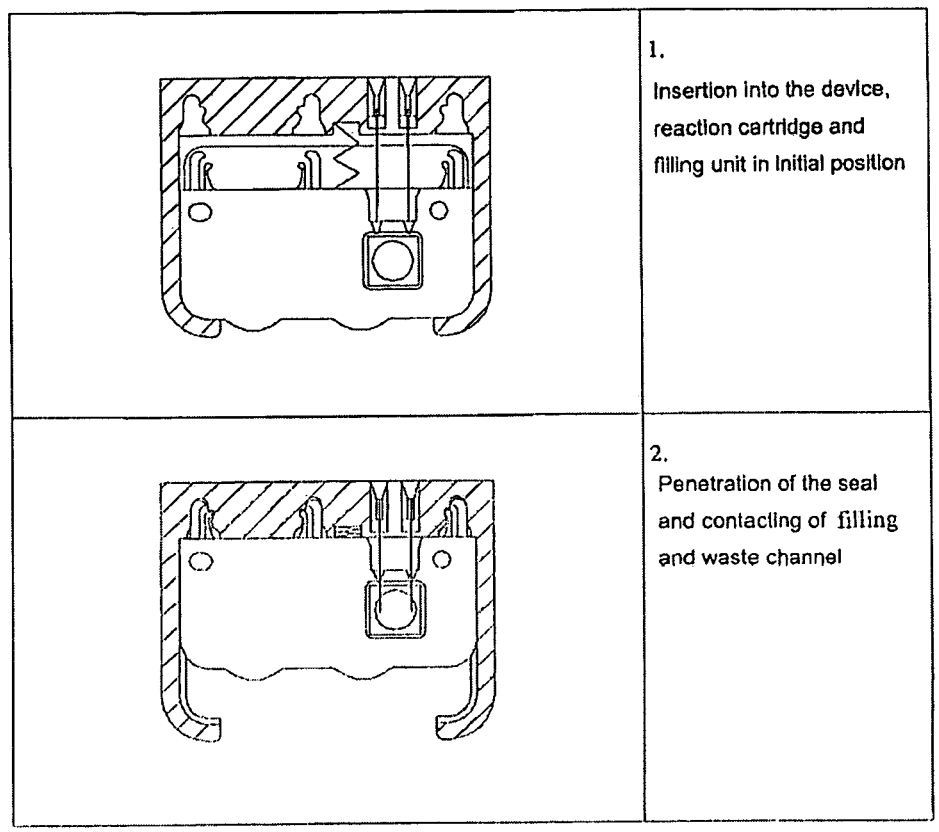
Figure 25B:
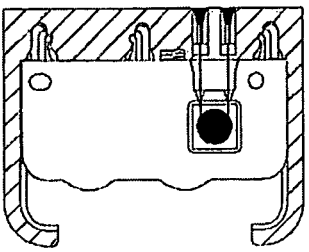
Figure 25B:
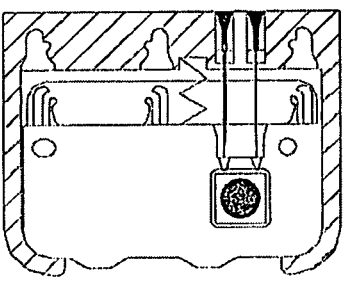

FIG. 25 is a diagram depicting an illustration of the procedure for filling a reaction cartridge having an integrated filling unit.

Figure 26:
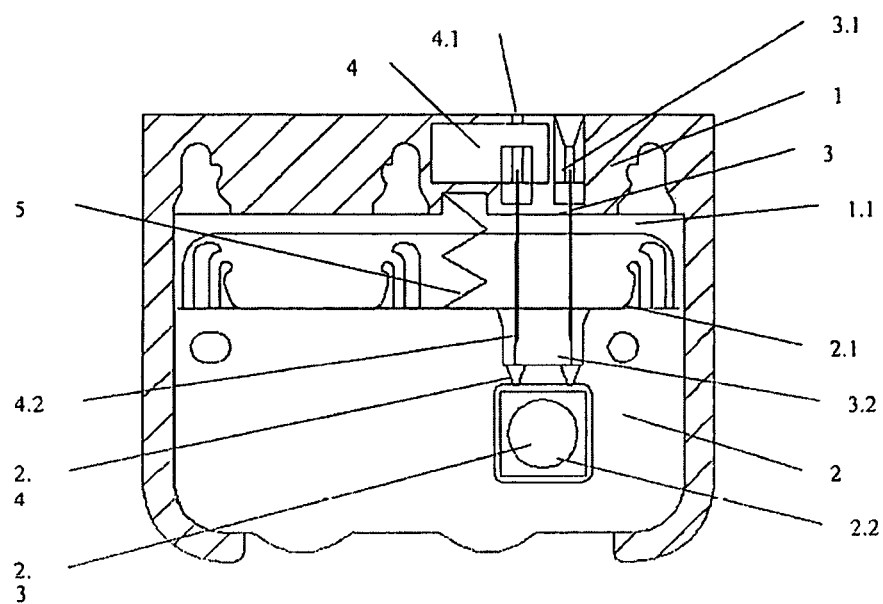

FIG. 26 is a diagram depicting a schematic view of an integrated filling unit having an integrated waste container for filling reaction cartridges with reactive substances or buffers in the preferred position without penetration of the seal of the chamber body. The following reference numbers are used in addition to the reference numbers in FIG. 24:

| | |
|---|---|
| 4 | Waste channel with waste container |
| 4.1 | Ventilation hole |

Figure 27A:
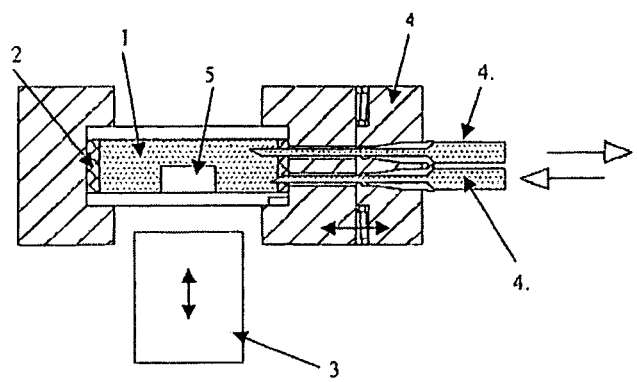
Figure 27B:
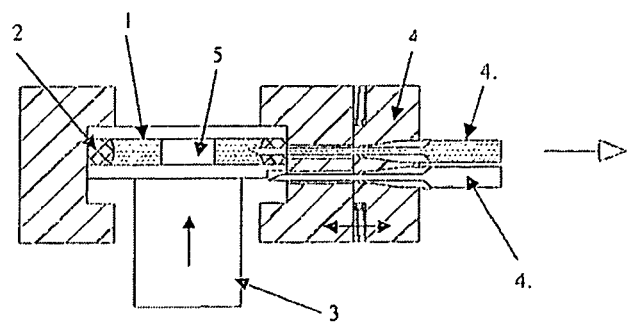

FIG. 27 is a diagram depicting A) Filling of the reaction space when removing the surplus liquid into a waste container or channel, B) removal of surplus liquid when reducing the reaction space for detection. The following reference numbers are used:

| | |
|---|---|
| 1 | Reaction chamber |
| 2 | Seal |
| 3 | Pressure means |
| 4 | Fluid interface |
| 4.1 | Removing cannula |
| 4.2 | Introducing cannula |

Figure 28:
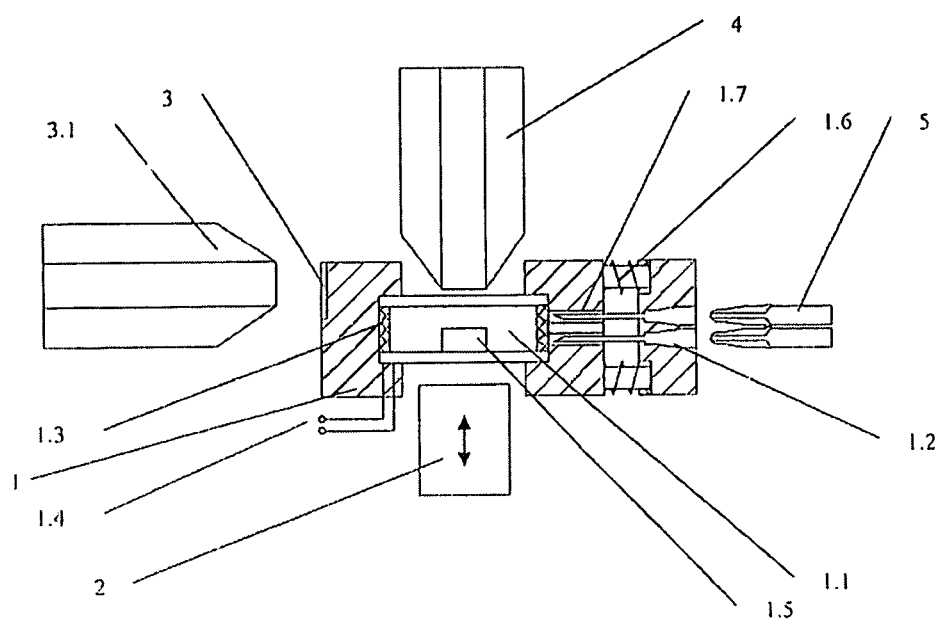

FIG. 28 is a diagram depicting a device for processing and detecting inventive reaction cartridges according to example 4. The following reference numbers are used:

| | |
|---|---|
| 1 | Reaction cartridge |
| 1.1 | Reaction chamber with microarray |
| 1.2 | Fluid system interface |
| 1.3 | Seal of the chamber body |
| 1.4 | Electric connections for heating system, optionally also temperature sensors |
| 1.5 | Chip |
| 1.6 | Position-securing system for implementing a preferred position and guiding the cannulas |
| 1.7 | Cannulas |
| 2 | Pressure means |
| 3 | Identification system, for example bar code or data matrix |
| 3.1 | Identification optics, for example bar code- or data matrix reader |
| 4 | Detection optics |
| 5 | Fluid connections |

Figure 29:
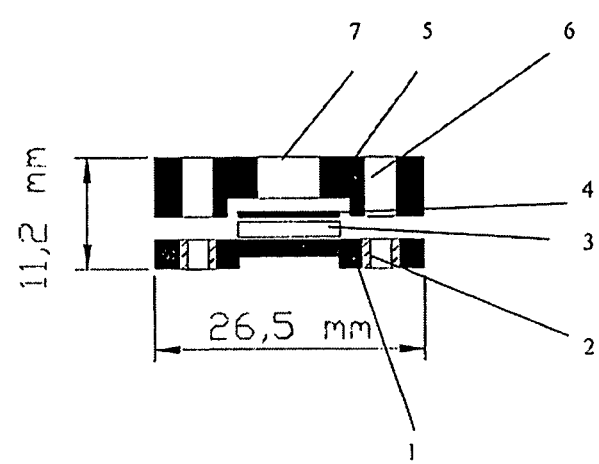

FIG. 29 is a diagram depicting a reaction cartridge according to Example 5.

Figure 30:
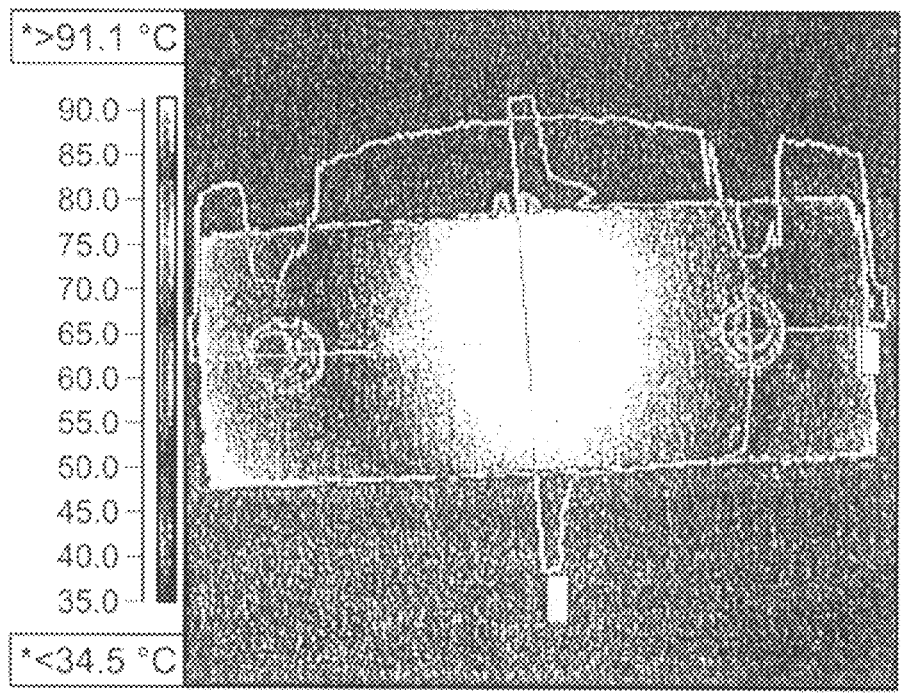

FIG. 30 is a diagram depicting a recording of the reaction cartridge according to example 5 using a thermal imaging camera at a temperature of 95° C.

Figure 31:
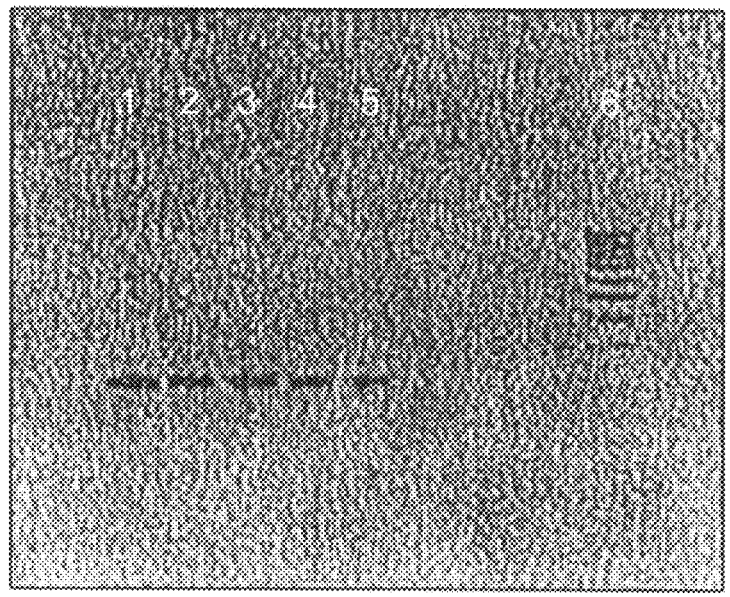

FIG. 31 is a diagram depicting an analysis of the reaction product according to example 5 using agarose gel electrophoresis. The reference numbers indicate:

| | |
|---|---|
| 1, 5: | Positive control from the thermocycler |
| 2-4: | Reaction products from cartridges |
| 6: | 100 bp standard |

Figure 32:
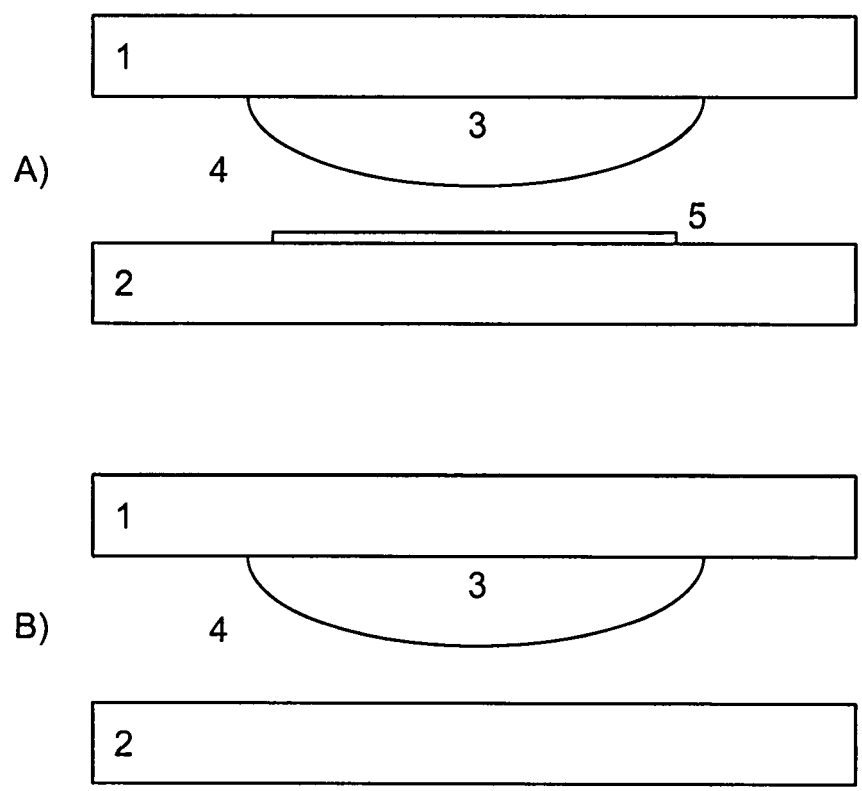

FIG. 32 is a diagram depicting a view exemplarily depicting the arrangement of the displacement structure.

| | |
|---|---|
| 1: | second surface |
| 2: | first surface |
| 3: | displacement structure |
| 4: | solution |
| 5: | microarray |

Figure 33:
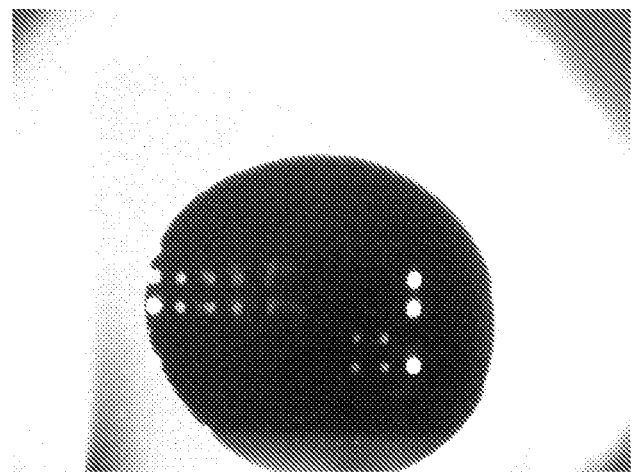

FIG. 33 is a diagram depicting an analysis of the results of example 6, in which the hybridization results of a probe array during detection using the inventive method in a reaction chamber having a displacement structure are described.

Figure 34:
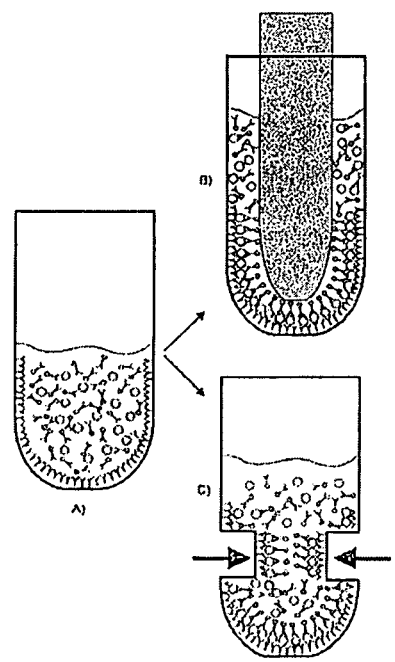

FIG. 34 is a diagram depicting an illustration of devices having a reaction chamber with a first and a second surface, whose distance is variable. (A) depicts probes that are immobilized to one surface of the reaction vessel and the target-containing analyte solution. (B) depicts an arrangement, in which a second surface is provided by a second means such as a tappet. (C) depicts a reaction vessel having elastic surfaces located opposite to each other, which represent the first and second surface of the reaction chamber.

Figure 35:
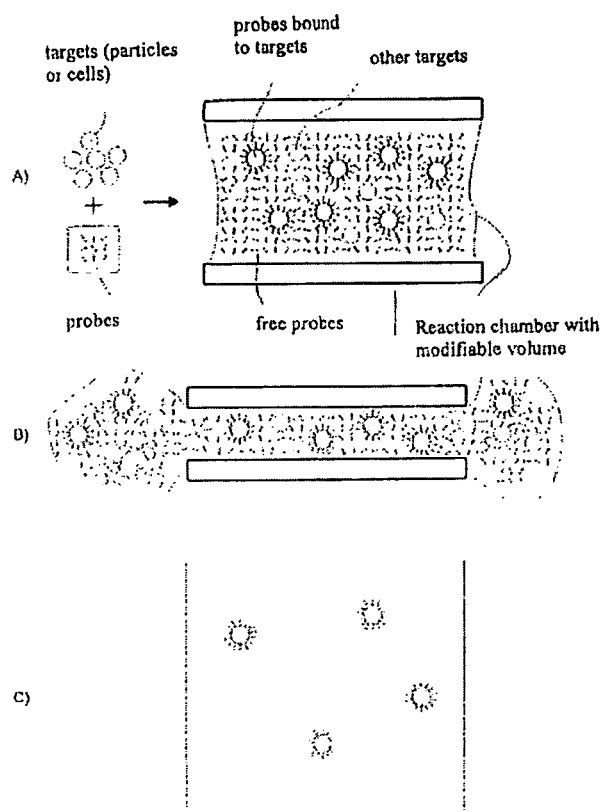

FIG. 35 is a diagram depicting a illustration of a method according to the present invention, wherein the probes are not immobilized to a first surface of the reaction chamber. Such a method can, for example, be employed for cytometric applications.

Figure 36:
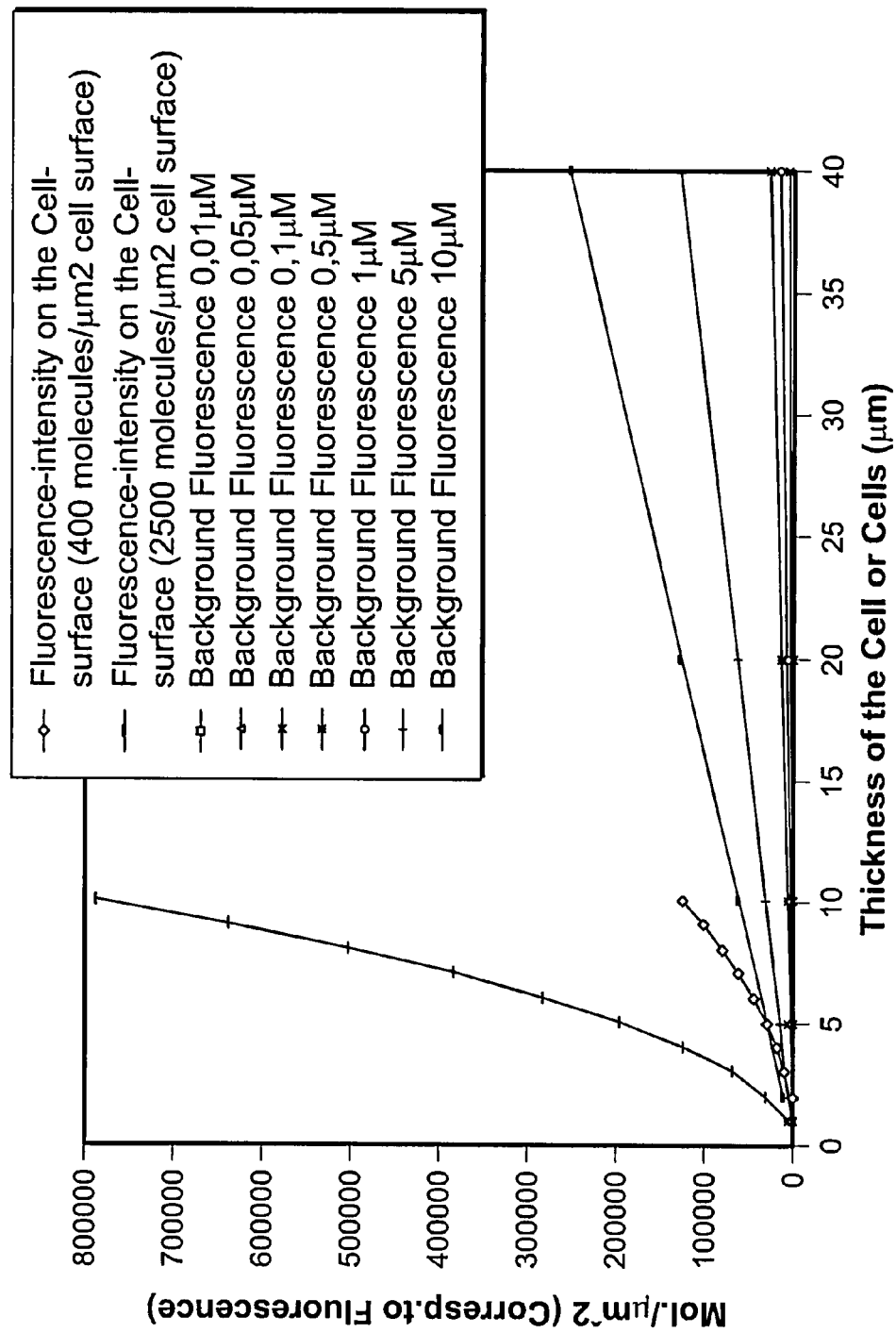

FIG. 36 is a diagram depicting a theoretical illustration of the effect of the chamber and of the thickness of the cells, respectively, on the intensity of the background noise and the signal-to-noise-ratio.

Figure 37:
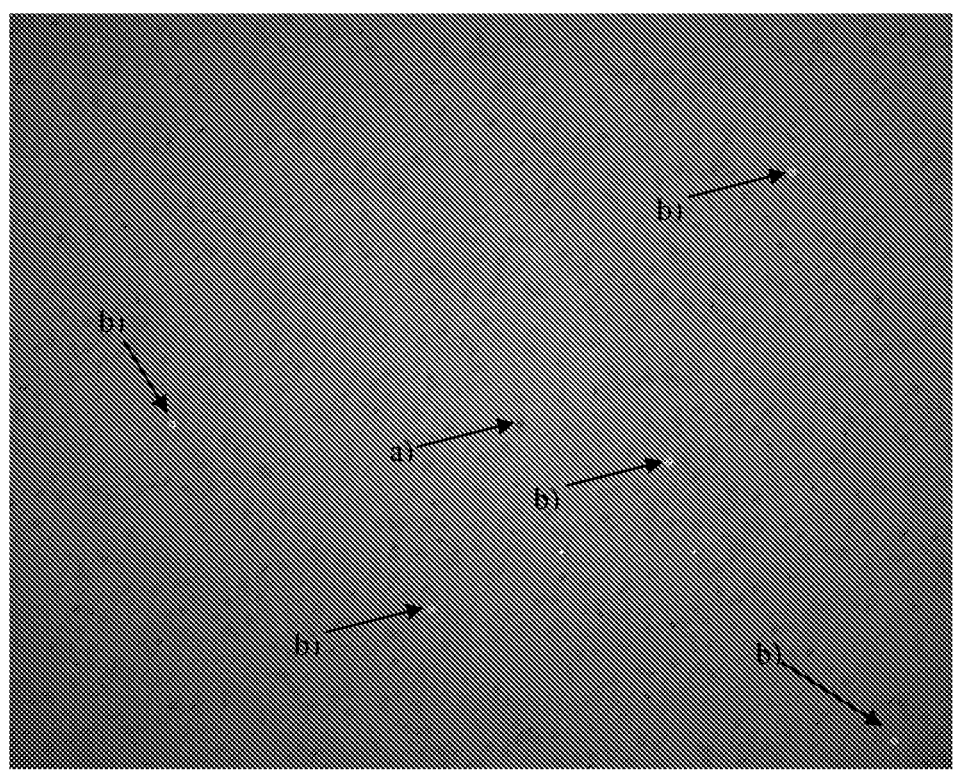

FIG. 37 is a diagram depicting a cytometric determination of $CD4^+$-positive lymphocytes, as described in example 8. (a) depicts unlabeled erythrocytes, (b) depicts $CD4^+$-positive lymphocytes.

DETAILED DESCRIPTION

For the description of the present invention, inter alia the following definitions are used.

Within the scope of the present invention, a probe or a probe molecule or a molecular probe is understood to denote a molecule, which is used for detecting other molecules by means of a particular characteristic binding behavior or a particular reactivity. Each type of molecule, which is suitable for detecting another molecule, i.e. which has a specific affinity for a specific target, can be used as probe. Here, with respect to the methods according to the present invention, it is no prerequisite that probes can be coupled to solid surfaces, like for example substrates. In particular, such molecules having a specific affinity can be used as probes. In a preferred embodiment, these are biopolymers, in particular biopolymers from the classes of peptides, proteins, antigens, antibodies, carbohydrates, nucleic acids, and/or analogs thereof and/or copolymers of the above-mentioned biopolymers. Low-molecular chemical compounds, like the typical components of substance libraries, can also be used as probes. In a preferred embodiment, the probes can be coupled to a solid surface.

In particular, nucleic acid molecules having a defined and known sequence, which are used for the detection of target molecules in hybridization methods, are referred to as probe. Both DNA and RNA molecules can be used as nucleic acids. For example, the nucleic acid probes or oligonucleotide probes can be oligonucleotides having a length of 10 to 100 bases, preferably of 15 to 50 bases, and particularly preferably of 20 to 30 bases. Typically, according to the present invention, the probes are single-stranded nucleic acid molecules or molecules of nucleic acid analogs, preferably single-stranded DNA molecules or RNA molecules having at least one sequence region, which is complementary to a sequence region of the target molecules. Depending on detection method and use, the probes can be immobilized on a solid support substrate, e.g. in the form of a microarray. Furthermore, depending on the detection method, they can be labeled radioactively or non-radioactively, so that they are detectable by means of detection methods conventional in the state of the art.

Likewise preferred are antibodies or ligands, which are known to specifically bind to antigens or cells or cellular structures.

Within the scope of the present invention, a target is generally understood to denote the substance to be detected.

Normally, targets will be molecules; basically, the term "target" is also supposed to comprise, for example, cellular structures or cell types, cell classes or cell tissues, however. In some of the methods according to the present invention, for example, the detection of specific cells of tissue, like for example fibroblasts, or of the immune system, like for example B cells or T cells, is also intended. Depending on which cellular (sub) structures the probes employed for detecting the targets are specific for, a detection of cell subsets, like for example $CD4^+$ or $CD8^+$ cells can also be performed.

Preferably, within the scope of the present invention, a target or a target molecule is understood to denote a molecule to be detected by means of a molecular probe. In a preferred embodiment of the present invention, the targets to be detected are biopolymers from the classes of peptides, proteins, antigens, antibodies, carbohydrates, nucleic acids, and/or analogs thereof and/or mixed polymers of the above-mentioned biopolymers. Targets can also be low-molecular chemical compounds, like components of substance libraries, however. Inorganic materials, for example metals, heavy metals, which can be specifically detected with the aid of detection reagents (for example complex forming agents), are also understood as targets.

If the targets according to the present invention are nucleic acids or nucleic acid molecules, which are detected by means of a hybridization against probes located on a probe array, said target molecules normally include sequences of a length of 40 to 10,000 bases, preferably of 60 to 2,000 bases, also preferably of 60 to 1,000 bases, particularly preferably of 60 to 500 bases and most preferably of 60 to 150 bases. Optionally, their sequence includes the sequences of primers as well as the sequence regions of the template, which are defined by the primers. In particular, the target molecules can be single-stranded or double-stranded nucleic acid molecules, one or both strands of which are labeled radioactively or non-radioactively, so that they are detectable by means of a detection method conventional in the state of the art.

According to the present invention, a target sequence denotes the sequence region of the target, which is detected by means of hybridization with the probe. According to the present invention, this is also referred to as said region being addressed by the probe.

Within the scope of the present invention, a substance library is understood to denote a multiplicity of different molecules, preferably at least two to 1,000,000 different molecules, particularly preferably at least 10 to 10,000 different molecules, and most preferably between 100 to 1,000 different molecules. In special embodiments, a substance library can also comprise only at least 50 or less or at least 30,000 different molecules.

Within the scope of the present invention, a support element or support or substrate is understood to denote a component whereon probes can be immobilized. For the case that no probes are immobilized, the term substrate is supposed to define that region of the first surface or the second surface where the detection of the targets is supposed to take place in the state of the compressed reaction chamber. In both cases (i.e. immobilized probe or non-immobilized probe) the substrate does not have to be an individual component, but it can be a region of the first surface (immobilized probe) or of the first and/or second surface (non-immobilized probe). Substrates can be, for example, object supports or wafers, but also ceramic materials, however. In a special embodiment, the probes can also be immobilized directly on one of the preferably opposite surfaces of the reaction chamber, preferably on a partition of the surface.

Within the scope of the present invention, a probe array is understood to denote an array of molecular probes or a substance library on a support, wherein the position of each probe is determined separately. Preferably, the array comprises defined sites or predetermined regions, so-called array elements, which are particularly preferably arranged in a specific pattern, wherein each array element typically comprises only one species of probes. The arrangement of the molecules or probes on the support can be generated by means of covalent or non-covalent interactions. Therefore, the probes are arranged on the side of the support that is facing the reaction chamber. A position within the arrangement, i.e. within the array, is usually referred to as a spot.

Within the scope of the present invention, an array element or a predetermined region or a spot or an array spot is understood to denote an area on a surface, which is determined for the deposition of a molecular probe, the entirety of all occupied array elements being the probe array.

Within the scope of the present invention, a support element or a support or a substance library support or a substrate can denote a solid body, on which a probe array is located. The support, which is usually denoted a substrate or a matrix, can be, for example, an object slide or a wafer or ceramic materials. In a specific embodiment, the probes may also be immobilized on the first surface, preferably in a portion of the first surface.

Of course, the person skilled in the art is aware of the fact that with microarrays the immobilization of the probes also takes place on substrates, i.e. in defined spatial layout of the spots. The entirety of molecules laid out on the substrate in array layout or the substance library laid out in array layout on the substrate or on the detection plane is often also referred to as chip, microarray, DNA chip, probe array, etc., which are used synonymously for the purposes of the present invention.

Within the scope of the present invention, a detection surface (plane) is understood to denote the second surface of the inventive device. Preferably, during detection the probes deposited on the microarray are substantially located in the detection plane, in particular due to the fact that the distance between microarray and second surface is reduced to about zero.

For example, the detection plane is preferably understood to denote the surface of the device according to the present invention, whereon no probes are immobilized when the detection is performed, for example, in incident light. If the detection is performed in transmitted light, however, no detection surface has to be defined, or, in this case, the first surface and the second surface can function as detection plane. Preferably, the probes laid out on the other surface are substantially located in the plane of the second surface during the detection of the interaction between probes and targets, in particular due to the fact that the distance between the probes of the first surface and the second surface is reduced to about zero.

A displacement structure is denoted to be a structure, preferably configured as a bulge of the second surface, that is located, at least partially, in the area of the second surface, which is located opposite to the microarray and arranged on the side of the second surface that is facing the microarray.

The displacer has the function to substantially displace the (fluorescent) solution between the detection surface (second surface) and the first surface. In the embodiments described below without having a displacement structure, there can occasionally arise the problem that remnants of fluorescent solution remain between the two surfaces, thus causing the background noise mentioned above. This can be avoided by employing a displacement structure, which is preferably configured as a bulge of the second surface.

Numerous materials can be used for displacement structures, with elastic or soft and ductile materials being preferred. Preferably, said materials are optically transparent and not autofluorescent, respectively, so that they do not adversely interfere with detection. Suitable materials may be, for example, silicone rubbers or silicone elastomers, "classic" rubbers, polyurethanes, acrylics, acrylates, and TPE. Particularly preferred are two-component platinum-cross-linking silicone rubbers, such as PDMS. These are optically transparent, not autofluorescent and biologically inert.

Likewise, a liquid, which cannot be mixed with the fluorescent analyte solution or cannot be dissolved in the fluorescent analyte solution, for example silicone oil, may be employed. For example, a silicone rubber (such as Dow Corning Sylgard 184); which does not necessarily need to be cured, may be employed. These materials are preferably not autofluorescent.

The softer the material employed, the better it compensates for unevenness in the surface and for the potential roughness of a surface of the microarray, respectively. If liquid materials are used, they should preferably wet the surface in order to allow an optimal displacement of the fluorescent solution.

The displacement structure, which is preferably configured as bulge, should have an outer shape, which allows for displacing liquid from the reaction chamber and/or from the surface of the microarray in an as efficient manner as possible. Thus, geometric shapes having a convex surface are preferred. As a matter of course, planar, rectangular, or round shapes may be employed as well. In the compressed state, the displacement structure may, for example, cover the entire microarray or only parts thereof. Convex displacement structures are preferred, since they only contact one point of the opposite surface when the reaction chamber is compressed, and, as compression continues, ensure that the opposite surface becomes substantially completely covered, wherein the liquid is laterally displaced from the reaction chamber or from the surface of the microarray. Geometric shapes achieving similar goals are likewise preferred.

The displacement structure may be glued on, dripped on, or deposited and fixed by a suitable means. Other methods, however, are not excluded. For instance, the displacement structure may be configured as one element together with the second surface and thus be manufactured from one piece.

The principle of a displacement structure is exemplarily depicted in FIG. 32.

In performing the methods according to the present invention, wherein the detection of the targets is performed either without probes or by means of non-immobilized probes, both surfaces can likewise be used as detection plane. In this case, the detection of the targets or of the target probes is preferably also performed during the detection in the detection plane, which in turn is preferably achieved by the distance between the first surface and second surface being reduced to about zero. For the case of employing immobilized probes, the substance support usually is part of the chamber body, wherein the substance support can be made of a different material than the rest of the chamber body.

Within the scope of the present invention, a chamber body is understood to denote the solid body forming the reaction chamber. Usually, the substance library support or the chip is part of the chamber body, wherein the substance library support can be made of a different material than the rest of the chamber body.

Within the scope of the present invention, a reaction chamber or a reaction space is understood to denote the space formed between the first surface and the second surface and preferably designed in form of a variable capillary gap. Preferably, the reaction space can be laterally limited by side walls, which can, for example, be implemented as elastic seals. In the case of immobilized probes, these are located on the side facing the interior of the reaction chamber.

Within the scope of the present invention, a reaction chamber or a reaction space is understood to denote the space formed between microarray and second surface or detection surface and preferably configured in form of a variable capillary gap. The reaction space is laterally limited by side walls, which can, for example, be implemented as elastic seals. The probes immobilized on the microarray are located on the side facing the interior of the reaction chamber.

The base area of the reaction chamber or of the reaction space is defined by the first surface or the second surface of the array. The distance between second surface or detection surface and the surface of the substrate or of the microarray is referred to as thickness of the reaction space or of the reaction chamber or of the capillary gap, respectively. The base of the reaction chamber or of the reaction space is defined by the size of the first surface or the second surface. The base of the reaction chamber can also be defined by sections of the first or the second surface. In particular, the distance between first and second surface, and preferably between second surface and surface of the immobilized probes on the first surface is referred to as thickness of the reaction space or of the reaction chamber or of the capillary gap. Within the scope of the present invention, a reaction space usually has a reaction space usually has a thickness providing a volume optimal for the corresponding interaction to be detected. The reaction space can have, for example, a thickness of at most 1 cm, preferably of at most 5 mm, more preferably of at most 3 mm and most preferably of at most 1 mm.

Within the scope of the present invention, the distance between the microarray and the second surface is understood to denote the distance between the surface of the microarray substrate, i.e. of the side of the microarray facing the reaction space, and the side of the second surface facing the reaction space. If the distance between microarray and second surface is about zero, this means that the surface of the substrate rests evenly on the second surface.

Within the scope of the present invention, a capillary gap is understood to denote a reaction space, which can be filled by means of capillary forces acting between the microarray and the second surface. Usually, a capillary gap has a small thickness, for example of at most 1 mm, preferably of at most 750 µm, and particularly preferably of at most 500 µm. Furthermore, according to the present invention, a thickness of the capillary gap in the range of 10 µm to 300 µm, of 15 µm to 200 µm or of 25 µm to 150 µm is preferred. In special embodiments of the present invention, the capillary gap has a thickness of 50 µm, 60 µm, 70 µm, 80 µm or 90 µm. Within the scope of the present invention, the reaction space or reaction chamber will not be referred to as a capillary gap anymore, if the reaction space or the reaction chamber has a thickness of more than 2 mm.

Within the scope of the present invention, a cartridge or reaction cartridge is understood to denote a unit consisting of the reaction chamber with a chamber body and a corresponding casing.

The devices employable for the methods according to the present invention can come in different forms. They can be, for example, reaction vessels like cuvettes or other reaction vessels, provided they have two opposite surfaces, whose distance from each other is variable. An example is to be found in FIG. 5 or FIG. 6. Thus, all reaction vessels having elastic surfaces, which allow the formation of a capillary gap of variable size, can be used as devices for the methods according to the present invention. In particular, the first or the second surface of the reaction vessels should be elastic in those regions where probes are immobilized.

The first and second surface of the devices employable for the methods according to the present invention do not necessarily have to be components of the same object. For instance, a reaction chamber can be generated by means of, for example, inserting an object like a tappet into a reaction vessel like a cuvette. Said object, which is inserted into the reaction vessel, should be dimensioned in such a way that it can be snug-fit into the reaction vessel while leaving a gap representing the reaction chamber but being narrow enough to effect displacement of the solution responsible for the signal noise. In such embodiments, for example, the first surface of the reaction chamber can be provided by the reaction vessel and the second surface can be provided by the object to be inserted.

In all these embodiments, either the first and/or preferably the second surface is made of a transparent material, which allows optical detection of the targets.

Within the scope of the present invention, a confocal fluorescence detection system is understood to denote a fluorescence detection system, wherein the object is illuminated in the focal plane of the objective by means of a point light source. Herein, point light source, object and point light detector are located on exactly optically conjugated planes. Examples for confocal systems are described in A. Diaspro, Confocal and 2-photon-microscopy: Foundations, Applications and Advances, Wiley-Liss, 2002.

Within the scope of the present invention, a fluorescence optical system imaging the entire volume of the reaction chamber is understood to denote a non-confocal fluorescence detection system, i.e. a fluorescence detection system, wherein the illumination by means of a point light source is not limited to the object. Such a fluorescence detection system therefore has no focal limitation.

Conventional arrays or microarrays within the scope of the present invention comprise about 50 to 10,000, preferably 150 to 2,000 different species of probe molecules on a, preferably square, surface of 1 mm to 4 mm×1 mm to 4 mm, preferably of 2 mm×2 mm, for example. In further embodiments within the scope of the present invention, microarrays comprise about 50 to about 80,000, preferably about 100 to about 65,000, particularly preferably about 1,000 to about 10,000 different species of probe molecules on a surface of several mm$^2$ to several cm$^2$, preferably about 1 mm$^2$ to 10 cm$^2$, particularly preferably 2 mm$^2$ to 1 cm$^2$, and most preferably about 4 mm$^2$ to 6.25 mm$^2$. For example, a conventional microarray has 100 to 65,000 different species of probe molecules on a surface of 2 mm×2 mm.

Within the scope of the present invention, a label or a marker is understood to denote a detectable unit, for example a fluorophore or an anchor group, to which a detectable unit can be coupled.

Within the scope of the present invention, a duplication or amplification reaction comprises typically 10 to 50 or more amplification cycles, preferably about 25 to 45 cycles, particularly preferably about 40 cycles. Within the scope of the present invention, a cyclic amplification reaction is preferably a polymerase chain reaction (PCR).

Within the scope of the present invention, an amplification product denotes a product resulting from the duplication or the copying or the amplification of the nucleic acid molecules to be amplified by means of the cyclic amplification reaction, preferably by means of the PCR. A nucleic acid molecule amplified by means of PCR is also referred to as PCR product.

Within the scope of the present invention, the denaturation temperature is understood to denote the temperature at which double-stranded DNA is separated in the amplification cycle. Usually, the denaturation temperature, in particular in a PCR, is higher than 90° C., preferably about 95° C.

Within the scope of the present invention, the annealing temperature is understood to denote the temperature at which the primers hybridize to the nucleic acid to be detected. Usually, the annealing temperature, in particular in a PCR, lies in a range of 50° C. to 65° C. and preferably is about 60° C.

Within the scope of the present invention, the chain extension temperature or extension temperature is understood to denote the temperature at which the nucleic acid is synthesized by means of insertion of the monomer components. Usually, the extension temperature, in particular in a PCR, lies within a range of about 68° C. to about 75° C. and preferably is about 72° C.

Within the scope of the present invention, an oligonucleotide primer or primer denotes an oligonucleotide, which binds or hybridizes the DNA to be detected, also referred to as target DNA, wherein the synthesis of the complementary strand of the DNA to be detected in a cyclic amplification reaction starts from the binding site. In particular, primer denotes a short DNA or RNA oligonucleotide having preferably about 12 to 30 bases, which is complementary to a portion of a larger DNA or RNA molecule and has a free 3-OH group at its 3'-end. Due to said free 3'OH group, the primer can serve as substrate for any optional DNA or RNA polymerases, which synthesize nucleotides to the primer in 5'-3'-direction. Herein, the sequence of the newly synthesized nucleotides is predetermined by that sequence of the template hybridized with the primer, which lies beyond the free 3'OH group of the primer. Primers of conventional length comprise between 12 and 50 nucleotides, preferably between 15 and 30 nucleotides.

A double-stranded nucleic acid molecule or a nucleic acid strand serving as template for the synthesis of complementary nucleic acid strands is usually referred to as template or template strand.

Within the scope of the present invention, a molecular interaction or an interaction is understood to denote a specific, covalent or non-covalent bond between a target molecule and an immobilized probe molecule. In a preferred embodiment of the present invention, the interaction between probe and target molecules is a hybridization.

The formation of double-stranded nucleic acid molecules or duplex molecules from complementary single-stranded nucleic acid molecules is referred to as hybridization. Herein, the association preferably always occurs in pairs of A and T or G and C. Within the scope of a hybridization, for example DNA-DNA duplexes, DNA-RNA duplexes, or RNA-RNA duplexes can be formed. By means of a hybridization, duplexes with nucleic acid analogs can also be formed, like for example DNA-PNA duplexes, RNA-PNA duplexes, DNA-LNA duplexes, and RNA-LNA duplexes. Hybridization experiments are usually used for detecting the sequence complementarity and therefore the identity of two different nucleic acid molecules.

Within the scope of the present invention, processing is understood to denote purification, concentration, labeling, amplification, interaction, hybridization, and/or washing and rinsing steps as well as further method steps performed when detecting targets by using substance libraries. Detection itself does not fall under the term processing.

Within the scope of the present invention, a sample or sample solution or analyte or solution is a liquid to be analyzed, which in particular contains the target molecules to be detected and, optionally, to be amplified. Furthermore, beside conventional additives such as buffers, such a solution may inter alia also contain substances required for performing amplification reactions, like primers.

Within the scope of the present invention, a replacement of solutions in the reaction chamber from the reaction chamber refers, in particular, to rinsing or washing steps. The replacement of solutions serves, for example, for removing molecules labeled with detectable markers, which do not specifically interact with probes on the microarray, by replacing the sample solution with a non-labeled solution after the interaction has occurred. Molecules not specifically interacting with probes on the microarray are, for example, primers labeled with a detectable marker, which have not been converted during the amplification reaction, or target molecules labeled with a detectable marker, which do not have a complementary probe on the array, which specifically interacts with said target molecule.

Within the scope of the present invention, a removal of solutions from the reaction chamber is understood to denote steps, by means of which molecules labeled with detectable markers, which do not specifically interact with probes, are removed from the reaction chamber. Molecules not specifically interacting with probes are, for example, primers labeled with a detectable marker, which have not been converted during the amplification reaction, or target molecules labeled with a detectable marker, which do not have a complementary probe on the array, which specifically interacts with said target molecule.

If, within the scope of the present invention, no replacement of solutions in the reaction chamber and/or removal of solutions from the reaction chamber is performed between feeding the sample containing target molecules into a reaction chamber and detecting the interaction, it is, however, conceivable that during this time period solutions can additionally be introduced into the reaction chamber without performing a replacement or removal of the solutions already present in the reaction chamber.

An object of the present invention thus comprises a method for the qualitative and/or quantitative detection of targets and, in particular of molecular interactions between probe and target molecules, in particular comprising the following steps:

a) introducing a sample containing target molecules into a reaction chamber, which is formed between a first surface of a device and a second surface of a device, wherein the distance between the first and the second surface is variable;
b) detecting the targets.

Preferably, no replacement of solutions in the reaction chamber and/or removal of solutions from the reaction chamber has to be performed after feeding the sample containing target molecules and before or during the detection.

Such a method can, for example, be employed for absorption measurements in solutions without requiring probes for detecting the targets. According to Lambert-Beer's Law, the extinction of a solution is proportional to the concentration of the solution and the layer thickness in which the solution is present. Conventionally, with solutions having too high a concentration, i.e. with solutions having an absorption so high that it cannot be determined reliably anymore, a dilution series is prepared, which is subsequently analyzed. The possibility shown herein is based on the variation of the second parameter, the layer thickness. Alternatively to reducing the concentration, the layer thickness is herein reduced until the absorption of the solution can be measured reliably. As the thickness of the measured layer can be determined, the concentration of the solution can be determined reliably.

Such an embodiment of the method according to the present invention can, for example, be used for determining the concentrations of solutions.

A further object of the present invention comprises a method for the qualitative and/or quantitative detection of molecular interactions between probe and target molecules, in particular comprising the following steps:

a) introducing a sample containing target molecules into a reaction chamber formed between a first surface of a device and a second surface of a device, wherein the distance between the first and the second surface is variable;
b) detecting an interaction between the target molecules and the probe molecules immobilized on the substrate.

In this aspect of the present invention, it is a substantial characteristic of the method according to the present invention that the detection of an interaction between the target molecules to be detected and the probe molecules immobilized on the substrate of the microarray is performed without replacing solutions in the reaction chamber or removing solutions from the reaction chamber. That is, detecting the interaction between targets and probes can be performed without rinsing or washing steps being required subsequently to the interaction reaction and/or without removing molecules, which do not specifically interact with probes on the microarray, from the reaction chamber subsequently to the interaction reaction.

In this embodiment of the method according to the present invention, the probes can, but do not have to, be immobilized on the first surface. This is to be explained in general with reference to FIG. 34.

For instance, a probe can be immobilized at the first surface of any one of the devices mentioned, wherein the probes are not arranged in array layout. It is thus a method for detecting targets by means of employing probe molecules bound to a surface, characterized in that the surface of the first surface is coated completely or partially with at least one type of probe molecules;
the detection is performed in a step, wherein all reagents required are mixed and no further rinsing steps are required for removing material not bound to probes;

the detection is preferably performed under chemical balance conditions;

and the material not bound to probes is removed from the detection volume, for example, by means of mechanical spatial displacement. This can be achieved, for example, by means of compressing the reaction chamber or by means of inserting a separate displacement body (for example a piston) or a liquid insoluble in the actual reaction medium, like for example a mineral oil in aqueous reaction media.

In FIG. 34, A) represents a cuvette with a reaction solution containing target molecules. The inside of the cuvette is coated with probe molecules, which can, for example, be antibodies. In said cuvette, the solution to be examined including the detection reagents is incubated under suitable conditions. Herein, binding of the targets to the probes takes place.

In FIG. 34, B), the cuvette is then shown with targets bound to probes, wherein the superfluous reaction solution is displaced by means of a snug-fit tappet, which preferably forms a small gap as reaction chamber. The tappet can consist of an optically transparent material, for example quartz glass, so that a detection of the bound targets can be performed through the tappet. The tappet can, however, also consist of other materials, for example of a non-fluorescent optically opaque material. Detection could then, for example, be performed by means of incident light (e.g., fluorescence microscopy) detection. In addition, the tappet can be coated with a material improving the displacing effect at surface contact. Such materials referred to as "displacers" will be described in detail in the following. In both cases, at least one surface of the cuvette preferably also consists of transparent materials.

The embodiment shown in FIG. 34, B) represents an example, wherein the first and the second surface of the reaction chamber are provided by different objects, namely tappet and cuvette.

In FIG. 34, C), the cuvette is again shown with bound targets, wherein this time the superfluous reaction solution is displaced from the detection volume by means of compressing the opposite surfaces of the cuvette. In this case, the cuvette again consists of transparent and, moreover, elastic materials. Detection can, for example, take place along the axis of a device for compressing.

This embodiment of the method according to the present invention can, for example, be employed in a sample carousel. Herein, several sample tubules are arranged, for example, in a high throughput screening machine in a carousel. The machine pipettes the samples to be analyzed into the tubules. Said tubules are then guided past a detector and pressed against said detector in a defined manner by means of a suitable device.

In both embodiments described, the solution containing non-bound but labeled targets is reduced in the detection region. This leads to reduction of the unspecific background signal and to improvement of the signal-to-noise ratio.

Of course, the person skilled in the art is aware of the fact that the described embodiments of the methods according to the present invention can also be performed in reaction vessels other than the cuvette described. Among those are, inter alia, the reaction cartridges described in the following.

In principle, the reaction chamber can adopt any exterior shape; it must be possible, however, to reduce its volume.

All hitherto described embodiments as well as all the other embodiments of the present invention have the special advantage that it is possible to analyze the increase of a product formed during the reaction by means of binding the formed product as target to the probes immobilized at the first surface of the reaction chamber, subsequently compressing the reaction chamber in order to reduce its volume, and detecting the signal. Subsequently, the reaction chamber can be relaxed again so that the reaction can continue. After a suitable time period, the reaction chamber is again compressed and the increase of the signal is detected by means of the increased amount of product bound to the probes. This procedure can be performed as often as is desired.

This method is also suitable for creating binding kinetics by means of coating the reaction chamber, for example, with a protein as probe and subsequently adding a further protein, whose binding to the first protein is to be examined, as target. Said second protein can, for example, be directly defined with a fluorescence marker or it can be labeled with an antibody labeled with a fluorescence marker. In relation to the time elapsed, the increase of the signal in the reaction chamber is then detected, wherein the solution covering the probe is reversibly displaced by means of the above-described reduction of the chamber volume.

The method according to the present invention, i.e. the detection of target/probe interactions by means of reducing the volume of the reaction chamber in order to effect the removal of solutions responsible for unspecific signals, can also be employed without immobilization of the probes being required.

This principle shall be explained by way of employing the methods according to the present invention in cytometric methods.

Normally, cytometric methods are based on specially labeled cells being guided through a corresponding capillary in a suitable solution. Next to the capillary, a detector is arranged, which detects how often within a specific time interval a signal is triggered by a labeled cell flowing by. The number of cells wanted per volume unit can then, more or less exactly, be determined from the fluctuation rate and the signals counted.

In the method according to the present invention, non-immobilized probes are employed. Said probes are combined with the targets to be detected. In cytometric applications, the targets can, for example, be cell types. The probes can, for example, be cell-type-specific fluorescence-labeled antibodies.

The solution containing probes and targets is fed into the reaction chamber, the detection volume of which is variable. The reaction chamber is then compressed in a defined manner so that the signal to be detected, which is coming form the surfaces of the cells, rises above the signal intensity of the environment.

FIG. 35 illustrates this principle. In FIG. 35, A), the targets to be detected are placed in a reaction chamber, the detection volume of which is variable in the manner described above, together with suitable detection reagents and are incubated under suitable conditions. Herein, the probes (for example antibodies recognizing specific antigens on the cell surface) bind at the cell surface of the targets, which leads to a relative increase in density of probe molecules compared to the surrounding solution. In FIG. 35, B), the reaction chamber is compressed to form a defined gap for detection, wherein analyte solution is pressed out of the reaction chamber, whose volume can be determined. A specific portion of labeled cells remains in the capillary gap, whose fluorescence can then be detected as they fluoresce brighter than the remaining fluorescent components of the analyte solution. According to FIG. 35, C), the labeled cells can then be imaged in front of the background and be counted, for example, by means of a suitable software. By repeating the steps B) and C) once or several times, a mean value of the number of cells detected per volume unit can be generated and thus the exactness of the measurement can be further increased.

FIG. 36 illustrates the theoretical background of the detection of targets like cells or particles in front of a fluorescent background based on the enrichment of fluorescence-labeled molecules on the surface of the particles. The calculation is based on the assumption that a probe molecule occupies an area of 2,500 $nm^2$ (yielding a density of probe molecules of 400 molecules per $\mu m^2$ cell surface) or 400 $nm^2$ (which rather corresponds to the real conditions, yielding a maximum occupation density of 2,500 molecules per $\mu m^2$ cell surface). For calculating the background fluorescence, quenching effects and the like are omitted. It is assumed that background fluorescence behaves proportionally to the number of fluorescent molecules in the corresponding volume element.

It can clearly be seen that a distinction from the background is already possible with a low occupation density of the cell surface with fluorescent material, if the detection volume is correspondingly narrowed.

In principle, different targets can be detected in a parallel manner with this method. To this end, different probes (for example differently specific antibodies bearing different fluorescence dyes) can be employed on the one hand; on the other hand, however, the geometric shape of the targets to be detected can also be analyzed with corresponding magnification. Here, for example, beads of different sizes or different geometries, which specifically bind in different ways, can be employed.

Basically, the methods according to the present invention have in common that they are performed in reaction chambers, which are formed by a first surface and a second surface, wherein the second surface is located opposite said first surface and the distance between the surfaces is variable in such a way that the volume of the reaction chamber can be reduced to capillary gap size and smaller.

The reaction chambers described in the following for reaction cartridges can in particular be employed as devices in such applications.

An object of the present invention thus comprises a method for the qualitative and/or quantitative detection of targets and, in particular, of molecular interactions between probe and target molecules, in particular comprising the following steps:

a) introducing a sample containing target molecules into a reaction chamber having a microarray, said microarray comprising a substrate onto which probe molecules are immobilized on array elements; and b) detecting an interaction between the target molecules and the probe molecules immobilized on the substrate, wherein after introducing the sample containing target molecules and prior to and during the detection no replacement of solutions in the reaction chamber and/or removal of solutions from the reaction chamber takes place.

In some embodiments, detection of an interaction between the target molecules to be detected and the probe molecules immobilized on the microarray substrate occurs without a replacement of solutions in the reaction chamber or the removal of solutions from the reaction chamber. That is, the detection of the interaction between targets and probes can occur without the requirement of rinsing or washing steps after the interaction reaction has taken place and/or without the removal of molecules from the reaction chamber that do not specifically interact with probes on the microarray after the interaction reaction has taken place This may particularly be ensured in the inventive method by means of foci-selective detection methods, such as confocal techniques or the evanescent de-coupling of excitation light (TIRF) in the sample substrate based on the use of a depth-selective illumination due to, for example, total reflection, or the use of methods based on waveguides. Such foci-selective methods are to be particularly preferred in cases when a further exclusion of the background signals caused by the fluorescence molecules present in the liquid, i.e. not hybridized, in order to increase sensitivity. By using fluorescence-labeled target molecules, the specific interaction signals can thus be discriminated from the background fluorescence by employing methods such as total internal reflection fluorescence microscopy (TIRF) or confocal fluorescence microscopy.

Examples for this are CCD-based detectors, which implement the excitation of the fluorophores in the dark field by means of incident light or transmitted light for the purpose of discriminating optical effects like dispersion and reflections (see for example C. E. Hooper et al., Quantitative Photon Imaging in the Life Sciences Using Intensified CCD Cameras, Journal of Bioluminescence and Chemoluminescence (1990), 337-344). Further alternatives for fluorescence detection systems, which can be used in the method according to the present invention, are white light setups, like for example described in WO 00/12759, WO 00/25113, and WO 96/27025; confocal systems, like for example described in U.S. Pat. No. 5,324,633, U.S. Pat. No. 6,027,880, U.S. Pat. No. 5,585,639, and WO 00/12759; confocal excitation systems based on Nipkow discs in confocal imaging, as for example described in U.S. Pat. No. 5,760,950; systems based on structured excitation distribution, as for example described in WO 98/57151; large-scale integrated fluorescence detection systems using micro-optics, like for example described in WO 99/27140; and laser scanning systems, as for example described in WO 00/12759. A general procedure of fluorescence detection methods using such conventional fluorescence detection systems is, for example, described in U.S. Pat. No. 5,324,633.

The devices described in WO 2004/087951, wherein the reaction chamber is formed by a capillary gap, are particularly suitable for performing a detection method according to the present invention without replacing solutions in the reaction chamber and/or removing solutions from the reaction chamber. The relevant contents of WO 2004/087951 are hereby explicitly referred to.

In a further embodiment of this aspect of the present invention, replacing and/or removing solutions from the reaction chamber is avoided by performing the detection by means of detecting the mass alteration on the array surface, as described, for example, in WO 03/004699. The relevant contents of WO 03/004699 are hereby explicitly referred to.

In a further embodiment of this aspect of the present invention, replacing and/or removing solutions from the reaction chamber is avoided by performing the detection by means of detecting acoustic surface waves, as is described, for example, in Z. Guttenberg et al., Lab Chip. 2005; 5(3):308-17.

In a further embodiment of this aspect of the present invention, replacing and/or removing solutions from the reaction chamber is avoided by performing the detection by means of electrochemical detection via electrodes on the surface of the substrate onto which the probes are immobilized, like, for example, by means of measuring the alteration of redox potentials (see, for example, X. Zhu et al., Lab Chip. 2004; 4(6):581-7) or cyclic voltametry (see, for example, J. Liu et al., Anal Chem. 2005; 77(9):2756-2761; J. Wang, Anal Chem. 2003; 75(15):3941-5).

In a further embodiment of this aspect of the present invention, replacing and/or removing solutions from the reaction chamber is avoided by performing the detection by means of electric detection via electrodes on the surface of the substrate, onto which the probes are immobilized, like, for example, by means of impedance measurement (see, inter alia, S. M. Radke et al., Biosens Bioelectron. 2005; 20(8): 1662-7).

In a further embodiment of this aspect of the present invention, replacing and/or removing solutions from the reaction chamber is avoided by employing a substrate having FRET probes (FRET, fluorescence resonance energy transfer). The use of such FRET probes is based on the formation of fluorescence quencher pairs, so that a fluorescence signal only occurs, if a target molecule has bound to the complementary probe on the surface. The use of FRET probes is, for example, described in B. Liu et al., PNAS 2005, 102, 3, 589-593; K. Usui et al., Mol Divers. 2004; 8(3):209-18; J. A. Cruz-Aguado et al., Anal Chem. 2004; 76(14):4182-8 and J. Szollosi et al., J Biotechnol. 2002; 82(3):251-66.

In a further particularly preferred embodiment of this aspect of the present invention, replacing and/or removing solutions from the reaction chamber is avoided by means of employing an inventive device for the qualitative and/or quantitative detection of molecular interactions between probe and target molecules, as detailed below, wherein the device comprises:
a) a microarray on a substrate, onto which probe molecules are immobilized on array elements, said microarray being disposed on a first surface of the device; and
b) a reaction chamber formed between the first surface including the microarray disposed thereon and a second surface,
wherein the distance between the microarray and the second surface is variable.

In a further particularly preferred embodiment of this aspect of the present invention, replacing and/or removing solutions from the reaction chamber is avoided by means of employing a device according to the present invention for qualitatively and/or quantitatively detecting molecular interactions between probe and target molecules, as is described in detail in the following, wherein the device comprises a reaction chamber formed between a first surface of the device and a second surface of the device, wherein the distance between the first and the second surface is variable and probe molecules are immobilized in the reaction chamber on at least one of the two surfaces.

In an equally preferred embodiment of this aspect of the present invention, replacing and/or removing solutions from the reaction chamber is avoided by means of employing a device according to the present invention for qualitatively and/or quantitatively detecting molecular interactions between probe and target molecules, as is described in detail in the following, wherein the device comprises a reaction chamber formed between a first surface of the device and a second surface of the device, wherein the distance between the first and the second surface is variable and one of the two surfaces has a displacement structure, which leads to volume reduction in a region of the reaction chamber when the two surfaces approach. Preferably, said displacement structure is located in that region of the second surface, which is located opposite the region of the first surface where probe molecules are immobilized.

A further object of the present invention relates to the use of FRET probe molecules, as described above, and/or detection methods selected from the group consisting of total internal reflection fluorescence microscopy (TIRF), as described above, confocal fluorescence microscopy, as described above, methods for detecting mass alterations, as described above, methods for detecting acoustic surface waves, as described above, methods for the electrochemical and/or electric detection, as described above, for avoiding replacement of solutions in a reaction chamber and/or removal of solutions from a reaction chamber during or after introducing a sample containing target molecules into the reaction chamber and before or during the detection in a method for the qualitative and/or quantitative detection of molecular interactions between probe and target molecules, in particular comprising the following steps:
a) introducing a sample containing target molecules into a reaction chamber of one of the devices described above;
b) detecting the targets, in particular by detecting an interaction between the target molecules, preferably immobilized on a substrate on one of the two surfaces.

A further object of the present invention particularly relates to a device for the qualitative and/or quantitative detection of molecular interactions between probe and target molecules, comprising:
a) a microarray on a substrate, onto which probe molecules are immobilized on array elements, said microarray being disposed on a first surface of the device; and
b) a reaction chamber formed between the first surface including the microarray disposed thereon and a second surface,
wherein the distance between the microarray and the second surface is variable.

After the interaction between probe molecules and target molecules has taken place, an undesired background is caused by the labeled molecules present in the sample solution, which do not interact with the probe molecules. In case the probe and/or target molecules are nucleic acids and/or nucleic acid analogs, said background is caused, in particular, by the labeled primers and/or labeled nucleic acids present in the sample solution, which are not hybridized with the probe molecules.

A known possibility of removing disturbing background signals is the replacement of the sample solution after completed interaction with a non-labeled, for example non-fluorescent, solution. However, this variant is generally lavish and prone to interference owing to corrosion, aging of the solutions and impermeability problems.

In some embodiments, the volume of that region of the reaction chamber where the detection of the targets takes place can be reduced by means of varying the distance between the first and the second surface. A variable distance between first and second surface means that the reaction chamber of the device according to the present invention is compressible. In particular, the distance between first and second surface is variable in such a way that the first surface can rest evenly and/or reversibly on the second surface or can be pressed onto the latter. In one embodiment, the distance can, in particular, be reduced in that region of the first or second surface where the probes are immobilized and/or where the displacement structure is mounted.

A compressible reaction chamber therefore allows displacement of sample solution containing labeled molecules, which do not interact with the probe molecules and therefore constitute an undesired background, by reducing the distance between the microarray and the second surface before performing the detection. In this manner, a detection of interactions between probe and target molecules using any optical detection systems is possible without replacing the sample solution with a non-labeled solution before the detection. For example, simple fluorescence-microscopic imaging of the DNA chip for detecting the interaction signals by means of the device according to the present invention without replacing the sample solution with a non-labeled, in particular weakly fluorescent, liquid, is possible. In particular, this applies, if the inventive device has a displacement structure located on the second surface, as described above It is finally ensured, in particular by means of the embodiments of the device according to the present invention described in the following, that focusing of optical detection systems is not necessary anymore. Thus, the device according to the present invention allows, for example, the use of a simple fluorescence microscope device without autofocus function as reading device for the detection of the hybridization between targets and probes without necessitating liquid-handling steps like, in particular, washing steps, for removing target molecules not bound to the array, like for example non-hybridized target nucleic acids, contrarily to the fluorescence-optical detection systems hitherto used for the detection of nucleic acids. This also applies, if the inventive device has a displacement structure located on the second surface, as described above.

Despite multifunctional sample treatment and analysis, which is feasible by means of the device according to the present invention, a very cost-efficient system for detecting and, optionally, amplifying target molecules in a sample is provided. The devices according to the present invention, in particular in connection with an optical detection system, are furthermore robust to such an extent that they are also suitable for mobile use.

By means of suitably selecting the substrates with or without immobilized targets, processing protocols, and analysis chemicals, the device according to the present invention can be employed for the most different types of gene analyses, like for example predisposition diagnostics, germ diagnostics and typing. Thus, a complete genetic analysis is conductible with little equipment effort in the device according to the present invention, which can also be implemented as a disposable cartridge. Therefore, the device according to the present invention allows performing detection methods on-site, for example during blood donation. A measured result can be quickly obtained, preferably within 0.5 to 2 hours. All the steps practicable with the device according to the present invention, like purification, processing, amplification of nucleic acids, and the actual hybridization can be conducted automatically. The operator only needs to be familiar with sample withdrawal, sample feeding into the device according to the present invention, and taking notice of the analysis results.

The same applies for concentration determinations of targets without employing probes, if the targets have absorbing properties or for cytometric applications or target/probe interactions, which are, for example, based on protein/protein interactions.

Preferably, the distance between the first surface (e.g., microarray) and the second surface is variable in a range of about 0 to about 1 mm. Further preferred lower limits for the distance between microarray and second surface are about 0.1 µm, about 1 µm, and about 10 µm. Further preferred upper limits for the distance between the microarray and second surface are about 0.01 mm, about 0.5 mm, about 1 mm and most preferably about 0.3 mm. Surprisingly, the interaction between probes and targets is not even affected if the distance between substrate surface and second surface is approximately zero or about zero. This also applies, if the inventive device has a displacement structure located on the second surface, as described above.

Preferably, the device according to the present invention further comprises a detection system. Herein, it is preferred that the detection system is an optical system. Examples for systems suitable within the scope of the present invention are detection systems based on fluorescence, optical absorption, resonance transfer, and the like. Preferably, the optical detection system is a fluorescence-optical system. Particularly preferably, the fluorescence-optical system is a fluorescence microscope without autofocus, for example a fluorescence microscope with fixed focus.

In a further embodiment, the detection system is connected with at least one spacer, which adjusts a distance between the detection system and the second surface when resting upon the second surface. If the distance between the first and the second surface is about zero, the spacer also determines the distance between the surface of the chip and the optical system of the detection device. It is thus possible to keep the variance of the distance between optical detection device and microarray surface very small. The variance only comprises the thickness variance of the second surface, in general a glass surface, the deflection of the second surface, and the thickness of a layer caused by possible impurities at the pressing surfaces between chip and detection plane or between spacer and detection plane. This renders re-focusing for bringing the optical system into focus unnecessary, which considerably simplifies the operation of the device and/or renders an expensive autofocus installation unnecessary.

In a further embodiment, laterally limiting compensation zones, which keep the volume in the reaction chamber basically constant when the distance between microarray and second surface is reduced, are provided for the reaction space formed between the first and the second surface. This also applies, if the inventive device has a displacement structure located on the second surface, as described above.

In addition, the reaction space formed between the first and the second surface is preferably laterally limited by elastic seals. Particularly preferably, the elastic seals are made of silicone rubber. This also applies, if the inventive device has a displacement structure located on the second surface, as described above.

In order to ensure the detection of interactions between probe and target molecules, the second surface is preferably made of an optically transparent material, particularly preferably glass. The same also applies to an optional displacement structure which, however, may also be made of an elastic and optionally transparent material.

In a further embodiment of the device according to the present invention, the first surface is, at least in the region of the microarray configured in such a way that the first surface can be guided relatively to the second surface in such a way that the distance between the microarray and the second surface is variable.

Herein, the first surface can, at least in the region on which the probes can be immobilized, be configured in such a way that this region can be guided in the direction towards the second surface so that the distance between the first surface and the second surface can be reduced and/or that the microarray can be guided in a direction away from the second surface in a way that that the distance between the microarray and the second surface can be increased. This also applies, if the inventive device has a displacement structure located on the second surface, as described above.

In this embodiment, it is preferred that the first surface can, at least in the region of the microarray, be elastically deformed. Particularly preferably, the first surface is made of an elastic synthetic material, for example an elastic membrane. This also applies, if the inventive device has a displacement structure located on the second surface, as described above.

It can further be preferred that the first surface is formed by two superimposed layers, wherein an outer layer of the two superimposed layers has a cut-out at least in the region below the microarray. In this embodiment, it is preferred that an inner layer of the two superimposed layers is formed by an elastic seal or a sealing membrane, which usually also limits the reaction space laterally (see FIG. 6). The sealing membrane can be guided toward the second surface. The sealing membrane closes a recess in the outer layer, which usually corresponds to the lower side of the chamber body. During the performance of a PCR in the reaction chamber, an internal pressure, which renders the reaction chamber pressure-resistant despite the relatively labile sealing membrane, is generated due to the higher temperatures prevailing in a PCR. This embodiment thus corresponds to a self-closing valve. In order to ensure the elasticity of the sealing membrane, the membrane is preferably provided with a compensation fold (see FIG. 6). This also applies, if the inventive device has a displacement structure located on the second surface, as described above.

It can further be provided that the device comprises at least one means, by which the microarray or probes can be guided relatively to the second surface. In the following, said means will be referred to as means for guiding the first surface. Said means for guiding the first surface is preferably selected from the group consisting of a rod, a pin, a tappet, and a screw. This also applies, if the inventive device has a displacement structure located on the second surface, as described above.

Herein, the device can comprise at least one means for guiding the first surface, by which the first surface can be guided towards the second surface in such a way that the distance between the first and the second surface can be reduced and/or by which the first surface can be guided away from the second surface in such a way that the distance between the first surface and the second surface can be increased. This also applies, if the inventive device has a displacement structure located on the second surface, as described above.

Particularly preferably, at least one region of the first surface can be guided relatively to the second surface by applying pressure and/or traction, which is exerted on the first surface by the means.

Herein, the above-mentioned spacers resting on the second surface can serve as holders for the means for guiding the first surface.

It can further be preferred that the first surface can be caused to vibrate by the means for guiding the first surface, in particular to vibrate at a frequency of 10 to 30 Hz, particularly preferably of about 20 Hz. In this manner, bubbles present above the chip, which would impede a detection, can be removed and/or the interaction speed, for example the hybridization speed, can be increased by a thorough mixing owing to the vibration of the means for guiding the first surface.

It may also be preferred that the second surface can be guided relatively to the first surface in such a way that the distance between the first and the second surface is variable.

There, the second surface can be guided relatively to the first surface in such a way that the distance between the first and the second surface can be reduced and/or that the distance between the first and the second surface can be increased.

In particular, this can be ensured by the second surface being guidable relatively to the first surface by means of the spacer exerting pressure and/or traction on the second surface, such that the distance between the first and the second surface is variable at least in that area where the detection of the target is to be performed.

In a further preferred embodiment of the device according to the present invention, both the first surface and the second surface can be guided in such a way that the distance between the first and the second surface is variable.

Preferably, the first and/or second surface consist of elastic materials at least in those regions where they can be guided relatively to one another. Preferably, such materials are silicone elastomers, like for example Sylgard 184, rubber, silicone rubber or also elastic synthetic materials. TEP, polyurethanes and acrylics or acrylates can also be used as materials.

In a further preferred embodiment, said elastic materials are optically transparent, like for example silicone rubber (for example Sylgard 184).

Preferably, the materials mentioned above are not fluorescent.

Particularly preferred are two-component platinum-cross-linking silicone rubbers (like for example PDMS (Sylgard 184 by Dow Corning)). These are transparent, biologically inert, and not fluorescent.

In a further embodiment, the device according to the present invention is developed in such a way that, already in the original state, the microarray mounted on the first surface rests, preferably evenly, on the second surface forming the detection plane. The first surface can be guided in such a way that the distance between the microarray and the second surface can be increased. Herein, the first surface is preferably made of an elastic material.

In a further embodiment of the device according to the present invention, the first surface is developed in a pivotable manner around a rotation axis. The rotation axis divides the first surface into two sides. In this embodiment, the microarray is arranged on a first flanking portion of the first surface. Preferably, the rotation axis for the swiveling motion runs through the center of the first surface, i.e. the two flanking portions preferably are of equal size. The first surface is preferably made of an elastic material.

In a first position of the pivotable first surface, the first surface is arranged basically parallel to the second surface. In the first position, the surface of the microarray contacts the second surface basically evenly, i.e. the substrate surface with the probe molecules immobilized thereon is basically not moistened by the sample solution. In said first position, a space, which is also referred to as processing chamber in the following, is formed between the second flanking portion of the first surface and the second surface. Said processing chamber can serve as chamber for processing the sample solution.

In a second position of the pivotable first surface, the first surface is arranged at an angle other than 180° in relation to the second surface. In said second position, the surface of the microarray does not contact the second surface, i.e. the probe molecules immobilized on the substrate of the microarray are freely accessible for the target molecules present in the sample solution and can therefore interact with the latter. In the second position, the processing chamber is compressed.

The pivotable first surface can preferably be swiveled by means of exerting traction on the first flanking portion of the first surface and/or by means of exerting pressure on the second flanking portion of the first surface. Pressure and/or traction can be exerted by means of a means for guiding the first surface, as described above.

The preceding embodiments optionally have a displacement structure located on the second surface, as described above, namely on the side of the second surface that is facing the microarray. Thereby, the displacement structure is positioned in such a way that it is located opposite to the microarray and evenly rests on it in the compressed state, wherein during compression the analyte solution being is substantially displaced from the reaction chamber and the surface of the microarray, respectively.

The chip or the substrate or the first surface onto which probes can be immobilized can preferably consist of silicon, ceramic materials like aluminum oxide ceramics, borofloat glasses, quartz glass, single-crystal $CaF_2$, sapphire discs, topaz, PMMA, polycarbonate, and/or polystyrene. The selection of the materials is also to be made dependent on the intended use of the device or the chip. If, for example, the chip is used for characterizing PCR products, only those materials may be used, which can resist a temperature of 95° C.

Preferably, the chips are functionalized by means of nucleic acid molecules, in particular by means of DNA or RNA molecules. However, they can also be functionalized by means of peptides and/or proteins, like for example antibodies, receptor molecules, pharmaceutically active peptides, and/or hormones, carbohydrates and/or mixed polymers of said biopolymers.

In a further preferred embodiment, the molecular probes are immobilized on the substrate surface via a polymeric linker, for example a modified silane layer. Such a polymeric linker can serve for the derivative preparation of the substrate surface and therefore for the immobilization of the molecular probes. In the case of covalent binding of the probes, polymers, for example silanes, are used, which have been functionalized or modified by means of reactive functionalities like epoxides or aldehydes. Furthermore, the person skilled in the art is also familiar with the activation of a surface by means of isothiocyanate, succinimide, and imido esters. To this end, amino-functionalized surfaces are often correspondingly derivatized. Furthermore, the addition of coupling reagents, like for example dicyclohexylcarbodiimide, can ensure corresponding immobilizations of the molecular probes The chamber body of the reaction chamber preferably consists of materials like glass, synthetic material, and/or metals like high-grade steel, aluminum, and brass. For its manufacturing, for example synthetic materials suitable for injection molding can be used. Inter alia, synthetic materials like macrolon, nylon, PMMA, and teflon are conceivable. In special embodiments, electrically conductive synthetic materials like polyamide with 5 to 30% carbon fibers, polycarbonate with 5 to 30% carbon fibers, polyamide with 2 to 20% stainless steel fibers, and PPS with 5 to 40% carbon fibers and, in particular, 20 to 30% carbon fibers are preferred. Alternatively and/or in addition, the reaction space between first and second surface can be closed by means of septa, which, for example, allow filling of the reaction space by means of syringes. In a preferred embodiment, the chamber body consists of optically transparent materials like glass, PMMA, polycarbonate, polystyrene, and/or topaz. Herein, the selection of materials is to be adjusted to the intended use of the device. For example, the temperatures the device will be exposed to are to be considered when selecting the materials. If, for example, the device is to be used for performing a PCR, for example, only those synthetic materials may be used, which remain stable for longer periods at temperatures like 95° C.

In particular, the chamber body is developed in such a way that the microarray can be pressed against the second surface evenly and/or reversibly with its active side, i.e. the side of the array, whereon the nucleic acid probes are immobilized.

Figure 1:
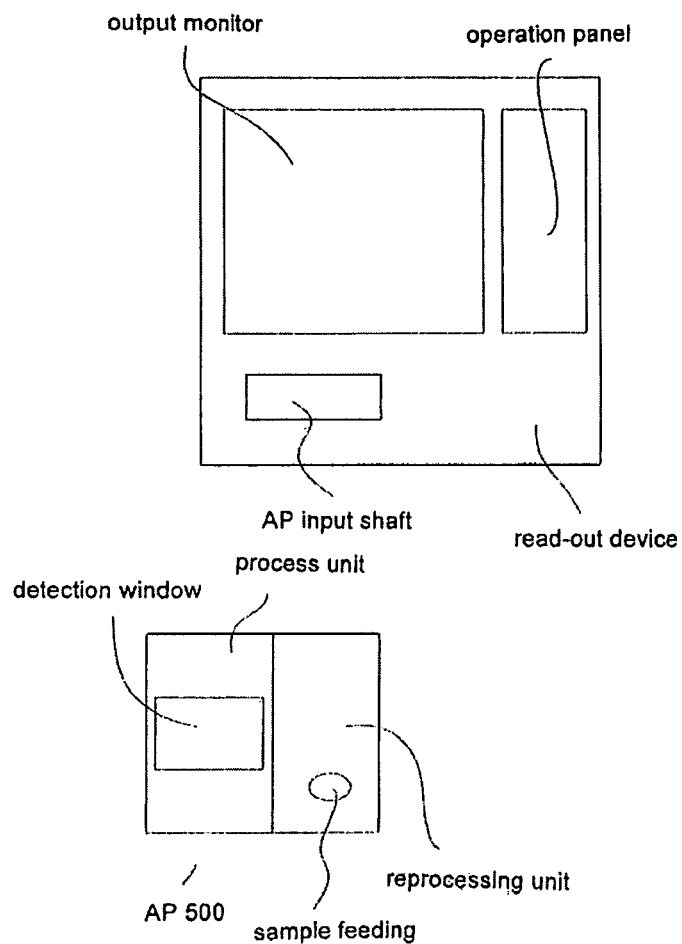
FIG. 1 is a diagram depicting a schematic view of the device according to the present invention comprising a read out device and the process unit.
Figure 2:
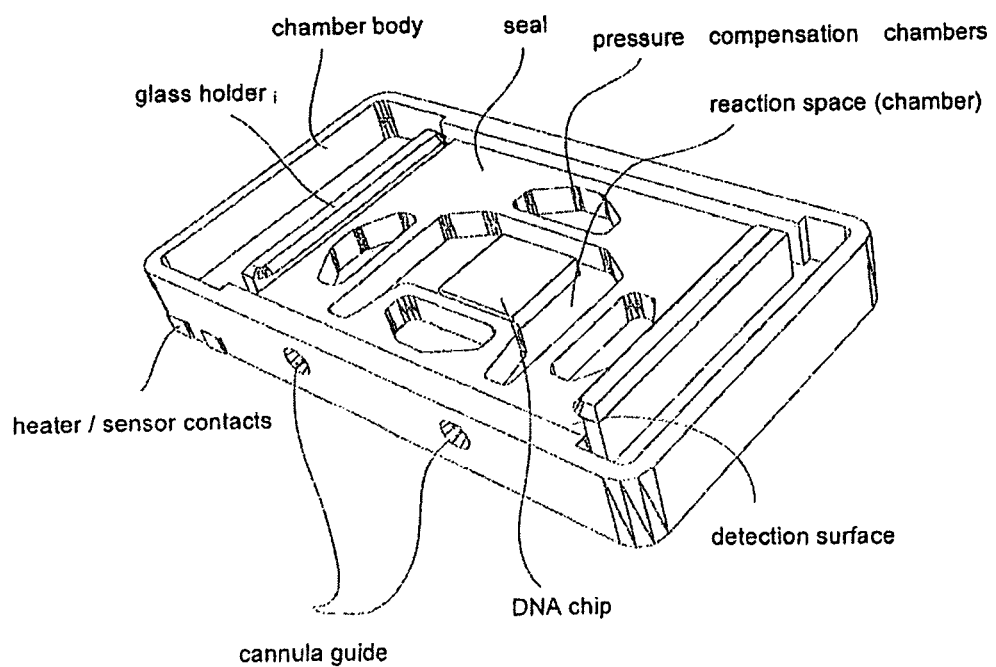
FIG. 2 is a diagram depicting a view of the process unit according to the present invention.
Figure 3:
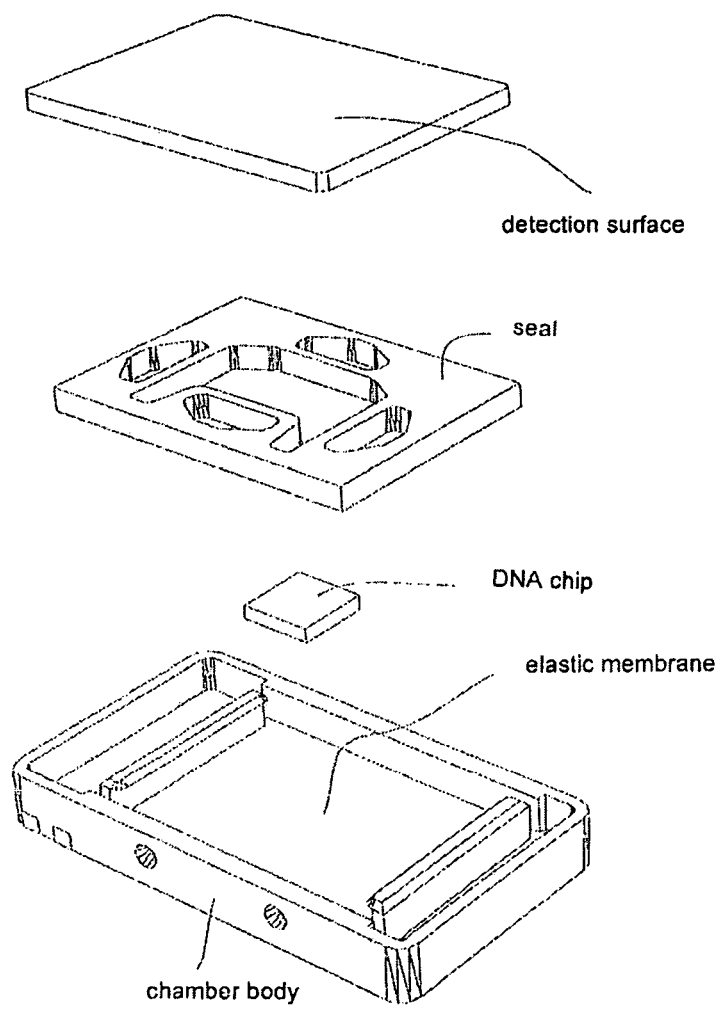
FIG. 3 is a diagram depicting an exploded view of the process unit according to the present invention comprising detection surface, seal, DNA-chip, and chamber body. The chamber body has a reversibly deformable elastic membrane.

In a special embodiment, the device according to the present invention comprises modules selected from the group consisting of a chamber body, preferably made of a synthetic material, a septum or a seal sealing the reaction chamber, a DNA chip, and/or a second optically transparent surface, preferably a glass pane, wherein the second surface can optionally also serve as chip simultaneously (see FIG. 2 and FIG. 3). In this embodiment, chamber body and seal are developed elastically, so that the DNA chip can be pressed evenly and reversibly to the glass cover with its active side. Thereby, the labeled analysis liquid located between DNA chip and detection surface is entirely displaced (see FIG. 5 and FIG. 6). In this manner, a highly sensitive fluorescence detection, for example a computer-imaging fluorescence microscopy, can be conducted without being impaired by a background fluorescence of the sample solution.

Preferably, the second surface of the chamber body consists of transparent materials like glass and/or optically permeable synthetic materials, for example PMMA, polycarbonate, polystyrene, or acryl. The displacement structures mentioned above, if present, may be made of these materials or of the above-mentioned materials.

Preferably, the reaction chamber is developed between the second surface and the microarray in the form of a capillary gap having variable thickness. By forming a capillary gap between chip and detection plane, capillary forces can be utilized for safely filling the reaction chamber. Said capillary forces already occur in the non-compressed state of the reaction chamber; they can, however, be increased by compressing the reaction chamber. Particularly preferably, the capillary gap has a thickness in the range of about 0 μm to about 100 μm. This also applies, if a displacement structure is present, as described above From the possibility of being able to compress the reaction space and therefore to reduce the width of the gap between microarray and detection plane, further possibilities of handling the liquid within the reaction chamber arise. Thus, in a further embodiment of the present invention, several sub-chambers are provided instead of one single chamber, wherein the partitions between said sub-chambers do not reach the height of the second surface, so that a fluid connection is generated between the sub-chambers in a non-compressed state of the reaction chamber. By compressing the reaction chamber, the chambers can be separated. Thus, by compressing, the partitions between the chambers can be operated like valves.

A special embodiment of said sub-chambers separated by valves is the subdivision of the reaction space of the device according to the present invention into different PCR chambers. In each chamber, individual primers are presented. In the beginning, the sub-chambers are simultaneously filled with the analyte. Subsequently, the reaction space is compressed. Afterwards, the reaction space is subjected to the temperature cycle for the PCR. As each sub-chamber is filled with different primers, a different amplification reaction takes place in each chamber. An exchange between the chambers does not occur.

After the PCR has been performed, hybridization takes place. Herein, each sub-chamber can contain an individual chip region or an individual chip. However, it is also possible to facilitate a fluid connection between the sub-chambers by increasing the distance between microarray and second surface, so that the different substances to be amplified mix and in this manner hybridize to a chip surface.

The advantage of this embodiment having sub-chambers separated by valves is the increase in multiplexity of the PCR, i.e. the number of independent PCRs with one sample, which is limited for biochemical reasons in a one-stage reaction. Thus, it is possible to adjust the number of PCRs to the possible number of probes on the chip surface.

In a further embodiment of the present invention, the reaction chamber thus comprises at least two sub-chambers, wherein in a first non-compressed state the sub-chambers are in fluid connection and in a second compressed state there is no fluid connection between the sub-chambers.

Particularly preferably, each sub-chamber is assigned to a defined region of the microarray.

In particular, the sub-chambers can be formed by equipping the microarray and/or the second surface with cavities, which serve as walls between the sub-chambers.

Particularly preferably, the walls between the sub-chambers are formed by elastic seals.

Of course, this embodiment of the process unit having sub-chambers separated by valves can arbitrarily be combined with any of the above-described compression principles.

In a further embodiment of the device according to the present invention, the first surface is made of a partially deformable elastic material, for example an elastic membrane. In that only a part of the reaction space can be compressed, sub-chambers, wherein the chip is guided toward the second surface, sub-chambers, which cannot be separated from each other, and sub-chambers, which cannot be altered, can, inter alia, be generated. Thereby, simple pump systems, which can, for example, be used for pumping salts into the hybridization chamber at the end of an amplification reaction, can be implemented in the reaction space. This can, for example, be advantageous for optimizing the chemical hybridization conditions of the PCR buffer, wherein the PCR buffer is optimized only for the conduction of the PCR.

When subdividing the reaction chamber into several sub-chambers, it is preferred to use several means for agitating. Usually, the means for agitating are identical with the means for guiding the first surface. Thereby, individual chambers can be specifically agitated. This can, for example, be appropriate for implementing separate amplification spaces and/or hybridization spaces.

Of course, this embodiment of the device according to the present invention having several means for agitating can also be arbitrarily combined with any of the above-described compression principles.

The above-described components or modules of the device according to the present invention selected from the group consisting of a chamber body, seals laterally limiting the reaction space, micro-array, and detection plane form the so-called process unit of the inventive device. In the process unit, PCR, hybridization reactions, detection and/or evaluation can be performed. This is similarly true for probes and targets being, for example, antibodies and proteins to be detected, thus a PCR does not have to be carried out. However, the following explanations are particularly done with regard to detection techniques using nucleic acid targets and -probes. However, it is clear to the person skilled in the art how to modify the units described in the following to adapt them for other applications.

Preferably, the process unit of the device according to the present invention is constructed in a modular manner. This means that the process unit can comprise any arbitrary combination of the modules. The modules can also be exchanged during analysis.

The preceding embodiments optionally have a displacement structure located on the second surface, as described above, namely on the side of the second surface that is facing the microarray. Thereby, the displacement structure is positioned in such a way that it is located opposite to the microarray and evenly rests on it in the compressed state, wherein during compression the analyte solution being is substantially displaced from the reaction chamber and the surface of the microarray, respectively.

In a further preferred embodiment, the device according to the present invention in addition comprises a temperature controlling and/or regulating unit for controlling and/or regulating the temperature in the reaction chamber. Such a temperature controlling and/or regulating unit for controlling and/or regulating the temperature in the reaction chamber in particular comprises heating and/or cooling elements or temperature blocks. Herein, the heating and/or cooling elements or the temperature blocks can be arranged in such a way that they contact the first surface and/or the second surface. By means of contacting both the first and the second surface, particularly efficient temperature controlling and regulating is ensured.

In this embodiment, the substrate of the microarray or the first surface and/or the second surface is connected with heating and/or cooling elements and/or temperature blocks and should then preferably consist of materials with good heat-conducting properties. Such heat conductive materials offer the considerable advantage of ensuring a homogenous temperature profile throughout the entire surface of the reaction space and therefore allowing temperature-dependent reactions, like for example a PCR, to be conducted homogenously throughout the entire reaction chamber, delivering high yields, and controllably or regulatably with high accuracy.

Thus, in a preferred embodiment, the substrate of the microarray or the first surface or the second surface consist of materials having a good heat conductivity, preferably having a heat conductivity in a range of 15 to 500 $Wm^{-1}K^{-1}$, particularly preferably in a range of 50 to 300 $Wm^{-1}K^{-1}$, and most preferably in a range of 100 to 200 $Wm^{-1}K^{-1}$, wherein the materials are usually not optically transparent. Examples for suitable heat conductive materials are silicon, ceramic materials like aluminum oxide ceramics, and/or metals like high-grade steel, aluminum, copper, or brass.

If the substrate of the microarray or the first surface or the second surface of the device according to the present invention substantially consists of ceramic materials, the use of aluminum oxide ceramics is preferred. Examples for such aluminum oxide ceramics are the ceramics A-473, A-476, and A-493 by Kyocera (Neuss, Germany).

Preferably, the substrate of the microarray or the first surface or the second surface is equipped with optionally miniaturized temperature sensors and/or electrodes or has heater structures on its back side, i.e. the side facing away from the reaction chamber, so that tempering the sample liquid and mixing the sample liquid by means of an induced electro-osmotic flow is possible.

The temperature sensors, for example, can be developed as nickel-chromium thin film resistance temperature sensors.

The electrodes, for example, can be developed as gold-titanium electrodes and, in particular, as quadrupole.

The heating and/or cooling elements can preferably be selected in such a way that fast heating and cooling of the liquid in the reaction chamber is possible. Herein, fast heating and cooling is understood to denote that temperature alterations in a range of 0.2 K/s to 30 K/s, preferably of 0.5 K/s to 15 K/s, particularly preferably of 2 K/s to 15 K/s, and most preferably of 8 K/s to 12 K/s or about 10 K/s can be mediated by the heating and/or cooling elements. Preferably, temperature alterations of 1 K/s to 10 K/s can also be mediated by the heating and/or cooling elements.

The heating and/or cooling elements, for example resistance heaters, can, for example, be developed as nickel-chromium thin film resistance heaters.

For further details on the specification and dimension of the temperature sensors, heating and/or cooling elements or means for increasing the temperature and of the electrodes, it is referred to the contents of the International Patent Application WO 01/02094.

In a preferred embodiment, tempering of the reaction chamber is ensured by using a chamber body consisting of electrically conductive material. Such an electrically conductive material is preferably an electrically conductive synthetic material, like for example polyamide, optionally having 5 to 30% carbon fibers, polycarbonate, optionally having 5 to 30% carbon fibers, and/or polyamide, optionally having 2 to 20% stainless steel fibers. Preferably, PPS (polyphenylenesulfide) with 5 to 40% carbon fibers, particularly preferably 20 to 30% carbon fibers, is used as electrically conductive synthetic material. It is further preferred that the chamber body is developed in such a way that it has swellings and tapers. Such swellings or tapers in the chamber body allow specific heating of the reaction chamber or the corresponding surfaces. Furthermore, the use of such volume conductors has the advantage that, also with optionally lower heat conductivity of the material used, homogenous tempering of the chamber or the corresponding surfaces is ensured, as heat is released in each volume element.

Coupling and educing heat into the reaction space can be conducted in different ways. Inter alia, it is intended to bring in heat via external microwave radiation, internal or external resistance heating, internal induction coils or surfaces, water cooling and heating, friction, irradiation with light, in particular with IR light, air cooling and/or heating, friction, temperature emitters, and peltier elements.

Measuring the temperature in the reaction space can be conducted in different ways, for example by means of integrated resistance sensors, semi-conductor sensors, light waveguide sensors, polychromatic dyes, polychromatic liquid crystals, external pyrometers like IR radiation and/or temperature sensors of all types, which are integrated in the means for guiding the microarray.

Measuring the temperature in the reaction chamber can furthermore be conducted by means of integrating a temperature sensor in the chamber body, for example by means of injection in the course of the production process of the chamber body, by means of non-contact measurement with the aid of a pyrometer, an IR sensor, and/or thermopiles, by means of contact measurement, for example with a thermal sensor integrated in the device and contacting a suitable surface or a suitable volume of the chamber body or the chamber, by means of measuring the temperature-dependent alteration of the refraction index at the detection plane, by means of measuring the temperature-dependent alteration of the color of specific molecules, for example in the solution, on the probe array, or in the chamber seal, and/or by means of measuring the temperature-dependent alteration of the pH-value of the solution used by means of measuring the color alteration of a pH-sensitive indicator, for example by means of measuring its absorption.

Furthermore, automatic limitation of temperature can occur due to a surge of the resistance of the heater, wherein the corresponding threshold temperature preferably lies in a range of 95° C. to 110° C. When reaching the threshold temperature, the resistance of the heater surges, whereby virtually no current flows and therefore virtually no heat is emitted anymore. In particular, polymers, like electrically conductive polyamides, whose resistance increases at the threshold temperature due to the alteration of the matrix of the polymer or a phase alteration, can be used for such heaters.

Figure 4:
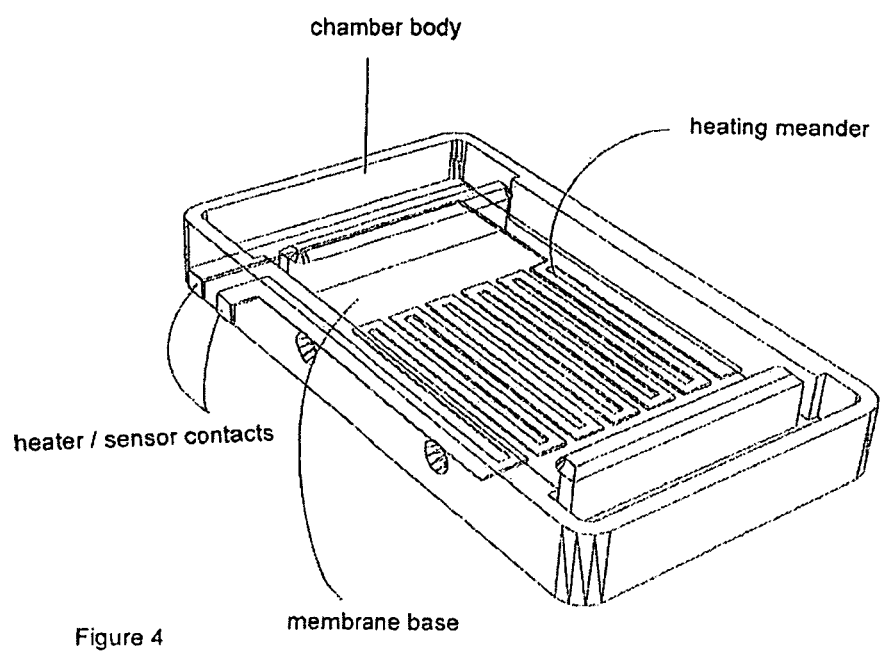
FIG. 4 is a diagram depicting a view of the chamber body having a heating meander embedded by injection-molded synthetic material in the elastic membrane.

In one embodiment, the temperature controlling and regulating unit can be integrated in the first surface and/or the second surface. In said embodiment, the process unit is, in particular, equipped with a heater (see FIG. 4), which serves for implementing the temperature alterations in PCR and hybridization.

Preferably, the process unit has a low heat capacity, so that maximum temperature alteration speeds of, for example, at least 5 K/s are practicable at a low power demand. In order to ensure fast cooling of the process unit, another preferred embodiment intends providing a cooling system, for example an air cooling system.

Preferably, cooling of the process unit can also be achieved by means of permanently tempering the space surrounding the process unit to a lowered temperature and thereby passively cooling the cartridge. This renders active cooling of the reaction cartridge unnecessary.

In a further embodiment, the temperature controlling and regulating unit can comprise temperature blocks, which are each pre-heated to a defined temperature. In said embodiment the process unit, in particular, has no integrated heater. Owing to the omission of an integrated heating system, the process unit can be provided even more cost-efficiently.

Figure 7:
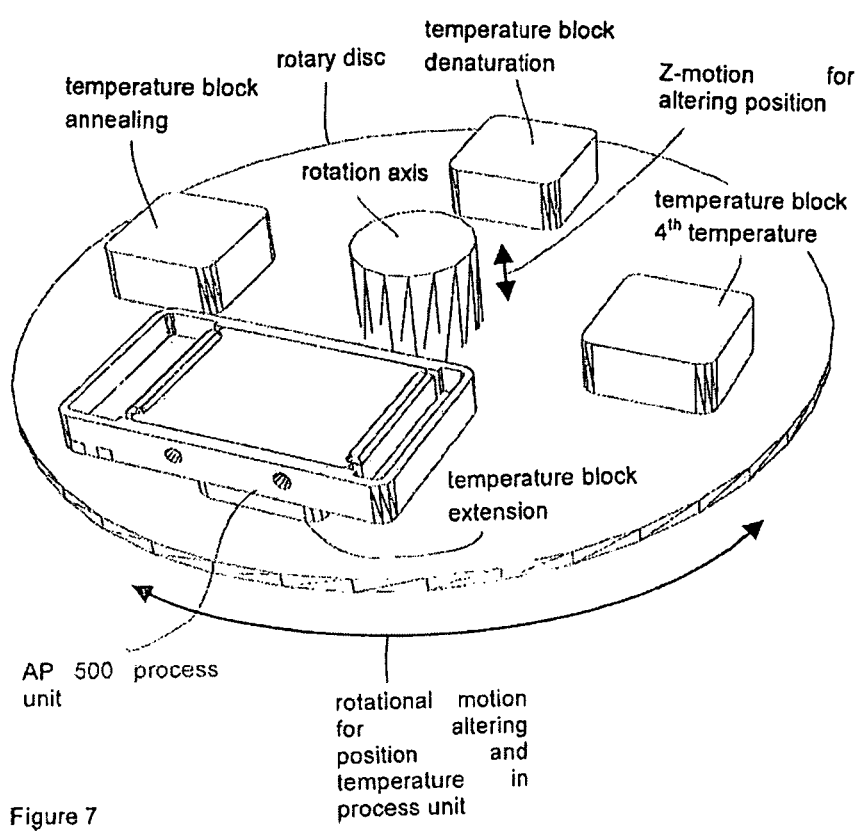
FIG. 7 is a diagram depicting a view of a rotary disc, whereon four temperature blocks are installed. The temperature blocks are thermostatted to one temperature each. By means of rotating the disc and/or the process unit, the temperature in the reaction chamber can be altered.

Heat transfer between the temperature blocks of the temperature controlling and regulating unit is preferably ensured in that the temperature blocks contact the first surface and/or second surface of the device according to the present invention. Preferably, the temperature blocks can be arranged linearly or on a rotary disc and, for example, be integrated in the detection device in this manner. FIG. 7 shows a rotary disc having several temperature blocks, each of which is adjusted to a defined temperature. By means of exchanging the temperature blocks below the process unit, the process unit is brought to a specific temperature defined by the temperature block. Preferably, the temperature blocks are manufactured in such a way, that they have a significantly higher heat capacity than the process unit, so that maximal temperature alteration speeds of, for example, at least 5 K/s are also practicable in this embodiment. Preferably, the temperature blocks are only thermostaticized instead of heated or cooled, so that the energy demand is also minimal in this case. In this embodiment, cooling or heating the process unit can be omitted.

In a further embodiment, the temperature controlling and regulating unit is integrated in the means for guiding the first surface and/or in the means for agitating, and/or in the spacer. In this embodiment, heat transfer is conducted by means of contacting the means and/or the spacer with the first surface and/or the second surface.

Preferably, the device additionally comprises a reprocessing unit for purifying and/or re-concentrating the sample solution and/or for controlling the loading and unloading of the reaction chamber with fluids. Within the scope of the present invention, fluids are understood to denote liquids and gases. Furthermore, the analysis solution can be re-buffered in the reprocessing unit. The reprocessing unit can finally also be used for providing the necessary analysis chemicals. The connection of the fluid containers with the reaction chamber can, for example, be developed as described in the International Patent Application WO 01/02094.

In this embodiment, the reaction chamber and the reprocessing unit are particularly preferably connected via two cannulas, wherein the cannulas are arranged in such a way that a first cannula ensures the feeding of fluids from the reprocessing unit into the reaction chamber and a second cannula ensures the escape of air dislocated by the fed fluids from the reaction chamber. A sample fed into the reprocessing unit can thus reach the reaction chamber of the process unit via the cannulas. To this end, the cannulas are arranged in such a way that they reach into the reaction chamber via the cannula guide.

The reprocessing unit can be developed in such a way that it can be separated from the process unit. After filling the reaction chamber with the sample solution and, optionally, with further reaction liquids, the reprocessing unit can thus be separated from the process unit, preferably be disengaged, and, optionally, be discarded.

All preceding embodiments optionally have a displacement structure located on the second surface, as described above, namely on the side of the second surface that is facing the microarray. Thereby, the displacement structure is positioned in such a way that it is located opposite to the microarray and evenly rests on it in the compressed state, wherein during compression the analyte solution being is substantially displaced from the reaction chamber and the surface of the microarray, respectively.

In the following, embodiments of integrated or non-integrated units for filling the reaction chamber, which will also be referred to in the following as filling unit or reprocessing unit, will be described. These embodiments may have the above-mentioned displacements structures located on the second surface.

Conventionally, the reaction solution is brought into a specific opening of the filling unit by means of a suitable tool, for example, a pipette. The transport of liquids into the device is performed via the pressure exerted by the pipette or by means of another pressure-generating tool, like for example a syringe or an automated unit, which is, for example, a functional component of a processing automat.

Preferably, the filling unit is developed for manual operation in an ergonomically suitable way. Furthermore, it preferably has easily accessible additional openings at the outsides for feeding the reactive substances.

Preferably, a filling unit furthermore has a suitable fluid interface for penetrating the seal of the chamber body. To this end, specific cannulas are used, which, for example, consist of high-grade steel or polymers and usually have a diameter of 0.05 mm to 2 mm. Preferably, at least one or more cannulas are arranged, particularly preferably two, wherein one can be used for filling with a reactive liquid and another for ventilation of the reaction space and for taking up surplus fluids. Such cannulas can be connected with the filling unit in a fixed or an interchangeable manner, wherein preferably a connection, which cannot be detached by the operator, for implementing disposable filling items is implemented.

The filling unit can furthermore comprise a unit for covering the cannulas, so that any possible injury of the operator or contamination of the environment can be avoided after separation of the systems.

Preferably, the filling unit furthermore comprises a suitable mechanical interface for snug-fit contacting of the reaction cartridge. Said interface can be developed, for example, in the form of specific snaps. In this manner, penetration of the seal of the chamber body at preferred sites can be ensured.

When processing the reaction cartridge in corresponding processing automats, suitable mechanical measures are to be taken, which allow adjustment and accurate positioning in the devices. This particularly applies to the positioning for the replacement and/or the feeding of liquids and the positioning of the reaction cartridge for detection of the signals after conduction of the reactions in the reaction chamber.

The device or the filling unit can furthermore comprise an integrated waste container, which serves for taking up surplus or dislocated gaseous or liquid media, like for example protective gas fillings or buffers. The waste container can, for example, be filled with a further gaseous, liquid, or solid medium, which binds the liquid or gaseous substances reversibly or irreversibly, like for example cellulose, filter materials, silica gels. In addition, the waste container can have a ventilation opening or can exhibit a negative pressure for improving the filling behavior of the entire unit.

Alternatively, the waste container can also be developed as separate module. In this case, the filling unit is equipped with corresponding fluid interfaces which can correspond to commercial standards, like for example LuerLock, and which lead to the outside. Such interfaces can have a form or force connection with continuing systems.

Figure 22:
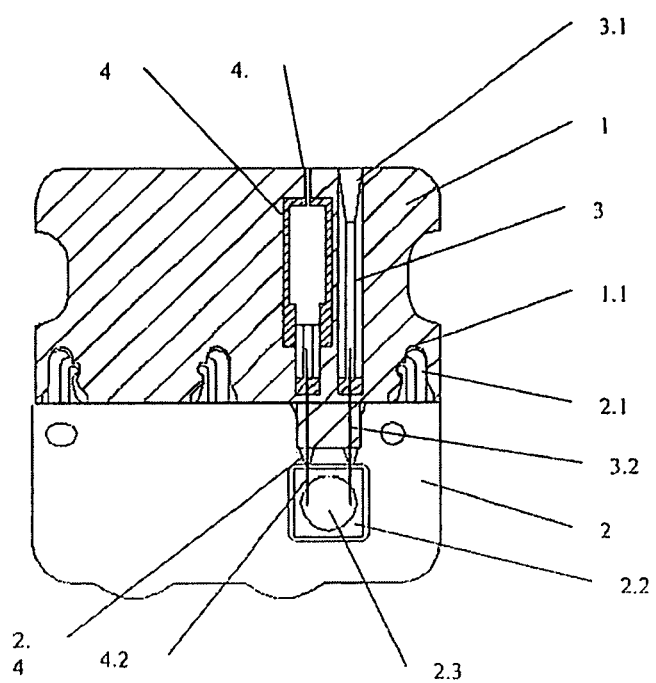
FIG. 22 is a diagram depicting a schematic view of a detachable filling unit for filling reaction cartridges with reactive substances or buffers. The following reference numbers are used.

In a first special embodiment, filling is conducted by means of a detachable filling unit having an integrated waste container. In particular, the filling unit serves for non-recurrent filling of the reaction chamber. The filling unit is, for example, developed in such a way that it is plugged or temporarily attached to the cartridge, the samples are fed into the reaction space, and, after filling is completed, the filling unit is again separated from the cartridge and is discarded. In this special first embodiment, the filling unit further comprises an integrated waste container, which can be developed as described above. An example for this embodiment is shown in FIG. 22. The procedure for filling a reaction cartridge by means of a modular filling unit is shown in FIG. 23.

In a second special embodiment, filling is conducted by means of an integrated filling unit. Herein, the filling unit is an integrated component of the reaction cartridge and is therefore not separated from the latter; discarding the filling unit and the cartridge is conducted simultaneously. Herein, the filling unit is preferably used for non-recurrent filling of the reaction chamber and possibly for further process-internal fluid steps. In this embodiment, the filling unit furthermore preferably comprises a technical device, which implements a preferred position of the cannulas in the system, in particular for preventing inadvertent piercing of the cannulas into the seal of the chamber body. It is, however, also conceivable that the cannulas pierce the seal of the chamber body in said preferred position. Said technical device can, for example, be implemented by means of establishing springs, elastic elements, or specific recesses and bumps for implementing a catch. In this embodiment, the filling unit further comprises a filling and waste channel, which comprises corresponding fluid interfaces, which can also correspond to commercial standards, like for example LuerLock, and which lead to the outside. Such interfaces can have a positive or non-positive interlocking with continuing systems and serve for feeding and/or removing gaseous and/or liquid media. An example for this embodiment is shown in FIG. 24. The procedure for filling a reaction cartridge having an integrated filling unit is shown in FIG. 25.

In a third special embodiment, filling is conducted via an integrated filling unit having an integrated waste container. In said embodiment, the filling unit is an integrated component of the reaction cartridge and is therefore not separated from the latter; filling unit and cartridge are discarded simultaneously. Herein, the filling unit is preferably used for non-recurrent filling of the reaction chamber and possibly for further process-internal fluid steps.

In this embodiment, the filling unit furthermore preferably also comprises a technical device, which implements a preferred position of the cannulas in the system, preferably for preventing inadvertent piercing of the cannulas into the seal of the chamber body. It is, however, also conceivable that the cannulas pierce the seal of the chamber body in said preferred position. Said technical device can, for example, be implemented by means of establishing springs, elastic elements, or specific recesses and bumps for implementing a catch. In this embodiment, the filling unit furthermore comprises an integrated waste container, which can be developed as described above. An example for this embodiment is shown in FIG. 26. The procedure for filling a reaction cartridge with an integrated filling unit and integrated waste container can, for example, be conducted by means of combining the procedures described in FIGS. 23 and 25.

In the following, a special embodiment for arranging cannulas for pressure balance during the compression procedure will be described. The cannulas of a filling tool for the cartridge can, for example, be arranged in such a way that both filling in a non-compressed state and transfer of surplus reaction solutions during a compression of the reaction space is possible. This can preferably be achieved by means of adapted construction of the seal and a cannula arrangement, wherein the cannulas preferably pierce the compensation regions within the reaction chamber. Such an arrangement is particularly suitable, if the surplus volume cannot be taken up by means of a special seal design. An example for a possible vertical cannula arrangement with unaltered form of the seal is shown in FIG. 27.

The device according to the present invention can further comprise a unit, which is connected to the detection system, for controlling the test procedure and/or for processing the signals recorded by means of the detection system. The controlling and/or processing unit can be a micro-controller or an industrial computer. This coupling of detection unit and processing unit, which ensures the conversion of the reaction results to the analysis result, allows, inter alia, the use of the device according to the present invention as hand-held device, for example, in medical diagnostics.

In addition, the device according to the present invention furthermore preferably has an interface for external computers. Inter alia, this allows the transfer of data for external storage.

In a further preferred embodiment, the device is equipped with a coding, preferably a data matrix and/or a bar code, containing information on the substance library and/or the conduction of the amplification and/or detection reaction. By means of such an individual identification number, the reading or detection device can automatically recognize, which test has been conducted. To this end, a data record containing information on the substance library, the conduction of the detection reaction, and the like is stored in a database when manufacturing the device according to the present invention. Thus, the data record can, in particular, contain information on the layout of the probes on the array and information as to how evaluation is to be conducted in the most advantageous manner. The data record or the data matrix can further contain information on the temperature-time regime of a PCR to be optionally conducted for amplifying the target molecules. The data record thus obtained is preferably given a number, which is attached to the holder in the form of the data matrix. Via the number recorded in the data matrix, the set data record can then optionally be called when reading out the substance library. Finally, the data matrix can be read out by the temperature controlling or regulating unit and other controllers, like for example a control for filling and unloading of the reaction chamber via the fluid containers, and an automatic conduction of amplification and detection reaction can thus be ensured.

The coding, like a data matrix, does not compellingly have to contain the entire information. It can also simply contain an identification or access number, by means of which the necessary data are then downloaded from a computer or a data carrier.

All preceding embodiments optionally have a displacement structure located on the second surface, as described above, namely on the side of the second surface that is facing the microarray. Thereby, the displacement structure is positioned in such a way that it is located opposite to the microarray and evenly rests on it in the compressed state, wherein during compression the analyte solution being is substantially displaced from the reaction chamber and the surface of the microarray, respectively.

Figure 10:
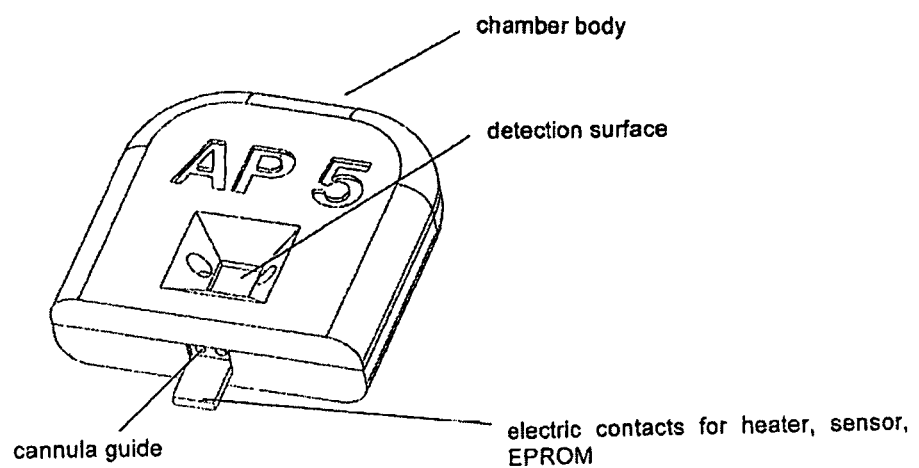
FIG. 10 is a diagram depicting a view of a process unit according to the present invention having a circuit board as electric connection for heater and temperature sensor. The heater is developed as a semiconductor component.
Figure 11:
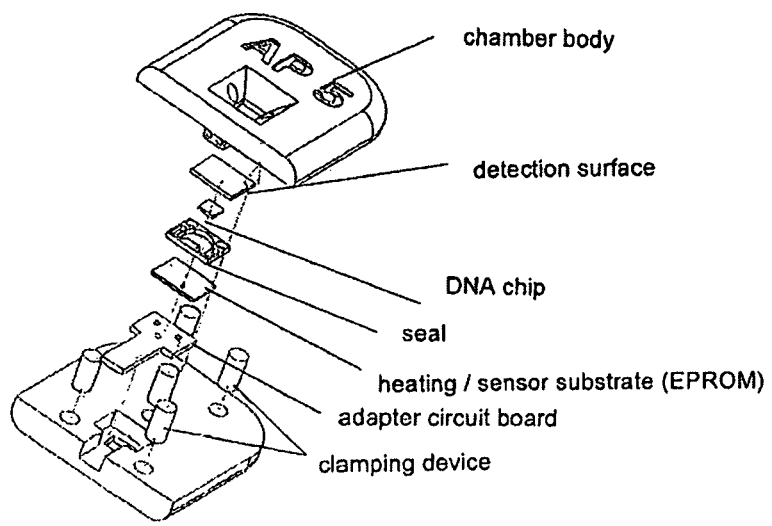
FIG. 11 is a diagram depicting an exploded view of the process unit shown in FIG. 10.

The device according to the present invention can be very easily manufactured. In FIG. 3 it is shown that the process unit can consist of only four individual components, which are simply fit into one another. FIGS. 10 and 11 show embodiments, which can also be easily manufactured due to the construction according to the present invention, although they consist of several components. The geometric tolerances of the dimensions of the individual components can be very large with, for example, $1/10$ to $2/10$ mm, so that, for example, the large-scale injection molding of seal and chamber body can be conducted in a very cost-efficient manner. The low tolerances are facilitated by means of pressing the chip against the detection plane, as thereby the optical path to the detection microscope is hardly influenced by the components of the process unit. The only geometric quantities having a low tolerance are the x,y-position of the chip and the thickness of the detection plane. The variance of the z-position of the chip, however, only plays a subordinate part. Despite these low technical requirements, a focusing device at the optical system, for example a fluorescence detection microscope, is not required. These properties clearly show the suitability of the device according to the present invention for mobile on-site use. The preceding advantages also apply, if the devices have the above-mentioned displacement structure.

In a further aspect of the present invention, a method for qualitatively and/or quantitatively detecting molecular interactions between probe and target molecules is provided, which comprises the following steps:

a) introducing a sample, preferably a sample solution comprising target molecules, into a reaction chamber of a device according to the present invention as described above; and b) detecting an interaction between the target molecules and the probe molecules immobilized on the substrate.

The method according to the present invention allows the qualitative and/or quantitative detection of molecular interactions between probe and target molecules in a reaction chamber, without necessitating a replacement of the sample or reaction liquids in order to remove a disturbing background after the interaction is completed and before the detection.

Within the scope of the present invention, the detection of an interaction between the probe and the target molecule is usually conducted as follows: Subsequently to fixing the probe or the probes to a specific matrix in the form of a microarray in a predetermined manner or subsequently to providing a microarray, the targets are contacted with the probes in a solution and are incubated under defined conditions. As a result of the incubation, a specific interaction or hybridization occurs between probe and target. The bond occurring herein is significantly more stable than the bond of target molecules to probes, which are not specific for the target molecule.

The detection of the specific interaction between a target and its probe can be performed by means of a variety of methods, which normally depend on the type of the marker, which has been inserted into target molecules before, during or after the interaction of the target molecule with the microarray. Typically, such markers are fluorescent groups, so that specific target/probe interactions can be read out fluorescence-optically with high local resolution and, compared to other conventional detection methods, in particular mass-sensitive methods, with little effort (see, for example, A. Marshall, J. Hodgson, DNA chips: An array of possibilities, Nature Biotechnology 1998, 16, 27-31; G. Ramsay, DNA Chips: State of the art, Nature Biotechnology 1998, 16, 40-44).

Depending on the substance library immobilized on the microarray and the chemical nature of the target molecules, interactions between nucleic acids and nucleic acids, between proteins and proteins, and between nucleic acids and proteins can be examined by means of this test principle (for survey see F. Lottspeich, H. Zorbas, 1998, Bioanalytik, Spektrum Akademischer Verlag, Heidelberg/Berlin, Germany).

Herein, substance libraries, receptor libraries, peptide libraries, and nucleic acid libraries are considered as substance libraries, which can be immobilized on microarrays or chips. The nucleic acid libraries take by far the most important role, and include microarrays, on which deoxyribonucleic acid (DNA) molecules or ribonucleic acid (RNA) molecules are immobilized.

In a preferred embodiment of the method according to the present invention, before detection the distance between first and second surface is kept in a position, which allows processing of the sample solution and/or the interaction between the target molecules and the probe molecules immobilized on the substrate, for example amplification of nucleic acids to be detected and/or hybridization between nucleic acids to be detected and the nucleic acid probes immobilized on the substrate, before detection in step b).

It is further preferred that in step b) the distance between the first and the second surface is altered, preferably reduced. I.e. the detection is preferably conducted with a reduced distance between at least one area of the first surface, on which the detection has to take place and the probes can be immobilized, respectively, and detection plane. Particularly preferably, the distance between first surface and detection plane is about zero during detection.

In one embodiment, the microarray is guided towards the second surface in order to reduce the distance between first and second surface. Preferably, this is ensured by pressing the first surface by applying pressure exerted via at least one means for guiding the first surface, for example a tappet, a rod, a pin and/or a screw, wherein the pressure point of the means is located particularly below the microarray.

Pressing the first surface against the second surface or the detection plane can be facilitated in that the first surface is elastically deformable at least in the region below the region onto which probes can be immobilized or the detection of the targets can take place. Alternatively, the first surface can be developed by means of two superimposed layers, wherein one outer layer of the two superimposed layers has a recess at least in the region below the region, onto which the probes can be immobilized or the detection of the targets can take place, and an inner layer of the two superimposed layers is formed by an elastic seal. Pressure is then exerted on the inner layer in the vicinity of the recess by the means for guiding the first surface.

The means for guiding the first surface, for example a pin, a rod, a tappet and/or a screw, cannot only serve for exerting a pressure on the first surface, however. In the event that bubbles should form on the DNA chip, which would impede the detection, these bubbles can be removed by means of agitation by the means for guiding the first surface, for example by means of a vibration frequency of about 20 Hz applied to the first surface, in particular in the form of an elastic membrane.

All preceding embodiments optionally have a displacement structure located on the second surface, as described above, namely on the side of the second surface that is facing the microarray. Thereby, the displacement structure is positioned in such a way that it is located opposite to the microarray and evenly rests on it in the compressed state, wherein during compression the analyte solution being is substantially displaced from the reaction chamber and the surface of the microarray, respectively.

Furthermore, there is often the problem that the interaction, for example the hybridization, at the chip surface takes a very long time. Among other reasons, this is due to the fact that the speed of interaction or hybridization is determined by diffusion. Preferably, the interaction or hybridization speed can be increased by means of agitation via the means for guiding the first surface, for example by means of a vibration frequency of about 20 Hz applied to the first surface, in particular in the form of an elastic membrane, as the agitation or vibration leads to mixing in the reaction chamber.

In a further embodiment, the second surface is guided towards the first surface in order to reduce the distance between the first and the second surface. In particular, this can be ensured in that the second surface is guided toward the first surface by means of pressure exerted on the second surface by the spacer.

In a further embodiment, the first surface is guided towards the second surface and the second surface is guided towards the first surface in order to reduce the distance between the first and the second surface. In all preceding embodiments, the above-described displacement structures may be present.

In the following, further embodiments for guiding the first surface relatively to the second surface or the second surface relatively to the first surface will be described. Said embodiments are not only suitable for positioning the first surface or the region, onto which probes can be immobilized or the detection of the targets can take place, relatively to the second surface or the detection surface, but can, in particular, also be used for moving the probe array relatively to the detection surface. By means of such a motion, for example an agitation of the solution in the reaction chamber can be achieved.

In one embodiment, the substrate, whereon probes can be immobilized or which represents the region where the detection of the targets is supposed to take place, and which, in this case, is not integrated in the first surface, is moved relative to the detection surface or moved within the chamber by means of a magnetic field. The substrate and/or the second surface, for example, contain a magnetic material or a component, whereto a magnetic material has been added, and/or is mounted in a holder consisting of an entirely or partially magnetic material. It can further be preferred that the substrate and/or the second surface are moved passively by moving a magnetic body, which is arranged below the respective surface and is, for example, connected with said surface, by means of a magnetic field.

In a further embodiment, the substrate is moved and/or positioned relatively to the detection surface by means of gravitational impact.

In a further embodiment, the substrate is moved and/or positioned relatively to the detection surface by means of a stream generated in the reaction chamber. To this end, the device can, for example, be developed in such a way that, in case the probe array is surrounded by a liquid stream, a negative pressure is generated at one side of the reaction chamber and a positive pressure is generated at the opposite side, which leads to movement of the substrate in the reaction chamber. Such a stream can, for example, be implemented by means of thermal convection, which is caused by local temperature differences in the chamber.

In a further embodiment, the substrate is moved and/or positioned relatively to the detection surface by means of impact of an electric field.

In a further embodiment, a gas bubble is generated below the probe array by means of local overheating, due to which the substrate is moved in the chamber or is guided toward the detection surface. In the preceding embodiments, the above-mentioned displacement structures may be present as well.

By means of reducing the distance between first and second surface before the detection, the sample solution preferably is substantially entirely removed from the region between first surface and at least the region of the first surface, onto which, for example, probes can be immobilized either on the first surface or a substrate, and on which detection has to take place, and detection plane. Hereby, background signals, which are caused by labeled molecules, which are not bound to the array surface, for example by labeled primers and/or labeled target nucleic acids, which are not bound to the array surface, are reduced.

Thus, in the detection of step b), the distance between the first and the second surface is preferably altered in such a way that the sample solution between the first and the second surface is essentially removed. The target-probe-complexes to be detected are then essentially either located in increased concentration in the detection plane due to immobilized probes or the size of the target-probe-complexes and a disturbing background is virtually avoided. This also applies in the presence of a displacement structure.

In a further alternative embodiment, the first surface rests evenly on the second surface forming the detection plane already in the original state of the device and is not only brought into the detection plane by means of guiding the first surface toward the second surface and/or guiding the second surface toward the first surface. In this embodiment, the first surface is not moistened by the sample solution during the processing steps. For conducting the interaction reaction, for example a hybridization, the first surface, which is preferably made of an elastic material, for example an elastic membrane, is guided away from the detection surface. Thereby, the chip surface is moved away from the detection surface and is moistened by the sample solution. The interaction, for example a hybridization, can take place. For conducting the detection and further processing, the first surface, for example in the form of an elastic membrane, is released again, due to which it leaps back to its originally adjusted position, which can be accelerated by means of pressure exerted by a means for guiding the first surface, for example a pin, a rod, a screw and/or a tappet. Thereby, the first surface is pressed towards the detection plane again and the detection can be conducted without having background. This also applies in the presence of a displacement structure.

In a further embodiment of the method according to the present invention, a device according to the present invention, as described above, is used, the first surface of which is developed in a pivotable manner around a rotation axis.

In a first position, which is also referred to as initial position, the surface of the region, onto which for example probes can directly be immobilized on a first surface or on a substrate and on which the targets have to be detected (e.g., a microarray), rests essentially evenly on the second surface, i.e. the substrate surface with the probe molecules immobilized thereon is essentially not moistened by the sample solution. In the space formed in the first position between the second flanking portion of the first surface and the second surface, the processing chamber, the processing of the reaction solution is preferably conducted, i.e. in particular purification, re-concentration, washing and rinsing and/or amplification steps.

Subsequently, the pivotable first surface is brought to a second position, wherein the first surface is arranged relatively to the second surface at an angle other than 180°, preferably at an angle of 45°. Preferably, this is conducted by means of traction exerted on the first flanking portion of the first surface and/or pressure exerted on the second flanking portion of the first surface by means of a means for guiding the first surface, as described above. By means of guiding the first surface to the second position, the microarray is guided away from the second surface and the sample solution penetrates the cavity forming between microarray and second surface. The probe molecules immobilized on the substrate of the microarray are freely accessible for the target molecules present in the sample solution, so that an interaction reaction between probe and target molecules can occur. In this embodiment of the method according to the present invention, pressure and/or traction exerted on the first surface has the advantage that, in this manner, the sample solution is moved and thus the interaction reaction can be accelerated.

For conducting the detection and, optionally, further processing, the pivotable first surface is guided back to the first position, for example by means of pressure exerted on the first flanking portion of the first surface and/or traction exerted on the second flanking portion of the first surface or, in the case of elastic development of the first surface, by means of releasing the first flanking portion. Now, the mentioned region of the first surface again rests essentially evenly on the second surface, so that the sample solution between the second surface and the microarray is essentially displaced in this position and an essentially background-free detection can take place. The preceding embodiment may also comprise a displacement structure.

The targets to be examined can be present in any kind of sample, preferably in a biological sample.

Preferably, the targets are isolated, purified, copied, and/or amplified before their detection and quantification by means of the method according to the present invention.

The method according to the present invention further allows the amplification and the qualitative and/or quantitative detection of nucleic acids in a reaction chamber, wherein the detection of molecular interactions or hybridizations can be conducted after completion of a cyclic amplification reaction without necessitating replacement of the sample or reaction liquids. The method according to the present invention further also ensures a cyclic detection of hybridization events in an amplification, i.e. a detection of the hybridization even during the cyclic amplification reaction. Finally, with the aid of the method according to the present invention, the amplification products can be quantified during the amplification reaction and after completion of the amplification reaction.

Usually, the amplification is performed by means of conventional PCR methods or by means of a method for the parallel performance of amplification of the target molecules to be analyzed by means of PCR and detection by means of hybridization of the target molecules with the substance library support, as is described above.

In a further embodiment, the amplification is performed as a multiplex PCR in a two-step process (see also WO 97/45559). In a first step, a multiplex PCR is performed by means of using fusion primers, whose 3'-ends are gene specific and whose 5'-ends represent a universal region. The latter is the same in all forward and reverse primers used in the multiplex reaction. In this first stage, the amount of primer is limiting. Hereby, all multiplex products can be amplified until a uniform molar level is achieved, given that the number of cycles is adequate for reaching primer limitation for all products. In a second stage, universal primers identical to the 5'-regions of the fusion primers are present. Amplification is performed until the desired amount of DNA is obtained.

In a further preferred embodiment of the method according to the present invention, detection is performed during the cyclic amplification reaction and/or after completion of the cyclic amplification reaction. Preferably, detection is performed during the amplification reaction, in every amplification cycle. Alternatively, detection can also be determined in every second cycle or every third cycle or in any arbitrary intervals.

In the conduction of a linear amplification reaction, wherein the target amount increases by a certain amount with each step, or an exponential amplification reaction, for example a PCR, wherein the DNA target amount multiplies with each step, in the process unit, the chip can thus be pressed towards the detection plane after every amplification step and therefore the detection can be conducted. It is thus possible to perform on-line surveillance of the amplification reaction. In particular in the case of non-linear amplification reactions, it is thereby possible to determine the initial concentration of the DNA target amount. In the case of protein-targets and -probes, for example, binding kinetics can be detected in an analogous manner as already mentioned above.

In this manner, the number of amplification steps can furthermore be optimized on-line. As soon as the DNA target amount has reached a specific concentration, the amplification is discontinued. If the initial target concentration is low, the number of amplification steps is increased in order to be able to conduct an assured analysis of the products. In the case of reduced reaction time of positive controls, the analysis process can be discontinued very early.

The chemicals necessary for conducting an amplification reaction, like for example polymerase, buffer, magnesium chloride, primers, labeled, in particular fluorescence-labeled primers, dNTPs and the like, can be provided in the reaction chamber, for example in freeze-dried form.

Preferably, the cyclic amplification reaction is a PCR. In a PCR, three temperatures for each PCR cycle are usually passed through. Preferably, the hybridized nucleic acids detach from the microarray at the highest temperature, i.e. the denaturation temperature. A preferred value for the denaturation temperature is 95° C. Therefore, a hybridization signal, which serves as zero value or reference value for the nucleic acids detected in the respective PCR cycle, can be determined at this denaturation temperature.

At the temperature following in the PCR cycle, an annealing temperature of, for example, about 60° C., a hybridization between the nucleic acids to be detected and the nucleic acids immobilized on the substrate of the microarray is facilitated. Therefore, in one embodiment of the method according to the present invention, the detection of target nucleic acids present in a PCR cycle is performed at the annealing temperature.

In order to enhance the sensitivity of the method according to the present invention, it can further be advantageous to lower the temperature below the annealing temperature, so that the detection is preferably performed at a temperature below the annealing temperature of an amplification cycle. For example, the detection can be performed at a temperature in a range of 25° C. to 50° C. and preferably in a range of 30° C. to 45° C.

In a further alternative embodiment of the method according to the present invention, the hybridization between nucleic acids to be detected and the nucleic acids immobilized on the substrate of the microarray is at first performed at a low temperature, in order to subsequently raise the hybridization temperature. Such an embodiment has the advantage that the hybridization time is reduced compared to hybridizations at temperatures of more than 50° C. without losing specificity in the interactions.

If the zero value or reference value determined at denaturation temperature is subtracted from the measured value determined at or below the annealing temperature, a measured result free of disturbances, in which fluctuation and drift are eliminated, can be obtained.

Usually, the target molecules to be detected are equipped with a detectable marker. In the method according to the present invention, the detection is thus preferably conducted by means of equipping the bound targets with at least one label, which is detected in step b).

As already mentioned above, the label coupled to the targets or probes preferably is a detectable unit or a detectable unit coupled to the targets or probes via an anchor group. With respect to the possibilities for detection or labeling, the method according to the present invention is very flexible. Thus, the method according to the present invention is compatible with a variety of physical, chemical, or biochemical detection methods. The only prerequisite is that the unit or structure to be detected can directly be coupled or can be linked via an anchor group, which can be coupled with the oligonucleotide, to a probe or a target, for example an oligonucleotide.

The detection of the label can be based on fluorescence, magnetism, charge, mass, affinity, enzymatic activity, reactivity, a gold label, and the like. Thus, the label can, for example, be based on the use of fluorophore-labeled structures or components. In connection with fluorescence detection, the label can be an arbitrary dye, which can be coupled to targets or probes during or after their synthesis. Examples are Cy dyes (Amersham Pharmacia Biotech, Uppsala, Sweden), Alexa dyes, Texas Red, Fluorescein, Rhodamin (Molecular Probes, Eugene, Oreg., USA), lanthanides like samarium, ytterbium, and europium (EG&G, Wallac, Freiburg, Germany).

Particularly preferably, said detectable marker is a fluorescence marker. As already mentioned above, the use of the device according to the present invention in the method according to the present invention ensures the detection of the fluorescence markers by means of a fluorescence microscope without autofocus, for example a fluorescence microscope with fixed focus.

Apart from fluorescence markers, luminescence markers, metal markers, enzyme markers, radioactive markers, and/or polymeric markers can also be used within the scope of the present invention as labeling and/or detection unit, which is coupled to the targets or the probes.

Likewise, a nucleic acid, which can be detected by means of hybridization with a labeled reporter (sandwich hybridization), can be used as label (tag). Diverse molecular biological detection reactions like primer extension, ligation, and RCA are used for the detection of the tag.

In an alternative embodiment of the method according to the present invention, the detectable unit is coupled with the targets or probes via an anchor group. Preferably used anchor groups are biotin, digoxigenin, and the like. In a subsequent reaction, the anchor group is converted by means of specifically binding components, for example streptavidin conjugates or antibody conjugates, which in turn are detectable or trigger a detectable reaction. With the use of anchor groups, the conversion of the anchor groups to detectable units can be performed before, during, or after the addition of the sample comprising the targets, or, optionally, before, during, or after the cleavage of a selectively cleavable bond in the probes.

Such selectively cleavable bonds in the probes are, for example, described in the International Patent Application WO 03/018838, the relevant contents of which are hereby explicitly referred to.

According to the present invention, labeling can also be performed by means of interaction of a labeled molecule with the probe molecules. For example, labeling can be performed by means of hybridization of an oligonucleotide labeled as described above with an oligonucleotide probe or an oligonucleotide target.

Further labeling methods and detection systems suitable within the scope of the present invention are described, for example, in Lottspeich and Zorbas, Bioanalytik, Spektrum Akademischer Verlag, Heidelberg, Berlin, Germany 1998, chapter 23.3 and 23.4.

In a preferred embodiment of the method according to the present invention, detection methods are used, which in result yield an adduct having a particular solubility product, which leads to a precipitation. For labeling, in particular substrates or educts are used, which can be converted to a hardly soluble, usually stained product. In this labeling reaction, for example, enzymes can be used, which catalyze the conversion of a substrate to a hardly soluble product. Reactions suitable for leading to a precipitation at the array elements as well as possibilities for the detection of the precipitation are, for example, described in the International Patent Application WO 00/72018 and in the International Patent Application WO 02/02810, whose relevant contents are hereby explicitly referred to.

In a particularly preferred embodiment of the method according to the present invention, the bound targets are equipped with a label catalyzing the reaction of a soluble substrate or educt to form a hardly soluble precipitation at the array element, where a probe/target interaction has occurred or acting as a crystal nucleus for the conversion of a soluble substrate or educt to a hardly soluble precipitation at the array element, where a probe/target interaction has occurred.

In this manner, the use of the method according to the present invention allows for the simultaneous qualitative and quantitative analysis of a variety of probe/target interactions, wherein several array elements having a size of ≤1000 µm, preferably of ≤100 µm, and particularly preferably of ≤50 µm may be realized.

The use of enzymatic labels is known in immunocytochemistry and in immunological tests based on microtiter plates (see E. Lidell and I. Weeks, Antibody Technology, BIOS Scientific Publishers Limited, 1995). Thus, for example, enzymes catalyze the conversion of a substrate to a hardly soluble, usually stained product.

Particularly preferably, the reaction leading to precipitation formation at the array elements is a conversion of a soluble substrate or educt to a hardly soluble product, catalyzed by an enzyme. In a special embodiment, the reaction leading to precipitation formation at the array elements is an oxidation of 3,3',5,5'-tetramethylbenzidine, catalyzed by a peroxidase.

Preferably, horseradish peroxidase is used for the oxidation of 3,3',5,5'-tetramethylbenzidine. However, additional peroxidases are known by the skilled person, which can be used for the oxidation of 3,3',5,5'-tetramethylbenzidine.

3,3',5,5'-tetramethylbenzidine, when exposed to a peroxidase, is assumed to be oxidized in a first step to form a blue-stained radical cation (see, for example, Gallati and Pracht, J. Clin. Chem. Clin. Biochem. 1985, 23, 8, 454). This blue-stained radical cation is precipitated in form of a complex by using a polyanion, such as dextran sulfate. The precipitation reaction by means of peroxidase-catalyzed oxidation of 3,3',5,5'-tetramethylbenzidine is, for example, described in EP 0 456 782.

Without any intention of being complete, the following Table 1 summarizes several reactions that are suitable to cause a precipitation at array elements, where an interaction between target and probe has occurred:

TABLE 1

| catalyst or crystal nucleus | substrate or educt |
|---|---|
| horseradish peroxidase | DAB (3,3'-diaminobenzidine) |
|  | 4-CN (4-chloro-1-naphthol) |
|  | AEC (3-amino-9-ethylcarbazole) |
|  | HYR (p-phenylenediamine-HCl and pyrocatechol) |
|  | TMB (3,3',5,5'-tetramethylbenzidine) |
|  | naphthol/pyronin |
| alkaline phosphatase | brom-chlor-indolyl-phosphate (BCIP) and nitroblue tetrazolium (NBT) |
| glucose oxidase | t-NBT and m-PMS (nitroblue tetrazolium chloride and phenazine methosulfate |
| gold particles | silver nitrate |
|  | silver tartrate |

In particular, the detection of probe/target interactions via insoluble precipitates is described in WO 02/02810.

In the following, embodiments of the present invention are described, which can serve to overcome problems likely to arise in the detection of molecular interactions on solid supports, such as for preventing the possible formation of Newton's rings between detection surface and probe array.

The manifestation of Newton's rings is essentially determined by the type of illumination, the wavelength of the light used for detection, the distance between detection plane and probe array, and the refraction index of the solution located in the chamber. Such Newton's rings can, for example, be prevented by means of altering the wavelength of the light used for detection, by using a solution having the same or a similar refraction index as the detection surface and/or the probe array, and/or by using an immersion liquid between detection surface and probe array.

Furthermore, Newton's rings can be prevented by means of applying spacers on the chip or on the regions on the side of the detection surface facing the chip.

Furthermore, Newton's rings can be prevented by means of applying the probe array onto a rough support surface.

Furthermore, Newton's rings can be prevented by means of applying the probe array onto a light-absorbing surface.

As a further possibility the contact pressure by which the first surface is guided relatively to the detection surface may be permanently varied during detection. Thus, the thickness of the gap between chip and detection surface, and therefore also the position of Newton's rings, is altered. By integrating the fluorescence signal to be detected over time, a falsification of the measured values of the spots in relation to each other is prevented.

It is a further particularly preferably possibility of preventing Newton's rings to use several light sources from different directions for illuminating and therefore agitating the fluorophores of the bound targets.

Background fluorescence caused by fluorophores of unbound targets in the displaced liquid can lead to distortion of the signal detected. This can preferably be prevented by means of using an aperture, which is, for example, mounted on the detection surface or the chip and/or the regions around the chip or the imaging optics, and is configured in such a way that only the surface of the probe array is illuminated or imaged.

By using appropriate light sources, such as lasers, illumination may be inhomogenous due to coherence of the light. Such inhomogeneities can be reduced or prevented by using waveguides and/or combining filters and/or light of different wavelengths. Likewise, movement of the light source in order to eliminate such effects is also conceivable.

By using an organic or inorganic light-absorbing layer, which is non-fluorescent in the selected wavelength range, on the substrate of the probe array, the fluorescence background signal caused by the array support and/or elements located behind the same, can be reduced or prevented. Preferably, a black chromium layer is employed as protective layer.

In all above-described embodiments of the inventive method, a pre-amplification of the material to be analyzed is not required. From the sample material extracted from bacteria, blood, or other cells, specific partitions can be amplified using a PCR (polymerase chain reaction), in particular in the presence of the inventive device or the substance library support, as is described in DE 102 53 966, and hybridized to the support. This represents a substantial reduction of labor effort.

Thus, the method according to the present invention is particularly suitable for the parallel amplification of the target molecules to be analyzed by PCR and the detection by hybridization of the target molecules with the substance library support. There, the nucleic acid to be detected is first amplified by PCR, wherein preferably at least one competitor inhibiting the formation of one of the two template strands amplified by PCR is initially added to the reaction. In particular, a DNA molecule, which competes with one of the primers used for the PCR amplification of the template for binding to the template and which can not be extended enzymatically, is added to the PCR. The single-stranded nucleic acid molecules amplified by PCR are then detected by means of hybridization with a complementary probe. Alternatively, the nucleic acid to be detected is first amplified using a surplus of single strand by PCR and is detected by means of a subsequent hybridization with a complementary probe, wherein a competitor, which is a DNA molecule or a molecule of a nucleic acid analog capable of hybridizing to one of the two strands of the template but not to the region detected by hybridization to a probe and which cannot be enzymatically extended, is initially added to the PCR reaction.

Any molecule causing a preferred amplification of only one of the two template strands present in the PCR reaction can be used as competitor in the PCR. Thus, according to the present invention, competitors can be proteins, peptides, DNA ligands, intercalators, nucleic acids or analogs thereof. Proteins or peptides, which are capable of binding single-stranded nucleic acids with sequence specificity and which have the above-defined properties, are preferably used as competitors. Particularly preferably, nucleic acid molecules and nucleic acid analog molecules are used as to break open secondary structures.

The formation of one of the two template strands is substantially inhibited by the initial addition of the competitor to the PCR during amplification. "Substantially inhibited" means that a surplus of single strand and a amount of the other template strand sufficient to allow an efficient detection of the amplified strand by means of hybridization are produced in the PCR. Therefore, the amplification does not follow exponential kinetics of the form $2^n$ (with n=number of cycles), but rather attenuated amplification kinetics of the form $<2^n$.

The single strand surplus obtained by means of the PCR in relation to the non-amplified strand has the factor 1.1 to 1,000, preferably the factor 1.1 to 300, also preferably the factor 1.1 to 100, particularly preferably the factor 1.5 to 100, also particularly preferably the factor 1.5 to 50, in particular preferably the factor 1.5 to 20, and most preferably the factor 1.5 to 10.

Typically, the function of a competitor will be to bind selectively to one of the two template strands and therefore to inhibit the amplification of the corresponding complementary strand. Therefore, competitors can be single-stranded DNA- or RNA-binding proteins having specificity for one of the two template strands to be amplified in a PCR. They can also be aptamers sequence-specifically binding only to specific regions of one of the two template strands to be amplified.

Preferably, nucleic acids or nucleic acid analogs are used as competitors. Usually, the nucleic acids or nucleic acid analogs will act as competitors of the PCR either by competing with one of the primers used for the PCR for the primer binding site or by being capable of hybridizing with a region of a template strand to be detected due to a sequence complementarity. This region is not the sequence detected by the probe. Such nucleic acid competitors are enzymatically not extendable.

The nucleic acid analogs can, for example, be so-called peptide nucleic acids (PNA). However, nucleic acid analogs can also be nucleic acid molecules, in which the nucleotides are linked to one another via a phosphothioate bond instead of a phosphate bond. They can also be nucleic acid analogs, wherein the naturally occurring sugar components ribose or deoxyribose have been replaced with alternative sugars, like for example arabinose or trehalose or the like. Furthermore, the nucleic acid derivative can be "locked nucleic acid" (LNA). Further nucleic acid analogs are known to the person skilled in the art.

Preferably, DNA or RNA molecules, and particularly preferably DNA or RNA oligonucleotides or their analogs, are used as competitors.

Depending on the sequence of the nucleic acid molecules or nucleic acid analogs used as competitors, the inhibition of the amplification of one of the two template strands within the scope of the PCR reaction is based on different mechanisms. In the following, this is exemplarily discussed for a DNA molecule.

If, for example, a DNA molecule is used as competitor, it may have a sequence, which is at least partially identical to the sequence of one of the primers used for the PCR such that a specific hybridization of the DNA competitor molecule with the corresponding template strand is possible under stringent conditions. Since, within the present invention, the DNA molecule used for competition in this case is not extendable by means of a DNA polymerase, the DNA molecule competes with the respective primer for binding to the template during the PCR reaction. Depending on the ratio of the DNA competitor molecule and the primer, the amplification of the template strand defined by the primer can thus be inhibited in such a way that the production of this template strand is significantly reduced. Thereby, the PCR proceeds according to exponential kinetics higher than would be expected with the amounts of competitors used. In this manner, a single strand surplus emerges in an amount, which is sufficient for the efficient detection of the amplified target molecules by means of hybridization.

In this embodiment, the nucleic acid molecules or nucleic acid analogs used for competition must not be enzymatically extendable. "Enzymatically not extendable" means that the DNA or RNA polymerase used for the amplification cannot use the nucleic acid competitor as primer, i.e. it is not capable of synthesizing the corresponding opposite strand of the template 3' from the sequence defined by the competitor.

Alternatively to the above-depicted possibility, the DNA competitor molecule can also have a sequence complementary to a region of the template strand to be detected, which is not addressed by one of the primer sequences and which is enzymatically not extendable. In a PCR, the DNA competitor molecule will then hybridize to this template strand and correspondingly block the amplification of this strand.

The person skilled in the art knows that the sequences of DNA competitor molecules or, in general, nucleic acid competitor molecules can be selected appropriately. If the nucleic acid competitor molecules have a sequence, which is not substantially identical to the sequence of one of the primers used for the PCR, but is complementary to another region of the template strand to be detected, this sequence is to be selected in such a way that it does not fall within the region of the template sequence, which is detected with a probe within the scope of the hybridization. This is necessary because there does not have to occur a processing reaction between the PCR and the hybridization reaction. If a nucleic acid molecule, which falls within the region to be detected, were used as competitor, it would compete for binding to the probe against the single-stranded target molecule.

Such competitors preferably hybridize close to the template sequence detected by the probe. According to the present invention, the position specification "close to" is to be understood in the same way as given for agents breaking open secondary structures. However, the competitors according to the present invention can also hybridize in the immediate proximity of the sequence to be detected, i.e. at exactly one nucleotide's distance from the target sequence to be detected.

If nucleic acids or nucleic acid analogs that are not enzymatically extendable are used as competing molecules, they are to be selected with respect to their sequence and structure in such a way that they cannot be enzymatically extended by DNA or RNA polymerases. Preferably, the 3'-end of a nucleic acid competitor is designed in such a way that it has no complementarity to the template and/or has at its 3'-end a substituent other than the 3'-OH group.

If the 3' end of the nucleic acid competitor has no complementarity to the template, regardless of whether the nucleic acid competitor binds to one of the primer binding sites of the template or to one of the sequences of the template to be amplified by means of the PCR, the nucleic acid competitor cannot be extended by the conventional DNA polymerases due to the lack of base complementarity at its 3'-end. This type of non-extensibility of nucleic acid competitors by DNA polymerases is known to the person skilled in the art. Preferably, the nucleic acid competitor has no complementarity to its target sequence at its 3'-end with respect to the last 4 bases, particularly preferably to the last 3 bases, in particular preferably to the last 2 bases, and most preferably to the last base. In the mentioned positions, such competitors can also have non-natural bases, which do not allow hybridization.

Nucleic acid competitors, which are enzymatically not extendable, can also have a 100% complementarity to their target sequence, if they are modified in their backbone or at their 3'-end in such a way that they are enzymatically not extendable.

If the nucleic acid competitor has at its 3'-end a group other than the OH group, these substituents are preferably a phosphate group, a hydrogen atom (dideoxynucleotide), a biotin group, or an amino group. These groups cannot be extended by conventional polymerases.

The use of a DNA molecule, which competes with one of the two primers used for the PCR for binding to the template, and which was provided with an amino linkage at its 3'-end during chemical synthesis, as a competitor in such a method is particularly preferred. Such competitors can have 100% complementary to their target sequence.

However, nucleic acid analog competitors, like for example PNAs do not have to have a blocked 3'-OH group or a non-complementary base at their 3'-end as they are not recognized by the DNA polymerases because of the backbone modified by the peptide bond and thus are not extended. Other corresponding modifications of the phosphate group, which are not recognized by the DNA polymerases, are known to the person skilled in the art. Among those are inter alia nucleic acids having backbone modifications, like for example 2'-5' amide bonds (Chan et al. (1999) J. Chem. Soc., Perkin Trans. 1, 315-320), sulfide bonds (Kawai et al. (1993) Nucleic Acids Res., 1 (6), 1473-1479), LNA (Sorensen et al. (2002) J. Am. Chem. Soc., 124 (10), 2164-2176) and TNA (Schoning et al. (2000) Science, 290 (5495), 1347-1351).

Several competitors hybridizing to different regions of the template (for example, inter alia, the primer binding site) can also simultaneously be used in a PCR. The efficiency of the hybridization can additionally be increased, if the competitors have properties of secondary structure breakers.

In an alternative embodiment, the DNA competitor molecule can also have a sequence complementary to one of the primers. Depending on the ratio of antisense DNA competitor molecule and primer, such, for example, antisense DNA competitor molecules can then be used to titrate the primer in the PCR reaction, so that it will no longer hybridize with the corresponding template strand and, correspondingly, only the template strand defined by the other primer is amplified. The person skilled in the art is aware of the fact that, in this embodiment of the invention, the nucleic acid competitor can, but does not have to, be enzymatically extendable.

If, within the present invention, it is referred to nucleic acid competitors, this includes nucleic acid analog competitors, unless a different meaning arises from the respective context. The nucleic acid competitor can bind to the corresponding strand of the template reversibly or irreversibly. The bond can take place via covalent or non-covalent interactions.

Preferably, binding of the nucleic acid competitor takes place via non-covalent interactions and is reversible. In particular preferably, binding to the template takes place via formation of Watson-Crick base pairings.

The sequences of the nucleic acid competitors normally adapt to the sequence of the template strand to be detected. In the case of antisense primers, though, they adapt to the primer sequences to be titrated, which are in turn defined by the template sequences, however.

PCR amplification of nucleic acids is a standard laboratory method, the various possibilities of variation and development of which are familiar to the person skilled in the art. In principle, a PCR is characterized in that the double-stranded nucleic acid template, usually a double-stranded DNA molecule, is first subjected to heat denaturation for 5 minutes at 95° C., whereby the two strands are separated from each other. After cooling down to the so-called "annealing" temperature (defined by the primer with the lower melting temperature), the forward and reverse primers present in the reaction solution accumulate at those sites in the respective template strands, which are complementary to their own sequence. Herein, the "annealing" temperature of the primers adapts to the length and base composition of the primers. It can be calculated on the basis of theoretical considerations.

Information on the calculation of "annealing" temperatures can be found, for example, in Sambrook et al. (vide supra).

Annealing of the primers, which is typically performed in a range of temperatures between 40 to 75° C., preferably between 45 to 72° C. and in particular preferably between 50 to 72° C., is followed by an elongation step, wherein deoxyribonucleotides are linked with the 3'-end of the primers by the activity of the DNA polymerase present in the reaction solution. Herein, the identity of the inserted dNTPs depends on the sequence of the template strand hybridized with the primer. As normally thermostable DNA polymerases are used, the elongation step usually runs at between 68 to 72° C.

In a symmetrical PCR, an exponential amplification of the nucleic acid region of the target defined by the primer sequences is achieved by means of repeating the described cycle of denaturation, annealing and elongation of the primers. With respect to the buffer conditions of the PCR, the usable DNA polymerases, the production of double-stranded DNA templates, the design of primers, the selection of the annealing temperature, and variations of the classic PCR, the person skilled in the art has numerous references at his disposal.

The person skilled in the art is familiar with the fact that, for example, single-stranded RNA, such as mRNA, can be used as template as well. Usually, this mRNA is previously transcribed into a double-stranded cDNA via a reverse transcription.

In a preferred embodiment, a thermostable DNA-dependent polymerase is used as polymerase. In a particularly preferred embodiment, a thermostable DNA-dependent DNA polymerase is used, which is selected from the group consisting of Taq-DNA polymerase (Eppendorf, Hamburg, Germany and Qiagen, Hilden, Germany), Pfu-DNA polymerase (Stratagene, La Jolla, USA), Tth-DNA polymerase (Biozym Epicenter Technol., Madison, USA), Vent-DNA polymerase, DeepVent-DNA polymerase (New England Biolabs, Beverly, USA), Expand-DNA polymerase (Roche, Mannheim, Germany).

The use of polymerases, which have been optimized from naturally occurring polymerases by means of specific or evolutive alteration, is also preferred. When performing the PCR in the presence of the substance library support, the use of the Taq-polymerase by Eppendorf (Germany) and of the Advantage cDNA Polymerase Mix by Clontech (Palo Alto, Calif., USA) is particularly preferred.

All devices according to the present invention, which can be employed for the methods according to the present invention, can, in a preferred embodiment, have a so-called displacement structure, irrespective of whether they have or have not immobilized probe molecules in a region of the first surface, and irrespective of whether they are used, for example, for nucleic acid target/probe interactions or protein target/probe interactions or for concentration measurements of targets without probes.

Any preceding methods may also be performed using an inventive device having a displacement structure, as described above.

Another aspect of the present invention relates to the use of an inventive device for performing microarray-based tests.

In the following, special embodiments of the inventive devices and the inventive method are described.

Figure 5:
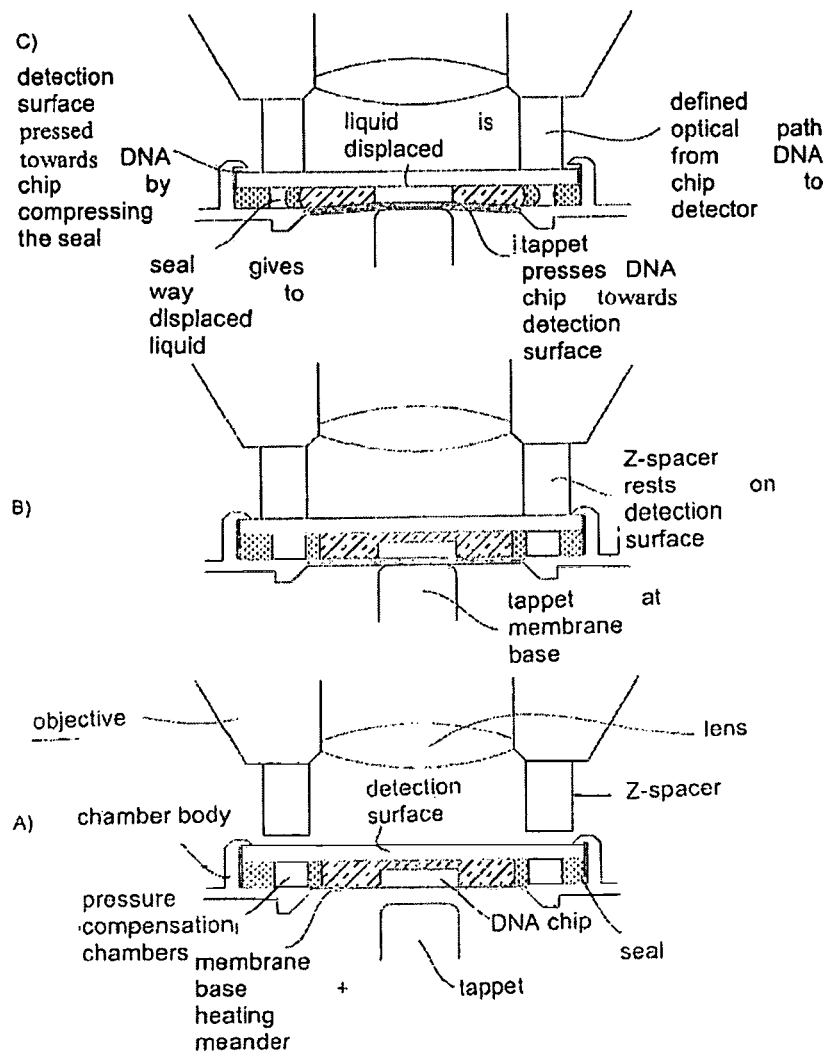
FIG. 5 is an illustration of the status of the process unit according to the present invention in the read out device A) during PCR, B) before detection, and C) during detection.

In FIG. 5, it is shown that the first surface, here an elastic membrane, in which preferably a heating device is integrated, is deformed by means of a pin or a tappet and that the chip is thus pressed towards the detection surface. Furthermore, the detection surface is pressed into the reaction chamber via a spacer on the second surface and thus approaches the DNA chip from above until the liquid between DNA chip and detection plane is almost entirely displaced. The elastic seals sealing the reaction chamber are compressed by guiding the detection surface towards the chip. The displaced fluid deforms the seal in such a way that the air is compressed in air compensation chambers. This occurs in a more efficient manner, if the second surface has the displacement structure described above.

However, the process unit can also be configured such that either only the first surface, for example in form of an elastic membrane, is deformed or only the detection plane is pressed into the chamber, potentially by using a displacement structure.

Figure 6:
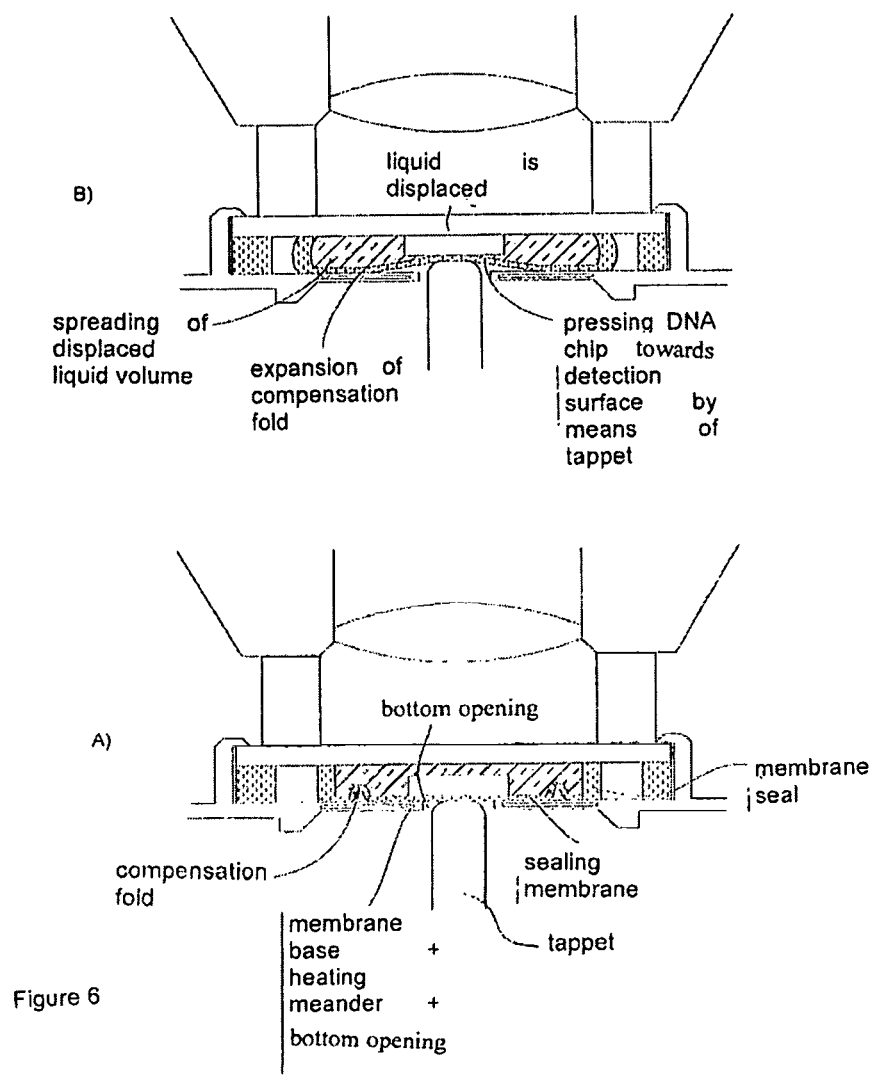
FIG. 6 is an illustration of the mode of function of the process unit according to the present invention having membrane seal, compensation fold, and bottom hole. In A), the process unit is shown in home position. In B), the process unit is shown in compressed form, in which the fluorescent solution between DNA-chip and detection surface is displaced.

In FIG. 6, a further technical embodiment for compressing the process unit is depicted. The reaction chamber is sealed laterally and at the side opposite the detection surface by a sealing membrane, on which a DNA chip is attached. At the level of the DNA chip, the sealing membrane seals a hole in the lower side of the chamber body. The hole is slightly smaller than the DNA chip. When conducting a PCR in the reaction chamber, the hole is tightly sealed by the internal pressure forming due to the raised temperatures connected with the PCR. Therefore, despite the labile sealing membrane, the chamber is pressure-proof (principle of the self-closing valve). For detection, a pin or a tappet is pushed through the lower side hole. The sealing membrane is lifted and the DNA chip is pressed against the detection plane. In order to ensure the required elasticity of the sealing membrane, the membrane can be provided with a compensation fold. In this embodiment, the pressure compensation chambers are also compressed by the displaced liquid. This embodiment may also have a displacement structure.

The following examples are for the purpose of illustrating the invention, and are not to be construed as limiting the scope of the invention.

EXAMPLES

Example 1

Setup of a Reaction Cartridge without an Integrated Heating

Figure 8:
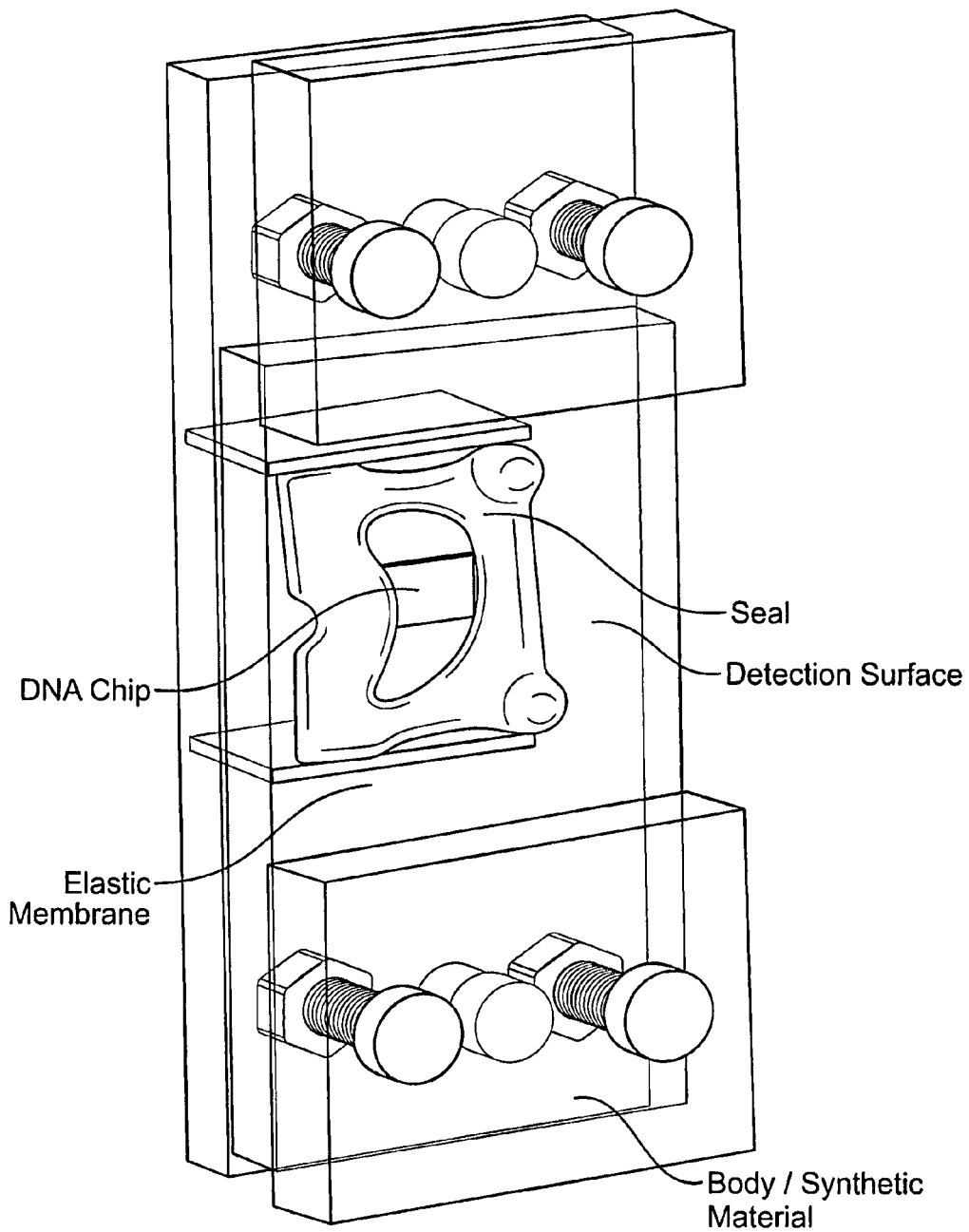
FIG. 8 is a diagram depicting a view of an exemplary milled and bolted process unit.
Figure 9:
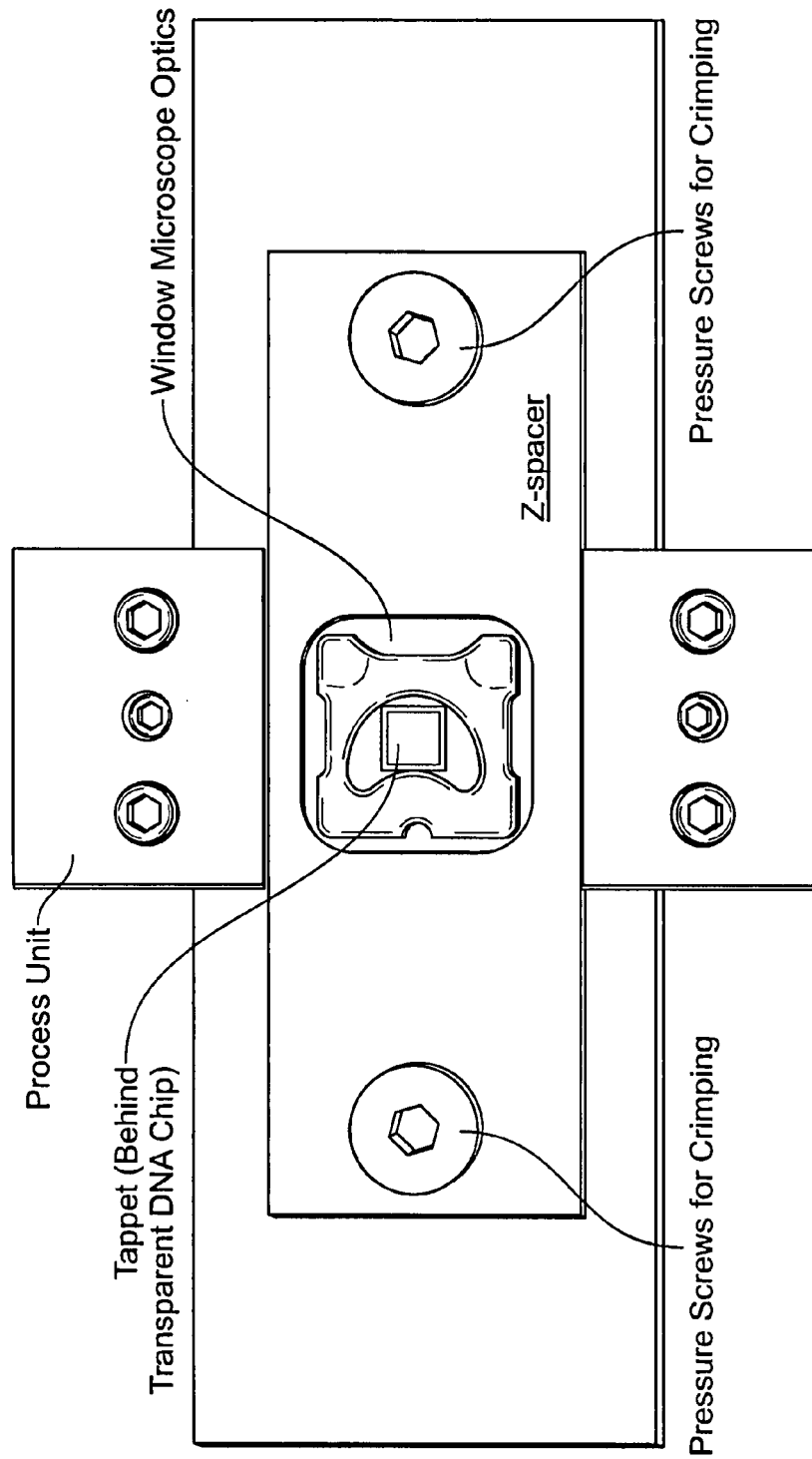
FIG. 9 is a diagram depicting a view of an exemplary compressing or crimping device for the process unit according to the present invention for the detection of the hybridization signals in a conventional fluorescence microscope.

In FIGS. 8 and 9, an embodiment of a processing unit without integrated heating and a device for guiding a substrate which overlies the first surface and onto which the probes can be immobilized toward the detection plane are depicted. The substrate in the device shown can be read out by means of a conventional fluorescence microscope (for example Axioskop, Zeiss, Jena, Germany).

Example 2

Setup of a Reaction Cartridge Having a Silicon Heating Substrate

The variant of the processing unit of the device according to the present invention, which is shown in FIGS. 10 and 11, is a miniaturized reaction cartridge having a substrate overlying the first substrate which is represented by a heating/sensor substrate and onto which probes can be immobilized wherein it is not about a microarray, a silicon heating substrate having an integrated temperature sensor ("heating substrate") for adjusting distinctive temperatures in the reaction chamber as well as a circuit board optionally having an EPROM for electrically contacting the heating substrate. The individual components are embedded in two shells made of synthetic material. The entire unit is a spatially closed system, in which all required reactions (for example PCR) can be conducted in a temperature-controlled manner.

First, the circuit board is inserted into the provided shaft in the lower shell (with the EPROM facing downward). On the upper side of the circuit board, three electric contact pads are arranged, which ensure the electric connection with the subsequently inserted heating substrate, which in turn bears the contact pads. Said heating substrate has a size of 8 mm×6 mm and a thickness of about 0.6 mm. The heating substrate ensures exact adjustment of different temperatures (for example of 40° C. to 95° C.) within the scope of the examination conducted. Herein, measuring the temperature in the reaction chamber can be conducted either via the sensor integrated in the heating substrate or via an external measuring unit, which measures the temperature directly on the surface of the heating substrate. In the latter case, the integrated sensor in the heating substrate can be omitted. The integrated components used for heating and/or temperature measurement can, for example, be diodes or also transistors. The surface of the silicon heating substrate, which is facing toward the reaction space, contains no electric systems whatsoever and is coated with an $SiO_2$ passivating layer.

The next component is an elastic seal, which laterally limits the reaction space.

In the center of the reaction space, the substrate is attached in such a way that it is facing toward the detection plane. After inserting the detection plane in the form of a glass surface, said surface still protrudes from the lower shell by 0.2 mm. By subsequently joining the upper shell, which is guided by means of locating pins, the glass surface is pressed against the seal and thus ensures optimal sealing of the reaction chamber.

Subsequently, the reaction chamber can be filled with reaction solution. Herein, it is to be noted that only the inner space containing the chip is filled, but not the outer chambers. The liquids required are injected into the reaction space with cannulas via the provided cannula guide.

Subsequently, biochemical reactions controlled via the silicon heating substrate, like for example PCR and/or hybridization, can be conducted in the reaction chamber.

For detecting the intermediate results or the final result, the detection plane is pressed against the substrate from above by means of the spacers of the detection unit, until the distance between detection plane and substrate is about zero. Herein, the surrounding liquid is dislocated into the outer chambers, where it compresses the local air. This process is reversible and can, for example, be conducted after each PCR cycle. The same is true for binding assays between protein targets and protein probes.

Due to its compact design and the internal circuit board having an EPROM and the integrated heating substrate, this variant of the device according to the present invention is particularly suitable for mobile use.

Example 3

Detection of the Decrease of Background Signal by Displacing the Analyte

All fluorescence measurements described in this example were performed using a fluorescence microscope (Zeiss, Jena, Germany). Excitation occurred in incident light using a white light source and a filter set suitable for Cyanine 3. The signals were recorded by means of a CCD camera (PCO-Sensicam, Kehlheim, Germany). In the following, the thickness of the gap denotes the distance between microarray and detection plane.

a) Measuring the Fluorescence Signal of the Analyte Depending on the Thickness of the Gap Channel shells having defined channel depth (5 μm, 10 μm, 28 μm) made of Sylgard were cast. The channels had a width of 125 μm. A glass chip was placed across the unequally deep channels. The channels were then filled with a 200 nM solution of a Cy3-labeled oligonucleotide in 2×SSC+0.2% SDS and the signal was measured with an exposure time of 1.5 s.

Figure 12:
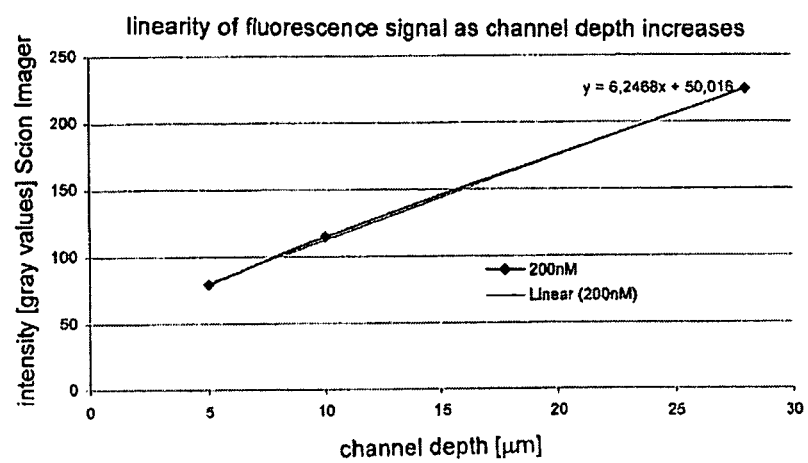
FIG. 12 is a diagram depicting a view of the straight regression line for determining the width of a gap filled with fluorophore.

In FIG. 12, the results are depicted. The signal increases linearly as the channel depth increases. A straight regression line could be calculated (equation 1)

$$F(x)=6.2468x+50.016 \quad \text{(Equation 1)}$$

Using the regression equation obtained (equation 1), the layer thicknesses between DNA chip and detection surface can now be determined by means of the background fluorescence signal.

Figure 13:
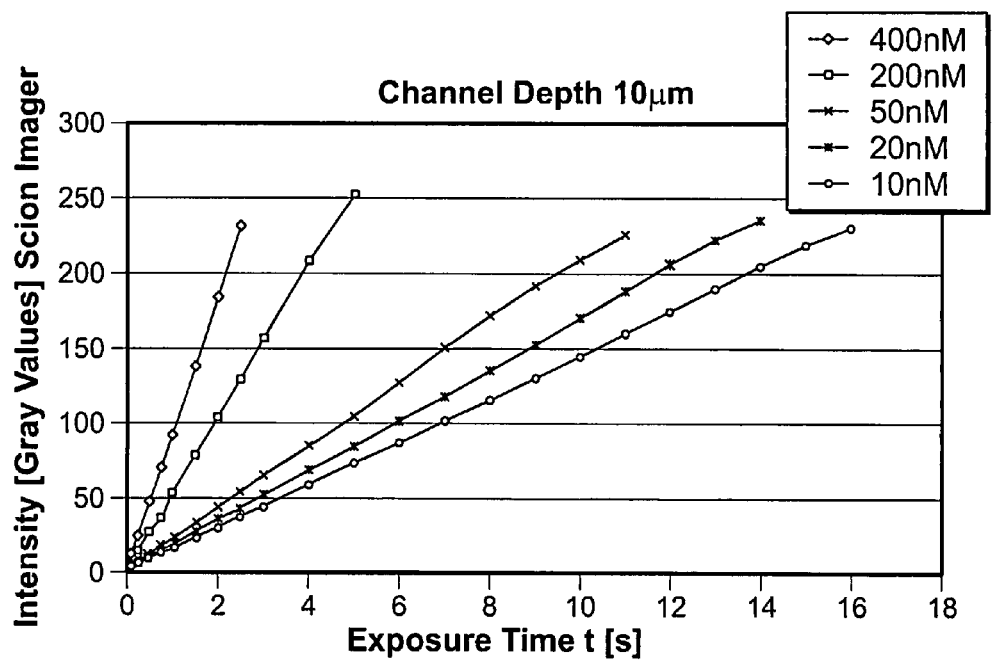
FIG. 13 is a diagram depicting a view of the linearity of the fluorescence signal as the exposure time increases over the metering range.
Figure 14:
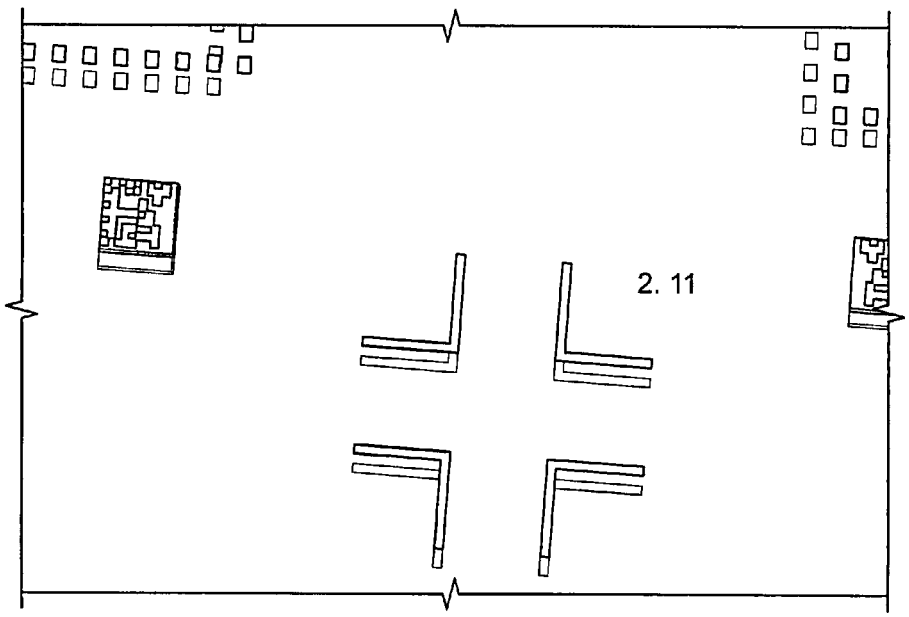
FIG. 14 is a diagram depicting a fluorescence recording of two superimposed chips, the gap between which is filled with 200 nM Cy3 fluorophore. The intensity of the background is 158 gray values at an exposure time of 0.75 s. The thickness of the gap measured using a fluorescence microscope is 40.00 µm. Assuming that the measured gray values behave linearly in relation to the exposure time (see FIG. 13), the resulting thickness of the gap, as determined by using equation 1, is 42.6 µm. The values for the thickness of the layer thus obtained are in well agreement with each other.
Figure 15:
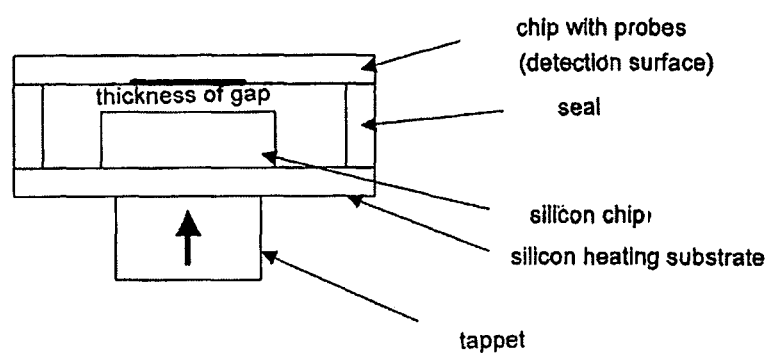
FIG. 15 is an illustration of the experimental setup for the detection of DNA arrays without rinsing.

This was analyzed by stacking two glass surfaces (chips) having structured marks on their upper sides (crosses, numbers, and data matrix in FIG. 14), to which could be focused. The chips were stacked in such a way that the structured marks were oriented towards each other and were only separated by a thin liquid layer. A 200 nM solution of a Cy3-labeled oligonucleotide in 2×SSC+0.2% SDS was used as liquid. Using the focusing device of the microscope, which was provided with a scale, the distance between the marks and therefore the layer thickness of the liquid film could directly be determined. The intensity of the background is 158 gray values with an exposure time of 0.75 s. The thickness of the gap as measured using the fluorescence microscope, is 40 μm. Assuming that the measured gray values behave linearly in relation to exposure time (see FIG. 13), according to equation 1 the resulting thickness of the gap is 42.6 μm. The values for the thickness of the liquid layer thus obtained are well in agreement with each other.

b) Experiments for Reducing or Preventing Background Fluorescence by Means of Compressing the Process Unit In these experiments, the hybridization signal was measured depending on the displacement of the fluorescent analyte caused by applying pressure via a tappet. The experimental setup is shown in FIG. 15. By applying pressure via the tappet, the silicon chip (3.15×3.15 mm) was pressed towards a probe chip (DNA chip), and in this process the liquid located between the two surfaces was displaced.

For performing the experiment, the chamber was filled with a hybridization solution, representing a model system for the conditions in a PCR hybridization. The hybridization solution included a Cy3-labeled oligonucleotide (final concentration 2 nM in 2×SSC+0.2% SDS), which displayed complementarity to the probe array. In addition, the hybridization solution included another Cy3-labeled oligonucleotide, which does not hybridize with the probe array and therefore only contributes to the fluorescence background signal in the solution, but not the specific signals at the spots.

Hybridization was performed for 10 min. For the subsequent reading out the hybridization signals, a fixed exposure time of 1.5 s was selected. At the experimental setup, the tappet was pushed nearer towards the probe array (detection surface) after each recording, so that the gap between array and second surface, which is filled with hybridization solution, was reduced.

Figure 16:
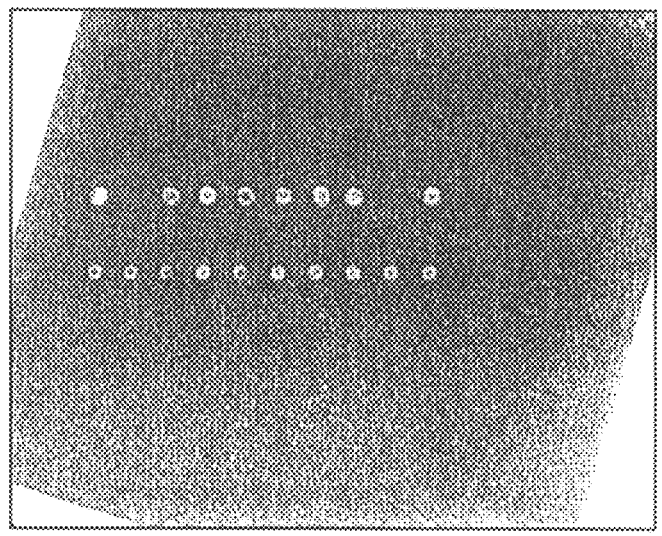
FIG. 16 is a diagram depicting a fluorescence measurement of an array with chip pressed against it. The white margins are indicative for the background radiation caused by the displaced sample solution.
Figure 17:
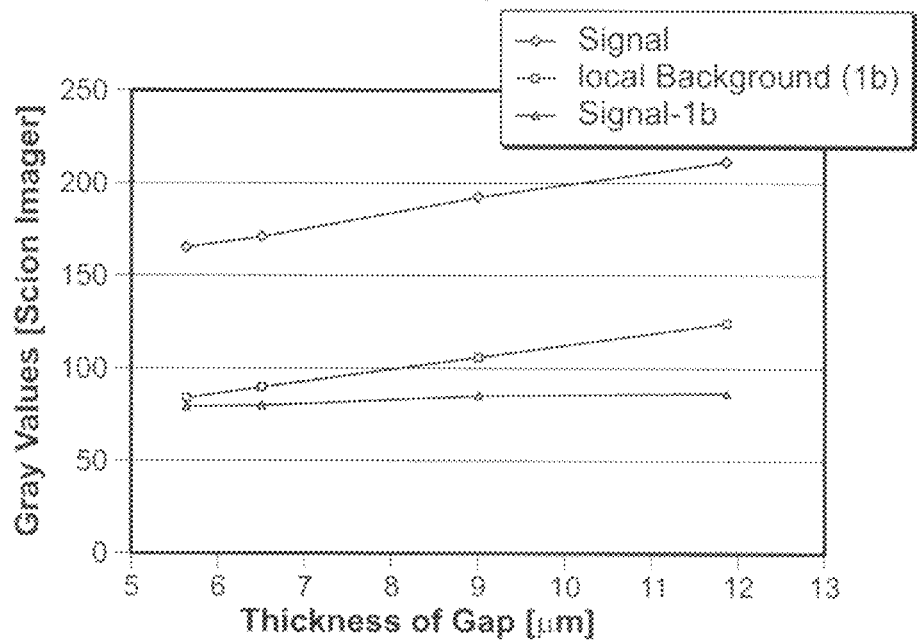
FIG. 17 is a diagram depicting a decrease of absolute intensities of signal and background with reduced thickness of the gap. The difference of both values is constant throughout the metered region.

FIG. 16 shows a recording of the hybridization signal with a thickness of the gap of 10 μm. The results for background signal and hybridization signal at the spots are depicted in FIG. 17. As expected, both signals behave linearly in relation to the thickness of the gap. Thus, the spot signal that is corrected by the background does not change with the thickness of the gap.

When a gray value of 255 is reached, the instrument is overloaded. That is, with a thickness of the gap of about 17 µm, measuring the spot intensity is only possible by reducing exposure time. For that reason, measuring sensitivity is then reduced.

Thus, the dynamic measuring range is increased by reducing the thickness of the gap. By means of background adjustment of the spot signals (difference formation), the thickness of the gap can be varied in a broad range without influencing the measurement and the results. With very large thicknesses of the gap (>20 µm), measurement is strongly impaired due to overload of the detector.

c) Amplification, Hybridization and Detection as One-Stage Reaction

Two process units having a structure according to FIG. 15 were mounted and numbered.

Two identical reaction setups having the following composition were prepared:

```
Reaction setup:
20 mM dNTPs                              0.5 µl

1 M potassium acetate (Kaac)            3 µl 25 mM Mg-acetate Eppendorf               5 µl Clontech C-DNA PCR buffer                5 µl Eppendorf Taq-polymerase                 3 µl 10 µM primer CMV_DP_Cy3                  1 µl
Cy3_5'TGAGGCTGGGAARCTGACA3'
(SEQ ID NO: 1)

10 µM Primer CMV_UP_NH2                  0.66 µl
5'GGGYGAGGAYAACGAAATC3'_NH2
(SEQ ID NO: 2)

10 µM primer CMV_UP                      0.33 µl
5'GGGYGAGGAYAACGAAATC3'
(SEQ ID NO: 2)

10 µM primer Entero_DP_Cy3               1 µl
Cy3_5'CCCTGAATGCGGCTAAT3'
(SEQ ID NO: 3)

10 µM primer Entero_UP_NH2               0.66 µl
5'ATTGTCACCATAAGCAGCC3'_NH2
(SEQ ID NO: 4)

10 µM primer Entero_UP                   0.33 µl
5'ATTGTCACCATAAGCAGCC3'
(SEQ ID NO: 4)

10 µM primer HSV1_DP_Cy3                 1 µl
Cy3_5'CTCGTAAAATGGCCCCTCC3'
(SEQ ID NO: 5)

10 µM primer HSV1_UP_NH2                 0.66 µl
5'CGGCCGTGTGACACTATCG3'_NH2
(SEQ ID NO: 6)

10 µM primer HSV1_UP                     0.33 µl
5'CGGCCGTGTGACACTATCG
(SEQ ID NO: 6)

10 µM primer HSV2_UP_Cy3                 1 µl
Cy3_5'CGCTCTCGTAAATGCTTCCCT3'
(SEQ ID NO: 7)

-continued
10 µM primer HSV2_DP_NH2                 0.66 µl
5'TCTACCCACAACAGACCCACG3'_NH2
(SEQ ID NO: 8)

10 µM primer HSV2_DP                     0.33 µl
5'TCTACCCACAACAGACCCACG3'
(SEQ ID NO: 8)

10 µM primer VZV_DP_Cy3                  1 µl
Cy3_5'TCGCGTGCTGCGGC
(SEQ ID NO: 9)

10 µM primer VZV_UP_NH2                  0.66 µl
5'CGGCATGGCCCGTCTAT3'_NH2
(SEQ ID NO: 10)

10 µM primer VZV_UP                      0.33 µl
5'CGGCATGGCCCGTCTAT
(SEQ ID NO: 10)

Template CMV                             1 µl

PCR grade water                         22.5 µl total                                   50 µl
```

The process units were filled with 50 µl reaction setup each and processed according to the following temperature-time scheme.

| | | |
|---|---|---|
| 1 | Denaturation | 95° C. |
| | Duration | 300 s |
| 2 | Denaturation | 95° C. |
| | Duration | 10 s |
| 3 | Annealing/Extension | 60° C. |
| | Duration | 20 s |
| Repeating steps 2 to 3 | | 35 times |
| 4 | Denaturation | 95° C. |
| | Duration | 300 s |
| 5 | Hybridization | 40° C. |
| | Duration | 3600 s |

Then, the two process units were subjected to different treatments. In the first case (process unit 1), the background fluorescence was reduced by displacing the analyte. This was accomplished by pushing the tappet upwards in the direction of the detection surface, so that the gap filled with reaction solution is reduced as far as possible.

In the second case (process unit 2), the analyte was replaced by a non-fluorescent solution. The replacement of the solution was performed with 2×SSC buffer at a fluctuation rate of 300 µl/min and a rinsing volume of 900 µl. This procedure corresponds to the state of the art.

Subsequently, both strategies for reducing background fluorescence were compared. To this end, the hybridization signals in both process units were detected with the aid of the fluorescence microscope camera setup described.

Figure 18:
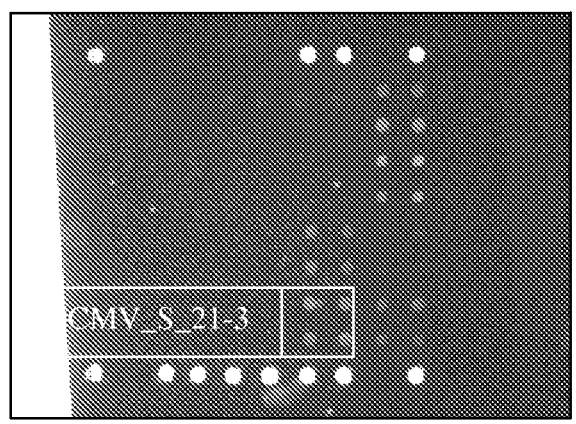
FIG. 18 is a diagram depicting a detection of the probe signals by displacing background fluorescence. At the left margin, the non-displaced liquid is shown.
Figure 19:
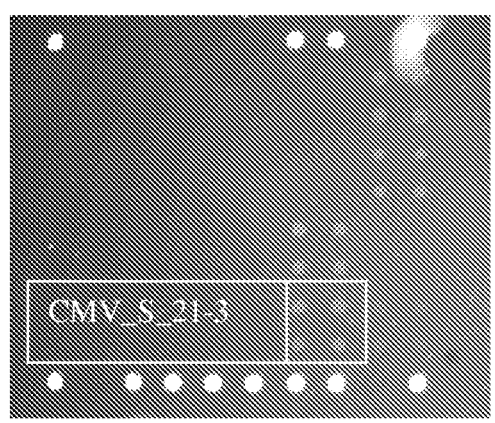
FIG. 19 is a diagram depicting a detection of the probe signals of a DNA array. The background was corrected by rinsing.

Exposure time was 5 s (see FIG. 18 and FIG. 19). Comparing the spot intensities was performed on the basis of the spot comprising substance CMV_S_21-3 (5'-NH$_2$TGTTGGGCAACCACCGCACTG-3' (SEQ ID NO: 11)). The location of the probes is indicated in FIGS. 18 and 19.

Figure 20:
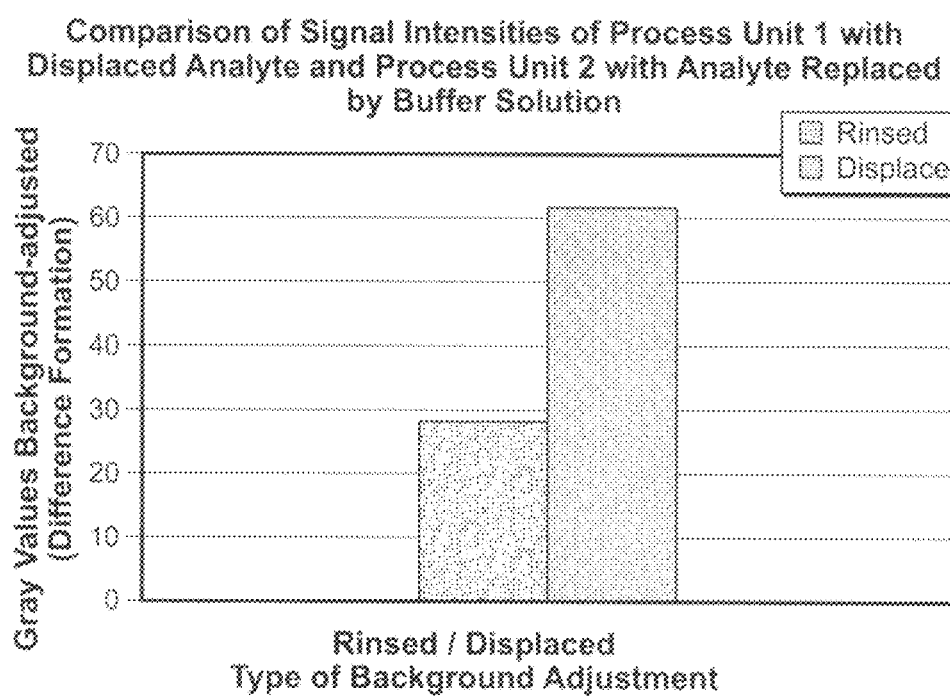
FIG. 20 is a diagram depicting a measurement results of an experimental comparison of displacement and replacement of the analyte.

In FIG. 20, the result of the experiment is shown. By rinsing the reaction chamber in process unit 2, the hybridization signal is reduced compared to the displacement in process unit 1. It is assumed that "bleeding" of the probes is responsible for this.

Thus, the method of analyte displacement according to the inventive method is to be preferred compared to replacement of the solutions.

Figure 21:
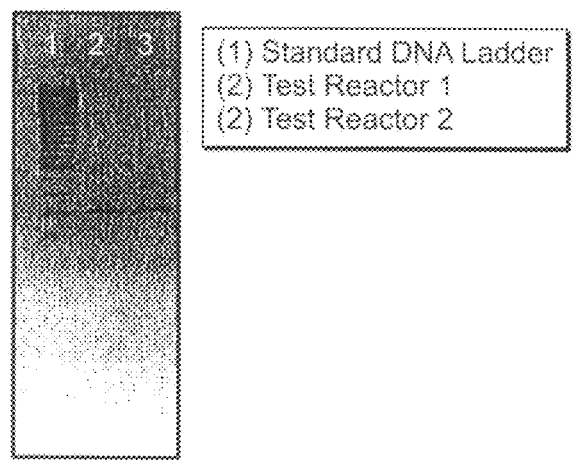
FIG. 21 is a diagram depicting a reference analytics of the PCR in a process unit, measured by gel electrophoresis.

In order to obtain evidence on amount and integrity of the amplification product, 5 μl of each reaction solution were additionally analyzed on a 2% agarose gel. The result (ethidium bromide-stained gel detected with an UV transilluminator) is shown in FIG. 21.

Example 4

Device for the Processing and Detection of Inventive Reaction Cartridges

A device for the processing and detection of inventive reaction cartridges in accordance with this Example is shown in FIG. 28.

The device for performing microarray-based tests with reaction cartridges according to the present invention usually consists of several components, which may be combined in one device or assembled modularly from several partial devices. Optionally, the device may be activated via an integrated computer or via an interface to an external computer. The setup of the device is illustrated in FIG. 28.

An exemplary procedure is as follows:

The fluid interface of the reaction cartridge is manually brought in the filling position by the operator, in which the cannulas penetrate the seal of the chamber body. Subsequently, the operator introduces the reaction mixture into the reaction chamber by means of a standard laboratory pipette. Both steps can also be achieved by a correspondingly configured device. The fluid interface is then again brought in the home position, wherein said procedure can also be achieved by a correspondingly configured device.

The reaction cartridge is then inserted into the device. A data matrix reader, which is arranged in the device, recognizes the unique data matrix attached to the reaction cartridge and, via a user-transmitted data set, transfers the characteristic data for the cartridge as well as for the test to be conducted to the control computer. This computer then controls the individual process steps, which can, for example, comprise an amplification and hybridization. Via the integrated pressure means, the capillary gap in the reaction chamber is subsequently reduced according to the present invention to allow for detection.

Detection can be performed with conventional fluorescence-optical imaging or non-imaging systems. The data thus obtained are transmitted to a control computer for evaluation as well as presentation or storage on an internal or external interface.

Then, the reaction cartridge can be removed from the device and discarded by the operator.

Example 5

Reaction Cartridge Made of Electrically Conductive Synthetic Material

A reaction cartridge as depicted in FIG. 29 is prepared.

The lower shell (1) of the reaction cartridge consists of electrically conductive synthetic material forming the base of the reaction chamber (Conduct 2, RKT, Germany). A foil PT-100 temperature sensor is fixed to the bottom side of the chamber base using a suitable adhesive, for example Loctite 401 (Loctite, Germany). Together with the seal (3) and the coverslip (4), the lower shell forms the reaction chamber of the cartridge according to the present invention.

The cartridge further has a threaded drill hole (2) for inserting screws for electrical contacting, an upper shell (5) of the reaction cartridge, for example one made of acryl, a drill hole (6) for attaching the upper shell, and a detection window (7) within the upper shell.

A standard PCR reaction mixture is prepared:

| | |
|---|---|
| 30.5 μl | de-ionized water |
| 5 μl | 10x PCR buffer (e.g., 10x cDNA PCR reaction buffer, Clontech, Germany) |
| 5 μl | Mg-acetate, 25 mM (e.g., Eppendorf, Germany) |
| 0.5 μl | dNTP, 20 mM each |
| 1 μl | 16sfD1 (5'-AGAGTTTGATCCTGGCTCAG-3') (SEQ ID NO: 12)), 10 mM |
| 1 μl | 16sRa (5'-TACCGTCACCATAAGGCTTCGTCCCTA-3') (SEQ ID NO: 13)), 10 mM |
| 3 μl | Taq DNA polymerase (e.g., Genaxxon, Germany) |
| 1 μl | template |

By using an insulin syringe (Becton Dickinson, Germany), the reaction chamber is filled with the reaction mixture. For ventilation during the filling procedure, a second cannula is penetrated through the seal of the chamber body. After filling, ventilation cannula and insulin syringe are properly discarded.

The chamber is then connected to a regulating unit (CLONDIAG chip technologies GmbH, Germany) via the two screws provided for this purpose. Likewise, the temperature sensor is connected to said regulating unit at the bottom side of the lower shell. Said regulating unit is capable of regulating specific temperatures in the lower shell according to a predefined program.

In this manner, the following PCR program is conducted: 5 min 95° C., 30×(30 s 95° C., 30 s 62° C., 50 s 72° C.).

FIG. 30 shows an image of the reaction cartridge recorded using a thermal imaging camera at a temperature of 95° C.

After completion of the program, the reaction product is removed from the reaction chamber by means of an insulin syringe. Analogously, a cannula is penetrated through the seal of the chamber body for ventilation during the emptying of the reaction chamber.

The reaction product is analyzed by agarose gel electrophoresis. To this end, 5 μl of the reaction solution, along with a suitable buffer (for example 5 μl 250 mM in 50% glycerin, bromphenol blue), are applied to the pocket of a 2% agarose gel and an electrophoresis is performed. The result is depicted in FIG. 31.

As can clearly be seen, an amplification product of correct size and in an amount comparable to the positive control could be obtained in all cases.

Example 6

Reaction Cartridge Having a Displacement Structure on the Second Surface

A reaction cartridge as shown in FIG. 5 or 6 is prepared. In the center of the second surface of the inventive device a drop (about 20 μl) of Sylgard 184 is deposited using a pin. Subsequently, the second surface with the silicone drop is incubated, for example, in an oven at 120° C. for one hour in order to cross-link the Sylgard. Subsequently said second surface is assembled in a device according to the present invention. A DNA probe array is applied onto the first surface.

A PCR setup is prepared according to the following scheme:

| 10x Clontech cDNA buffer | 20 µl |
|---|---|
| 25 mM Mg acetate Eppendorf | 20 µl |
| dNTP's 20 mM each | 2 µl |
| Genaxxon Taq polymerase | 12 µl |
| Bidest | 122 µl |
| Primer 1 10 µM with Cy3 label | 4 µl |
| Primer 2 10 µM | 4 µl |
| 1 M K acetate | 12 µl |
| Template DNA | 4 µl |

20 µl of this mixture are introduced in the inventive device. Subsequently, the device is connected to a corresponding controller (prototype, Join, Jena, Germany), and a PCR is performed according to the following scheme.

| 1) | Denaturation | 95° C. | 500 s |
|---|---|---|---|
| 2) | Denaturation | 95° C. | 10 s |
| 3) | Annealing | 60° C. | 30 s |
| 4) | Elongation | 72° C. | 30 s |
| 5) | 37 times repeating steps 2 to 4 | | |
| 6) | Denaturation | 95° C. | 60 s |
| 7) | Hybridization | 50° C. | 45 min |

Then, the first surface is guided towards the second surface until the displacement structure contacts the surface area of the first surface. By flattening the elastic displacement structure on the surface of the microarray, the fluorescent solution causing the background is displaced completely and the signal can be detected. (see FIG. 33).

Example 7

Detection of CD4 Antigens on Lymphocytes

As was mentioned above, the methods according to the present invention can also be performed by means of devices, wherein the reaction chamber formed by a first and a second surface is formed by different objects. As an example, it was referred to a reaction vessel, into which a snug-fit tappet, piston, or stamp is inserted in order to form a correspondingly narrow reaction chamber from which the analyte liquid is displaced. This principle has been explained by way of FIG. 34.

Concretely, a micro well plate made of polystyrene having an amino-modified surface (for example nunc Immobilizer F96 Micro Well Plate—Amino)) is coated with anti-CD4 antibody (Molecular Probes). The antibody is incubated at a concentration of 0.2 µg/µl in 1×PBS buffer in the plate at 23° C. for 1 h and the plate is subsequently washed with 1×PBS buffer.

40 µl of a blood sample are mixed with 160 µl deionized water, 40 µl 0.5 M EDTA solution and 5 µl of a solution of an anti-CD4 antibody labeled with the fluorescence dye phycoerythrin in 1×PBS (Molecular Probes, original concentration 0.2 mg/ml), are briefly shaken and transferred to a well in the plate coated with capture-antibody.

After short incubation (15 min) in a shaker (500 r/min) at room temperature, the plate is read out on an inverse fluorescence microscope. To this end, tappets are inserted into the wells of the plate, which come to rest directly on the surface of the plate and have the characteristic of substantially displacing the liquid and not emitting fluorescence light within the selected detection range (excitation: 541 nm, emission: 576 nm) themselves. The signal is recorded by means of a CCD camera and compared to the signal measured in other wells of the plate.

Example 8

Detection of the Number of Lymphocytes Bearing CD4 Antigen

As was mentioned above, the methods according to the present invention can also be performed if the probes are not immobilized to the first surface of the reaction chamber. This aspect of the invention was explained by way of FIGS. 35 and 36.

Concretely, 1 µl of a blood sample is mixed with 4 µl deionized water, 1 µl 0.5 M EDTA solution and 0.5 µl of a solution of an anti-CD4 antibody labeled with the fluorescence dye phycoerythrin in 1×PBS (Molecular Probes, original concentration 0.2 mg/ml), briefly shaken and transferred to a compressible detection chamber.

The exemplary compressible detection chamber is generated by means of a cartridge as it was described above and is, for example, depicted in the FIGS. 3 to 6 or in the FIGS. 10 and 11, but without using the chip equipped with the heating sensor, however.

Instead, a PDMS membrane having a thickness of about 0.3 µm is used as first surface. For detection, said membrane is pressed against the detection plane and read out by means of a fluorescence microscope (Axioskop, Zeiss, Germany, excitation: 541 nm, emission: 576 nm).

The result is depicted in FIG. 37. The dark spots (a), (exemplary) are erythrocytes, which are not recognized by the anti-CD4 antibody. The light spots (b) are lymphocytes. In the present experiment, 5 lymphocytes can thus be detected in the detection volume.

If a substrate is mentioned in the above-mentioned Figures, this is to be understood to denote a substrate, in which probes can be immobilized, such as, for example, a microarray. In case there are no probes immobilized, the term substrate is, in this context, supposed to define the region of the first surface or the second surface, where the detection of the targets is supposed to take place in the state of the compressed reaction chamber. In both cases (i.e. immobilized probe and non-immobilized probe, respectively), the substrate does not have to be an individual component, but it can represent a region of the first surface (immobilized probes) or of the first and/or second surface (non-immobilized probes).

A number of embodiments have been described. Nevertheless, it will be understood that various modifications may be made without departing from the spirit and scope of the invention. All references identified herein are incorporated by reference in their entirety. Accordingly, other embodiments are within the scope of the following claims.

What is claimed is:

1. A method, comprising:

forming a mixture between a first surface and a second surface of a reaction chamber, the mixture including (a) a liquid, (b) a first complex including a first analyte and a first portion of a first optical label, and (c) a second portion of the first optical label, the second portion being in an uncomplexed state with respect to the first analyte, wherein the second portion has a greater mobility than the first complex;

reducing a distance between the first surface and the second surface and displacing at least a portion of the mixture from between the first surface and the second surface; and detecting the first optical label remaining between the first surface and the second surface while the distance is reduced;

without removing the mixture from or introducing a liquid free of the first optical label into the reaction chamber at any time between forming a mixture, reducing a distance and detecting the first optical label.

2. The method of claim 1, wherein the complex is immobilized with respect to the first surface or the second surface.

3. The method of claim 1, wherein the mixture further includes (d) a second complex including a second analyte differing from the first analyte, and a first portion of a second optical label, (e) a second portion of the second optical label, the second portion being in an uncomplexed state with respect to the second analyte, wherein the second portion has a greater mobility than the second complex.

4. The method of claim 3, further comprising detecting the second optical label remaining between the first surface and the second surface.

5. The method of claim 4, wherein the first optical label and the second optical label are the same.

6. The method of claim 5, wherein the first complex is immobilized with respect to the first surface or the second surface, and the second complex is immobilized with respect to the first surface or the second surface, and the first complex is spaced apart from the second complex.

7. The method of claim 6, wherein the first complex includes a nucleic acid and the second complex includes a nucleic acid.

8. The method of claim 1, wherein the first complex is immobilized on the first surface.

9. The method of claim 8, wherein a microarray of nucleic acids is immobilized on the first surface.

10. The method of claim 8, wherein the second surface includes a displacement structure.

11. The method of claim 10, wherein the displacement structure includes an elastic material.

12. The method of claim 11, wherein the displacement structure has a convex shape.

13. The method of claim 1, wherein the first complex includes a nucleic acid, a peptide, a protein, an antigen, an antibody, a carbohydrate, a low molecular weight chemical compound, or a cell.

14. The method of claim 1, wherein the distance between the first surface and the second surface is reduced so that the mixture is substantially completely displaced from between the first surface and the second surface.

15. The method of claim 1, wherein the optical label is a fluorescent label.

16. The method of claim 15, wherein detecting the fluorescent label includes detection by a fluorescence microscope without an autofocus.

17. The method of claim 16, wherein detecting the fluorescent label includes detection by a fluorescence microscope including a fixed focus.

18. The method of claim 1, wherein the first complex includes a nucleic acid.

19. The method of claim 18, further comprising amplifying the nucleic acid between the first surface and the second surface in a cyclic amplification reaction.

20. The method of claim 19, further comprising detecting the first complex after one or more cycles of the cyclic amplification reaction.

* * * * *

SEQUENCE LISTING

```
<160> NUMBER OF SEQ ID NOS: 13

<210> SEQ ID NO 1
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgaggctggg aarctgaca                                                 19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggygaggay aacgaaatc                                                 19

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccctgaatgc ggctaat                                                   17

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
attgtcacca taagcagcc                                                 19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctcgtaaaat ggcccctcc                                                 19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggccgtgtg acactatcg                                                 19

<210> SEQ ID NO 7
<211> LENGTH: 21
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 7
cgctctcgta aatgcttccc t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tctacccaca acagacccac g                                              21

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcgcgtgctg cggc                                                      14

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cggcatggcc cgtctat                                                   17

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgttgggcaa ccaccgcact g                                              21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
agagtttgat cctggctcag                                                20

<210> SEQ ID NO 13
<211> LENGTH: 27
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 13
taccgtcacc ataaggcttc gtccta                                            27
```